US010620222B2

(12) United States Patent
Moreau et al.

(10) Patent No.: US 10,620,222 B2
(45) Date of Patent: Apr. 14, 2020

(54) ELECTRIFIED COMPOSITIONS FOR DETERMINING THE RISK OF DEVELOPING ADOLESCENT IDIOPATHIC SCOLIOSIS THROUGH THE USE OF GI PROTEIN RECEPTOR

(71) Applicant: CHU Sainte-Justine, Montreal (CA)

(72) Inventors: Alain Moreau, Montreal (CA); Marie-Yvonne Akoume Ndong, Montreal (CA)

(73) Assignee: CHU Sainte-Justine, Montreal (CA)

( * ) Notice: Subject to any disclaimer, the term of this patent is extended or adjusted under 35 U.S.C. 154(b) by 261 days.

(21) Appl. No.: 14/804,225

(22) Filed: Jul. 20, 2015

(65) Prior Publication Data

US 2016/0146839 A1    May 26, 2016

Related U.S. Application Data

(63) Continuation of application No. 13/123,146, filed as application No. PCT/CA2009/001453 on Oct. 13, 2009, now abandoned.

(60) Provisional application No. 61/228,769, filed on Jul. 27, 2009, provisional application No. 61/104,442, filed on Oct. 10, 2008.

(51) Int. Cl.
| | |
|---|---|
| *C12N 5/00* | (2006.01) |
| *C12N 5/07* | (2010.01) |
| *C12N 5/071* | (2010.01) |
| *C12N 5/078* | (2010.01) |
| *C12N 5/0786* | (2010.01) |
| *C12N 5/0781* | (2010.01) |
| *C12N 5/0783* | (2010.01) |
| *G01N 33/48* | (2006.01) |
| *G01N 33/00* | (2006.01) |
| *G01N 33/49* | (2006.01) |
| *G01N 33/50* | (2006.01) |
| *G01N 33/566* | (2006.01) |
| *G01N 33/567* | (2006.01) |
| *A61K 49/00* | (2006.01) |
| *G01N 33/74* | (2006.01) |
| *G01N 33/68* | (2006.01) |
| *A61K 31/4164* | (2006.01) |
| *A61K 31/4045* | (2006.01) |
| *A61K 31/498* | (2006.01) |
| *G01N 33/554* | (2006.01) |
| *A61K 31/415* | (2006.01) |

(52) U.S. Cl.
CPC ......... *G01N 33/74* (2013.01); *G01N 33/5008* (2013.01); *G01N 33/566* (2013.01); *G01N 33/6872* (2013.01); *A61K 31/4045* (2013.01); *A61K 31/415* (2013.01); *A61K 31/4164* (2013.01); *A61K 31/498* (2013.01); *A61K 2300/00* (2013.01); *G01N 33/554* (2013.01); *G01N 2333/4719* (2013.01); *G01N 2333/726* (2013.01); *G01N 2800/10* (2013.01); *G01N 2800/38* (2013.01); *G01N 2800/50* (2013.01); *G01N 2800/52* (2013.01)

(58) Field of Classification Search
CPC ................ A61K 38/00; C07K 14/4702; C07K 14/4703; C07K 14/705; G01N 2333/4719; G01N 2333/726; G01N 33/5008; G01N 33/5044; G01N 33/566; G01N 33/6872; G01N 33/6896; G01N 2800/108; G01N 33/5041; G01N 33/5088; G01N 33/56966; G01N 2800/10; G01N 33/57484; G06F 19/16; C12Q 2600/158
See application file for complete search history.

(56) References Cited

U.S. PATENT DOCUMENTS

| | | | | |
|---|---|---|---|---|
| 7,094,593 B1* | 8/2006 | Pausch | ................. | C07K 14/705 435/254.11 |
| 7,504,407 B2* | 3/2009 | Castelhano | .......... | C07D 487/04 514/265.1 |
| 7,989,175 B2* | 8/2011 | Moreau | .................. | C12Q 1/527 435/7.21 |
| 8,313,898 B2* | 11/2012 | Fang | ...................... | C12Q 1/025 435/325 |
| 8,652,791 B2* | 2/2014 | Moreau | ................. | C12Q 1/527 435/29 |

(Continued)

FOREIGN PATENT DOCUMENTS

| | | |
|---|---|---|
| JP | 2000-354500 | 12/2000 |
| WO | WO 03/073102 | 4/2003 |

(Continued)

OTHER PUBLICATIONS

Nelson et al. Spine, 2010; 36:37-40.*
Yaman et al. Turk Neurosurg. 2014; 24:646-657.*
Letellier et al. J. Pineal Res. Oct. 9, 2008; https://doi.org/10.1111/j.1600-079X.2008.00603.x abstract.*
Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*

(Continued)

*Primary Examiner* — Chang-Yu Wang
(74) *Attorney, Agent, or Firm* — Klarquist Sparkman, LLP

(57) ABSTRACT

Methods for diagnosing a predisposition to developing a scoliosis (e.g., adolescent idiopathic scoliosis (AIS)) and identifying compounds for treating scoliosis based on the modulation of Gi protein-coupled receptor activity are described. Specific embodiments of the methods involve measuring a change in impedance signals of cells expressing a receptor coupled to a Gi protein with a ligand. To identify compounds useful in treatment, the cell is contacted with a test compound and a ligand. A higher impedance in the presence relative to the absence of said test compound is indicative that the test compound is useful for treating scoliosis.

28 Claims, 93 Drawing Sheets

(56) References Cited

U.S. PATENT DOCUMENTS

| | | | | |
|---|---|---|---|---|
| 2004/0250299 | A1* | 12/2004 | Verwaerde | A01K 67/0333 800/3 |
| 2005/0130250 | A1* | 6/2005 | Moreau | C12Q 1/527 435/21 |
| 2008/0032317 | A1* | 2/2008 | Pausch | C07K 14/705 435/7.31 |
| 2008/0153124 | A1* | 6/2008 | Pausch | C07K 14/705 435/29 |
| 2008/0274913 | A1* | 11/2008 | Lee | G01N 33/5023 506/14 |
| 2009/0093011 | A1* | 4/2009 | Fang | G01N 33/5008 435/29 |
| 2009/0098645 | A1* | 4/2009 | Fang | C12M 25/06 435/305.1 |
| 2009/0111110 | A1* | 4/2009 | Moreau | C12Q 1/527 435/6.16 |
| 2009/0148850 | A1* | 6/2009 | Kargman | G01N 33/566 435/6.16 |
| 2009/0226931 | A1* | 9/2009 | Bunch | C12Q 1/025 435/7.1 |
| 2011/0256582 | A1* | 10/2011 | Moreau | C12Q 1/527 435/29 |
| 2012/0009600 | A1* | 1/2012 | Moreau | C12Q 1/527 435/7.21 |
| 2013/0115615 | A1* | 5/2013 | Moreau | C12Q 1/527 435/6.12 |

FOREIGN PATENT DOCUMENTS

| | | | |
|---|---|---|---|
| WO | WO 03/073102 | 9/2003 | |
| WO | WO03073102 | * 9/2003 | G01N 38/68 |
| WO | WO2010/040234 | 4/2011 | |

OTHER PUBLICATIONS

Guo et al., PNAS 2004; 101:9205-9210.*

Akoume et al., "Cell-based screening test for idiopathic scoliosis using cellular dielectric spectroscopy," *Spine*, 35(13): E601-E608, 2010.

Axenovich et al., "Segregation Analysis of Idiopathic Scoliosis: Demonstration of a Major Gene Effect," *Am J Med Genet*, 86(4): 389-394, 1999.

Blank et al., "A genomic approach to scoliosis pathogenesis," *Lupus*, 8(5): 356-360, 1999.

Giampietro PF et al., "Synteny-Defined Candidate Genes for Congenital and Idiopathic Scoliosis," *Am J Med Genet*, 83(3):164-177, 1999.

Goldberg et al., "The Ste-Justine Adolescent Idiopathic Scoliosis Cohort Study Part I: Description of the study," *Spine* 19:1551-1561, 1994.

Huang et al., "Cell-electronic sensing of particle-induced cellular responses," *Analyst*, 133(5): 643-648, 2008.

Hyatt et al., "Initiation of vertebrate left-right axis formation by maternal Vg1," *Nature*, 384(6604): 62-65, 1996.

Letellier et al., "Récents progrés dans 1 'étiopathogénie de la scoliose idiopathique de 1 'adolescent et nouveaux concepts moléculaires," *Médecine/Sciences*, 23(11): 910-916, 2007.

Letellier et al., "Estrogen cross-talk with the melatonin signaling pathway in human osteoblasts derived from adolescent idiopathic scoliosis patients," *J. Pineal Res.*, 45: 383-393, 2008.

Machida M., "Cause of Idiopathic Scoliosis," *Spine*, 24(24): 2576-2583, 1999.

Medhurst et al., "Pharmacological and immunohistochemical characterization of the APJ receptor and its endogenous ligand apelin," *J Neurochem.*, 84(5):1162-1172, 2003.

Moreau et al., "Melatonin Signaling Dysfunction in Adolescent Idiopathic Scoliosis," *Spine*, 29:1772-1781, 2004.

Moreau et al., "Estrogen cross-talk with the melatonin signaling pathway in human osteoblasts derived from adolescent idiopathic scoliosis patients," *J. Pineal Res.*, 45:383-393, 2008.

Moreau et al., "Molecular and genetic aspects of idiopathic scoliosis, Blood test for idiopathic scoliosis," *Orthopade*, 38(2):114-116, 2009.

Niswender et al., "A Novel Assay of Gi/o-Linked G Protein-Coupled Receptor Coupling to Potassium Channels Provides New Insights into the Pharmacology of the Group III Metabotropic Glutamate Receptors," *Mol Pharmacol*, 73(4):1213-1224, 2008.

Notice of Reasons for Rejection, Japanese Patent Application No. 2011/530342, dated Nov. 6, 2012, 4 pages.

Official Letter, Taiwanese Application No. 98134337, dated Jul. 15, 2013, 4 pages.

Patent Examination Report No. 1, Australian Patent Application No. 2009301605, dated Sep. 20, 2012, 3 pages.

Poitras et al., "The Ste-Justine Adolescent Idiopathic Scoliosis Cohort Study. Part IV: Surgical correction and back pain," *Spine*, 19:1582-1588, 1994.

Riobo et al., "Activation of heterotrimeric G proteins by Smoothened," *Proc. Natl. Acad. Sci. USA*, 103(33):12607-12612, 2006.

Roth et al., "Melatonin Promotes Osteoblast Differentiation and Bone Formation," *J Biol Chem* 274(31): 22041-22047, 1999.

Saugstad et al., "Metabotropic Glutamate Receptors Activate G-Protein-Coupled Inwardly Rectifying Potassium Channels in Xenopus Oocytes," *J. Neurosci.*, 16(19):5979-5985, 1996.

Solly et al., "Application of Real-Time Cell Electronic Sensing (RT-CES) Technology to Cell-Based Assays," *Assay Drug Dev. Technol.*, 2(4): 363-372, 2004.

Supplementary European Search Report, European Patent Application No. EP 09818732, dated Mar. 6, 2012; 9 pages.

Von Gall et al., "Transcription factor dynamics and neuroendocrine signalling in the mouse pineal gland: a comparative analysis of melatonin-deficient C57BL mice and melatonin-proficient C3H mice," *Eur J Neurosci*, 12(3):964-972, 2000.

Weinstein et al., "Adolescent idiopathic scoliosis," *Lancet*, 371:1527-1537, 2008.

Weiss et al., "Rate of complications in scoliosis surgery—a systematic review of the Pub Med literature," *Scoliosis*, 3:9, 2008.

Wise et al., "Localization of Susceptibility to Familial Idiopathic Scoliosis," *Spine*, 25(18): 2372-2380, 2000.

International Search Report and Written Opinion, PCT Application No. PCT/CA2009/001453 (dated Jan. 25, 2010).

International Preliminary Report on Patentability, PCT Application No. PCT/CA2009/001453 (dated Apr. 21, 2011).

Office Action from the Canadian Intellectual Property Office dated May 17, 2016, issued in corresponding Canadian Application No. 2,738,840 (4 pages).

Azeddine et al., "Molecular Determinants of Melatonin Signaling Dysfunction in Adolescent Idiopathic Scoliosis," *Clin Orthop Relat Res* 462:45-52, 2007.

Examination Report from corresponding Indian Application No. 1403/KOLNP/2011, dated Nov. 17, 2016 (9 pages).

Peters et al., "Evaluation of Cellular Dielectric Spectroscopy, a Whole-Cell, Label-Free Technology for Drug Discovery on $G_i$-Coupled GPCRs," *J Biomol Screen* 12:312-319, 2007.

Office Action issued in Argentina Application No. 20090103920 dated Dec. 20, 2017, accompanied by an English-language summary letter (6 pages).

* cited by examiner

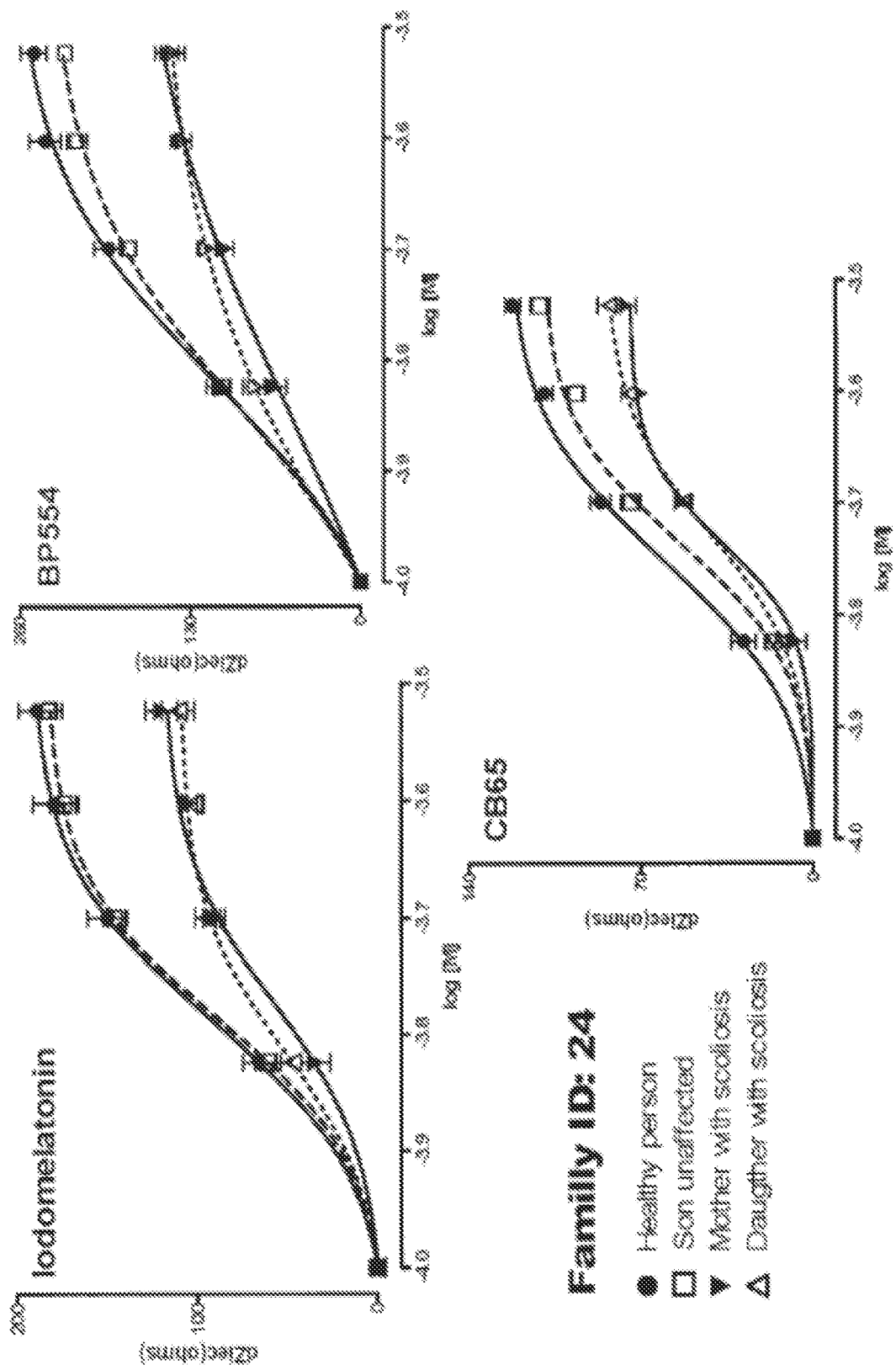

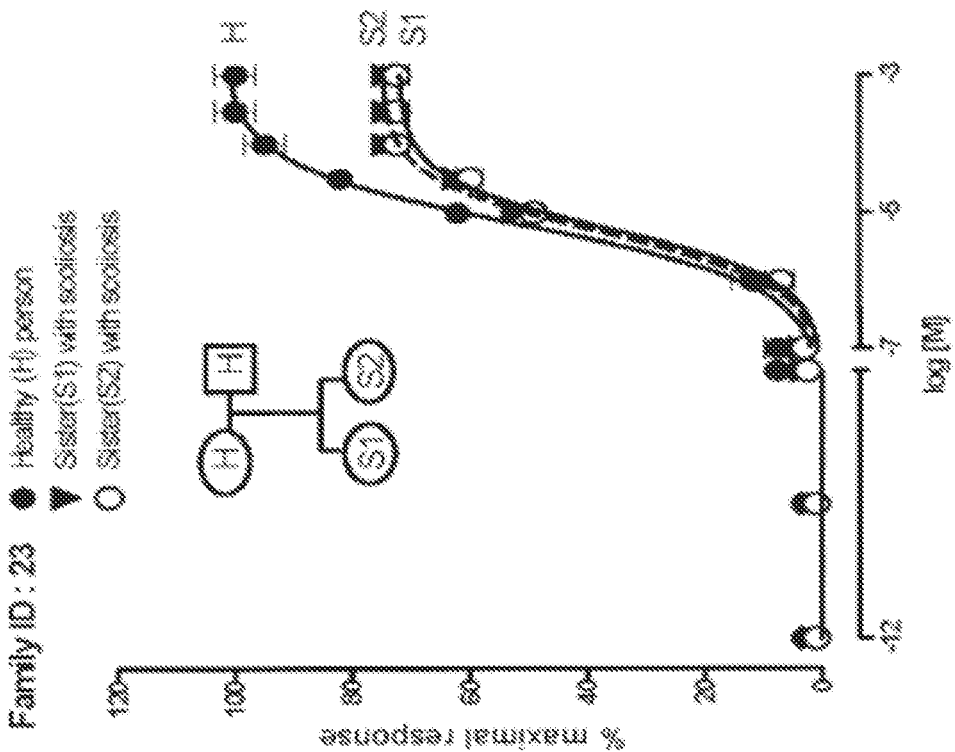
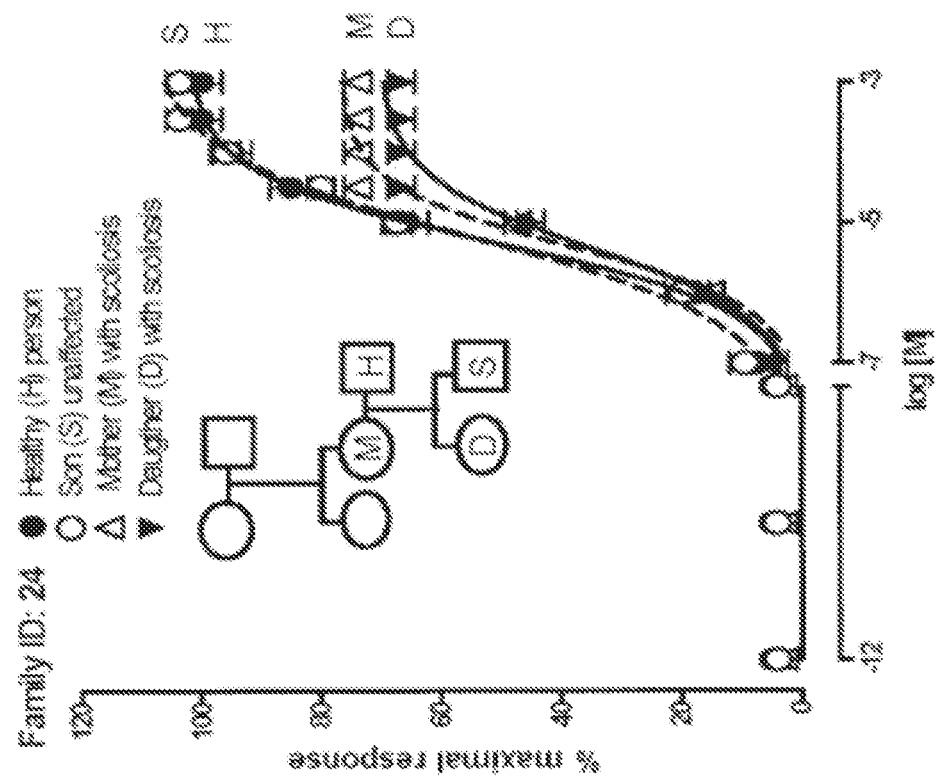
FIG. 10A

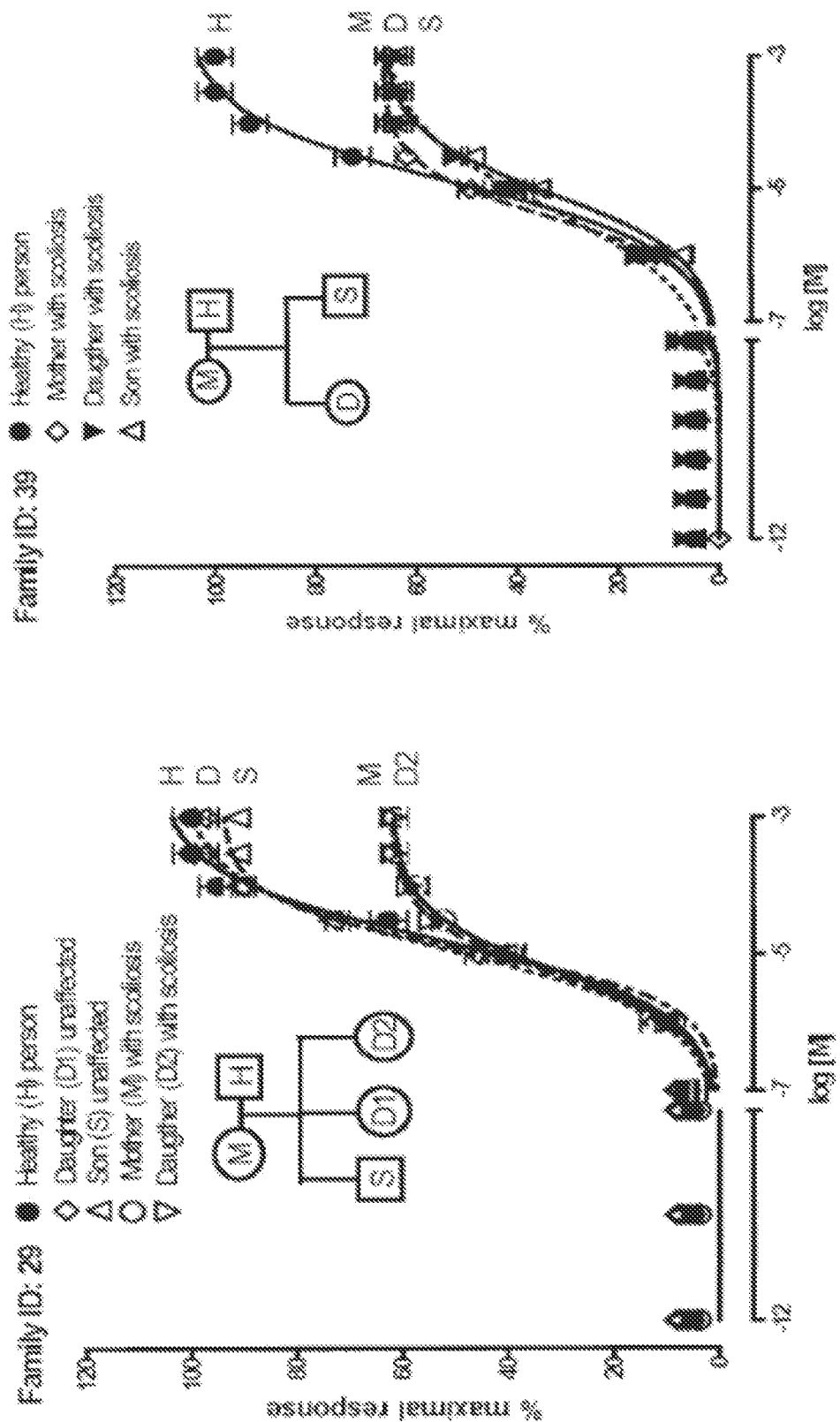

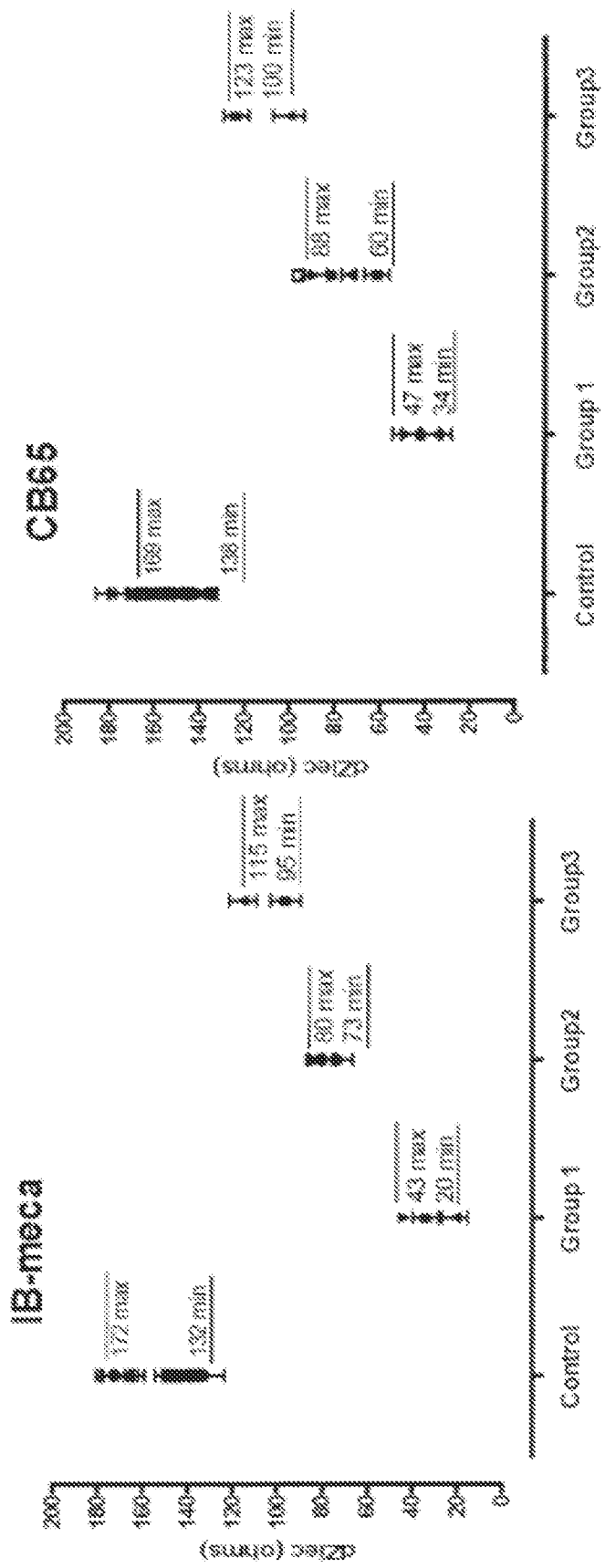

FIG. 15A

| Adenosine receptors | | |
|---|---|---|
| Subtype | Coupling | Reference |
| A1 | Gi | Fredholm et al., 2001 |
| A3 | Gi | |

| Adrenoreceptors | | |
|---|---|---|
| Subtype | Coupling | Reference |
| Alpha2 | Gi | |

| Angiotensin receptors | | |
|---|---|---|
| Subtype | Coupling | Reference |
| At1 | Gi / Gq | Gasparo et al., 2000 in Pharmacol. Rev. 52 (3) |
| At2 | Gi | |

| Apelin receptors | | |
|---|---|---|
| Subtype | Coupling | Reference |
| APJ | Gi | Iturrioz et al., 2007 in: Arch Mal Coeur Vaiss.100 (8) |

| Bradykinin receptors | | |
|---|---|---|
| Subtype | Coupling | Reference |
| B2 | Gi / Gq | Leeb-Lundberg et al., 2005 in Pharmacol. Rev. 54 (1) |

FIG. 15B

| Cannabinoid receptors | | |
|---|---|---|
| Subtype | Coupling | References |
| CB2 | Gi | Pacher et al., 2006 In Pharmacol. Rev. 58 (3) |

| Calcium-sensing receptors | | |
|---|---|---|
| Subtype | Coupling | References |
| CaS | Gi /Gq | Chang et al., 1998 In: J Bone Miner Res., 13, |
| GPRC$_6$ | | |

| Chemokine receptors | | |
|---|---|---|
| Subtype | Coupling | Reference |
| CCR | Gi / Gq | Murphy et al., 2000 In Pharmacol. Rev. 52 (1); |
| CXCR | | |

| Dopamine receptors | | |
|---|---|---|
| Subtype | Coupling | References |
| D2 | Gi | |
| D3 | Gi | |
| D4 | Gi | |

| Frizzled receptors | | |
|---|---|---|
| Subtype | Coupling | References |
| FZD2 | Gi /Gq | Ma and Wang 2007 In: J Biol Chem, 282 |
| SMO | Gi | Riobo et al., 2006 In: Proc Natl Acad Sci, 103 |

FIG. 15C

Free fatty acid receptors

| Subtype | Coupling | References |
|---|---|---|
| FFA2 | Gi / Gq | Le Poul et al., 2003 |
| FFA3 | | In: J Biol Chem, 278, |

Galanin receptors

| Subtype | Coupling | References |
|---|---|---|
| GAL1 | Gi | Lang et al., 2007 |
| GAL2 | | In: Pharmacology and |
| GAL3 | | therapeutic 115 (2) |

GABAB receptors

| Subtype | Coupling | References |
|---|---|---|
| GABA | Gi | Barnard et 1998 In:Pharmacol. Rev.50 (2) |

Histamine receptors

| Subtype | Coupling | Reference |
|---|---|---|
| H3 | Gi | Hill et al., 1997 |
| H4 | | In pharmacol. Rev. 49 (3) |

Serotonin receptors

| Subtype | Coupling | Reference |
|---|---|---|
| 5HT1 | Gi | Hoyer et 1994 |
| 5HT5 | Gi | In Pharmacol. Rev. 46 (2) |

FIG. 15D

| Leukotriene receptors | | |
|---|---|---|
| Subtype | Coupling | Reference |
| LTB | Gi / Gq | Nabe et al., 1994<br>Prostaglandins Leukot. Essent. Fatty Acids |
| OXE | Gi | |
| Lysophospholipid receptors | | |
| Subtype | Coupling | Reference |
| LPA | Gi / Gq | |
| SP | Gi | |

| Neuropeptide W/neuropeptide B receptors | | |
|---|---|---|
| Subtype | Coupling | References |
| NPBW1 | Gi | Fujii et al., 2002<br>In: J. Biol. Chem. 277 |
| NPBW2 | Gi | Brezillon et al., 2003<br>In: J. Biol. Chem. 278 |

FIG. 15E

| Metabotropic glutamate receptors | | |
|---|---|---|
| Subtype | Coupling | Reference |
| mGLu2 | Gi | Tanabe et al., 1992 In: Neuron 8 |
| mGLu3 | Gi | Kingston et al., 1998 In: Neuropharmacology 37 |
| mGLu4 | Gi/Gq | Tanabe 1993 In: J Neurosci., 13; Brabet et al., 1998 In: Neuropharmacology 37 |
| mGLU6 | Gi | Laurie et al., 1997 In: Neuropharmacology 36 |
| mGLu7 | Gi/Gq | Kingston et al., 1998 In: Neuropharmacology 37; Abe et al., 1992 In: J Biol. Chem. 267 |
| mGLu8 | Gi | Wu et al., 1998 In: Brain Res. Mol. Brain Res., 53, |

FIG. 15F

| Neuropeptide Y receptors | | |
|---|---|---|
| Subtype | Coupling | References |
| Y1 | Gi/Gq | Krause et al., 1992 In: Mol. Pharmacol. 41; Herzog et al., 1992 In: Proc. Natl. Acad. Sci. 89 |
| Y2 | Gi/Gq | Shigeri and Fujimoto 1994 In: J. Biol. Chem. 269; Lynch et al., 1994 In: J. Biol. Chem. 269 |
| Y4 | Gi/Gq | Bard et al., 1995 In: J. Biol. Chem. 270 |
| Y5 | Gi | Gerald et al., 1996 In: Nature, 382 |

| Neuropeptide FF/AF receptors | | |
|---|---|---|
| Subtype | Coupling | References |
| NPFF1 | Gi | Hinuma et al., 2000 In: Nat Cell Biol 2 |
| NPFF2 | Gi | Elshourbagy et al., 2000 In: J. Biol. Chem. 275 |

| Nicotinic acid receptor family | | |
|---|---|---|
| GPR81 | Gi | Wise et al., 2003 In: J. Biol. Chem. 278 |
| GPR109A | Gi | Soga et al., 23003 Biochem Biophys Res Commun, 303 |
| GPR109B | Gi | Jung et al., 2007. In: J. Med Chem. 50 |

FIG. 15G

| Opioid receptors | | |
|---|---|---|
| Subtype | Coupling | References |
| δ | Gi | Sharma et al., 1977 In:Proc Natl Acad Sci 74 |
| κ | Gi | Lawrence and Bidlack 1993 J Pharmacol Exp Ther, 266, |
| μ | Gi | Yu et al., 1990 J Neurochem, 55 |

| Orexin receptors | | |
|---|---|---|
| Subtype | Coupling | References |
| $OX_1$ | Gi / Gq | Holmqvist et al., 2005 In: J Biol Chem, 280 |

| P2Y receptors | | |
|---|---|---|
| Subtype | Coupling | References |
| P2Y12 | Gi | Hollopeter et al., 2001 Nature, 409 |
| P2Y13 | Gi | Marteau et al., 2003, In: Mol Pharmacol, 64, |
| P2Y14 | Gi | Scrivens and Dickenson 2005 Br J Pharmacol, 146 |

| Prostanoid receptors | | |
|---|---|---|
| Subtype | Coupling | References |
| DP2 | Gi | Sawyer et al., 2002 In: Br J Pharmacol, 137 |

| Somatostatin receptors | | |
|---|---|---|
| Subtype | Coupling | References |
| SST1 | Gi | Rivier et al., 2001, J Med Chem, 44, |
| SST2 | | Nunn et al., 2003, Eur J Pharmacol, 465 |
| SST3 | | Poitout et al., 2001 J Med Chem, 44 |
| SST4 | | Liu et al., 1998, J Med Chem, 41 |

FIG. 16A    Ligands of Receptors Coupled to Gi Protein

Adenosine A1 receptor

| Agonists | References | Antagonists | References |
|---|---|---|---|
| (R,S)-PHPNECA | Volpini et al., 2002 J Med Chem, 45 | AS100; AS70; | Varani, K., et al., 2005 Biochem Pharmacol, 70 |
| (R)-PIA | Rivkeeset al., 1999, J. Biol. Chem., 274 | caffeine | Deckert, ET AL.,1993 Neurosci Lett, 150 |
| (S)-PIA | Jockers, et al., 1994 ,J Biol Chem, 269 | CGS 15943 | Ongini, ET AL., 1999, Naunyn Schmiedebergs Arch. Pharmacol., 359, |
| CCPA | Obiefuna et al 2005 J Pharmacol Exp Ther, 315, | CPT | Dalpiaz, ET AL., 1998, Biochem Pharmacol, 56 |
| CGS 21680 | Gao et al., 2004 Biochem Pharmacol, 68 | DPCPX, | Rivkees, ET AL., 1999, J. Biol. Chem., 274 |
| 2-chloroadenosine | Rivkeeset al., 1999 J. Biol. Chem., 274 | Flavanone | Karton, et AL.,1996 J Med Chem, 39 |
| CV-510 | Peterman and Sanoski, () Cardiol Rev, 13 | FR194921 | Maemoto, et al., 2004 J Pharmacol Sci, 96, |
| cyclopentyladenosine | Rivkeeset al., 1999 J. Biol. Chem., 274 | galangin | Karton, et AL.,1996 J Med Chem, 39 |
| 2-hexynyl-NECA | Volpini et al., 2002 J Med Chem, 45 | IBMX | Jockerset al.,1994, J Biol Chem, 269 |
| LUF5831 | Heitman, et al., 2006 Br J Pharmacol, 147 | L-97-1 | Obiefuna, et al., 2005, J Pharmacol Exp Ther, 315 |
| NECA | Rivkeeset al., 1999 J. Biol. Chem., 274 | morin | Karton, et AL.,1996 J Med Chem, 39 |
| PENECA | Volpini et al., 2002 J Med Chem, 45 | MRE 2029F20 | Varani, et al., 2005, Biochem Pharmacol, 70 |
| | | MRS1041, sakuranetin | Karton, et AL.,1996 J Med Chem, 39 |
| | | SCH 58261 | Ongini, et al.,1999, Naunyn Schmiedebergs Arch. Pharmacol., 359 |
| | | Theophylline XAC | Jockers, et al., 1994, J Biol Chem, 269 |
| | | ZM 241385 | Ongini, et al., 1999, Naunyn Schmiedebergs Arch. Pharmacol., 359 |

FIG. 16B

Adenosine A3 receptor

| Agonists | References | Antagonists | References |
|---|---|---|---|
| (R,S)-PHPNECA | Volpini et al., 2002 *J Med Chem*, 45 | (R)-niguldipine | van Rhee et al., 1996 *J Med Chem*, 39 |
| (R)-PIA | Olah et al., 1994 *J Biol Chem*, 269 | (R,S)-nicardipin | |
| (S)-PIA | Arani et al., 2000 *Mol Pharmacol*, 57 | BW-A1433 | Salvatore et al., 1993 *Proc. Natl. Acad. Sci.* 90 |
| AB-MECA | Olah et al., 1994 *J Biol Chem*, 269 | CGS 15943 | Varani et al., 2000 *Mol Pharmacol*, 57 |
| [$^{125}$I]AB-MECA | Zhou et al., 1992 *Proc. Natl. Acad. Sci.* 89 | DPCPX | Olah et al., 1994 *J Biol Chem*, 269 |
| [$^3$H]AB-MECA | Klotz et al., 1998 *Naunyn Schmiedebergs Arch. Pharmacol.*, 357 | Flavone, Flavanone, | Karton et al., 1996 *J Med Chem*, 39 |
| [$^3$H]APNEA | | galangin | |
| CCPA | Jacobson et al., 1997 *Neuropharmacology*, 36 | I-ABOPX | Salvatore et al.,1993 *Proc. Natl. Acad. Sci.* 90 |
| CGS 21680 | Salvatore et al., 1993 *Proc. Natl. Acad. Sci.* 90 | MRE 3008F20, [$^3$H]MRE 3008F20 | Varani et al., 2000 *Mol Pharmacol*, 57 |
| Cl-IB-MECA | Volpini et al., 2002 *J Med Chem*, 45 | MRE 3010F20, RS1041, MRS1042 MRS1067, MRS1088, MRS1093, MRS1097, MRS1177 MRS1186, MRS1191 MRS1191, MRS1220 MRS1476, MRS1486 MRS1505, MRS1523 MRS1523, MRS928 | Karton et al., 1996, *J Med Chem*, 39 |
| cyclopentyladenosine | | | Jacobson et al., 1997 *Neuropharmacology*, 36 |
| 2-hexynyl-NECA | | | van Rhee et al., 1996, *J Med Chem*, 39 |
| I-ABA | Salvatore et al., 1993 *Proc. Natl. Acad. Sci.* 90 | | Kim et al.,1996 *J Med Chem*, 39, |

FIG. 16C

| Adenosine A3 receptor | | | |
|---|---|---|---|
| Agonists | References | Antagonists | References |
| IAB-MECA, IB-MECA | Klotz et al., 1998 Naunyn Schmiedebergs Arch. Pharmacol., 357 | sakuranetin | Karton et al., 1996, J Med Chem, 39 |
| MPC-MECA | Varani et al., 2000 Mol Pharmacol, 57 | theophylline | Klotz et al., 1998 Naunyn Schmiedebergs Arch. Pharmacol., 357 |
| NECA | Jacobson et al., 1997 Neuropharmacology, 36 | visnagin | Karton et al., 1996, J Med Chem, 39 |
| [$^3$H]NECA | Feoktistov et al., 2001 Biochem Pharmacol, 62 | VUF8504 | van et al., 1998 J. Med. Chem., 41 |
| PENECA | Volpini et al., 2002 J Med Chem, 45 | VUF8507 | |
| | | XAC | Olah et al., 1994 J Biol Chem, 269 |

FIG. 16D

Adrenoreceptor Alpha2A

| Agonists | References | Antagonists | References |
|---|---|---|---|
| adrenaline | | ARC-239 | Uhlén et al., 1994 *J Pharmacol Exp Ther*, 271 |
| apomorphine | | BRL 44408 | Millan et al., 2002 *J Pharmacol Exp Ther*, 303 |
| brimonidine | | bromocriptine | Devedjian et al., 1994 *Eur J Pharmacol.*, 252 |
| clonidine | Asper et al., 1998 *Biochem Pharmacol.*, 55 | cabergoline | |
| dexmedetomidine | | chlorpromazine | Millan et al., 2002 *J Pharmacol Exp Ther*, 303 |
| guanfacine | | lisuride | Uhlén et al., 1994 *J Pharmacol Exp Ther*, 271 |
| noradrenaline | | [³H]MK-912 | Devedjian et al., 1994 *Eur J Pharmacol.*, 252 |
| oxymetazoline | | phentolamine | Millan et al., 2002 *J Pharmacol Exp Ther*, 303 |
| pergolide | Millan et al., 2002 *J Pharmacol Exp Ther*, 303 | piribedil | Devedjian et al., 1994 *Eur J Pharmacol.*, 252 |
| xylazine | Asper et al., 1998 *Biochem Pharmacol.*, 55 | prazosin | |
| | | rauwolscine | Uhlén et al., 1994 *J Pharmacol Exp Ther*, 27 |
| | | [³H]rauwolscine | Bylund et al., 1992 *Mol Pharmacol.*, 42 |
| | | RX821002 | Uhlén et al., 1994 *J Pharmacol Exp Ther*, 271 |
| | | spiroxatrine | |
| | | terguride | Millan et al., 2002 *J Pharmacol Exp Ther*, 303 |
| | | WB 4101 | |
| | | yohimbine | Uhlén et al., 1994 *J Pharmacol Exp Ther*, 271 |

FIG. 16E

Adrenoreceptor Alpha2B

| Agonists | References | Antagonists | References |
|---|---|---|---|
| adrenaline | | apomorphine | Millan, et al., 2002 J Pharmacol Exp Ther, 303 |
| brimonidine | | ARC-239 | Bylund, et al., 1992 Mol Pharmacol., 42 |
| clonidine | | BRL 44408 | Uhlén et al., 1994 J Pharmacol Exp Ther, 271 |
| dexmedetomidine | Jasper et al., 1998 Biochem Pharmacol., 55 | bromocriptine | Millan, et al., 2002 J Pharmacol Exp Ther, 303 |
| guanfacine | | cabergoline | |
| noradrenaline | | chlorpromazine | Millan, et al., 2002 J Pharmacol Exp Ther, 303 |
| oxymetazoline | | lisuride | Millan, et al., 2002 J Pharmacol Exp Ther, 303 |
| pergolide | Millan, et al., 2002 J Pharmacol Exp Ther, 303 | [³H]MK-912 | Uhlén et al., 1994 J Pharmacol Exp Ther, 271 |
| xylazine | Jasper et al., 1998 Biochem Pharmacol., 55 | phentolamine | Bylund, et al., 1992 Mol Pharmacol., 42, |
| | | prazosin | |
| | | rauwolscine | |
| | | roxindole | Uhlén et al., 1994 J Pharmacol Exp Ther, 271 |
| | | RX821002 | Millan, et al., 2002 J Pharmacol Exp Ther, 30 |
| | | spiroxatrine | Uhlén et al., 1994 J Pharmacol Exp Ther, 271 |
| | | terguride | Millan, et al., 2002 J Pharmacol Exp Ther, 30 |
| | | WB 4101 | |
| | | yohimbine | Bylund, et al., 1992 Mol Pharmacol., 42, |

FIG. 16F

Adrenoreceptor Alpha2C

| Agonists | References | | Antagonists | References |
|---|---|---|---|---|
| adrenaline | | | apomorphine | Millan et al., 2002 J Pharmacol Exp Ther, 303 |
| brimonidine | | | ARC-239 | Bylund et al., 1992, Mol Pharmacol., 42, |
| clonidine | | | BRL 44408 | Uhlén et al., 1994, J Pharmacol Exp Ther, 271 |
| dexmedetomidine | Jasper et al., 1998 Biochem Pharmacol., 55 | | bromocriptine | Millan, et al., 2002 J Pharmacol Exp Ther, 303 |
| guanfacine | | | cabergoline | Bylund et al., 1992, Mol Pharmacol., 42, |
| noradrenaline | | | chlorpromazine | |
| Oxymetazoline | | | lisuride | Millan, et al., 2002 J Pharmacol Exp Ther, 303 |
| Pergolide | Millan, et al., 2002 J Pharmacol Exp Ther, 303 | | [³H]MK-912 | Uhlén et al., 1994, J Pharmacol Exp Ther, 271 |
| xylazine | Jasper et al., 1998 Biochem Pharmacol., 55 | | phentolamine | Bylund et al., 1992, Mol Pharmacol., 42, |
| | | | Piribedil, prazosin | Millan, et al., 2002 J Pharmacol Exp Ther, 303 |
| | | | rauwolscine roxindole | Uhlén et al., 1994, J Pharmacol Exp Ther, 271 |
| | | | RX821002 | Millan, et al., 2002 J Pharmacol Exp Ther, 303 |
| | | | spiroxatrine | Uhlén et al., 1994, J Pharmacol Exp Ther, 271 |
| | | | Terguride, WB 4101 | Millan, et al., 2002 J Pharmacol Exp Ther, 303 |
| | | | yohimbine | Uhlén et al., 1994, J Pharmacol Exp Ther, 271 |

FIG. 16G

Angiotensin AT2 receptors

| Agonists | References |
|---|---|
| ang I | Whitebread et al, 1989 Biochem. Biophys. Res. Commun., 163 |
| ang II | Speth and Kim 1990 Biochem. Biophys. Res. Commun., 169 |
| [p-aminoPhe6] ang II | |
| ang III | Whitebread et al, 1989 Biochem. Biophys. Res. Commun., 163 |
| CGP42112 | |

| Antagonists | References |
|---|---|
| PD123177 | Chiu et al., 1989 Biochem. Biophys. Res. Commun., 165 |
| PD123319 | Wiest et al, 1991 J. Cardiovasc. Pharmacol., 17 |
| Saralasin | Chiu et al., 1989 Biochem. Biophys. Res. Commun., 165 |

Apelin receptor

| Agonists | References |
|---|---|
| [$^3$H][(Pyr$^1$)][Met(O)11]-apelin-13 | Medhurst et al., 2003 J Neurochem., 84, |
| [$^{125}$I][(Pyr$^1$)][Nle$^{75}$,Tyr$^{77}$]-apelin-13 | Hosoya et al., 2000 J Biol Chem., 275 |
| [$^{125}$I][(Pyr$^1$)]apelin-13 | Katugampola et al., 2001 Br J Pharmacol., 132 |
| [$^{125}$I][Nle$^{75}$,Tyr$^{77}$]apelin-36 | Medhurst et al., 2003 J Neurochem., 84, |
| apelin-13 | |
| apelin-36 | Medhurst et al., 2003 J Neurochem., 84, |
| Pyr$^1$-apelin-13 | |

| Antagonists | References |
|---|---|
| ALX40-4C | Zhou et al., 2003 Virology, 307 |

FIG. 16H

Cannabinoid CB2 receptors

| Agonists | References | Antagonists | References |
|---|---|---|---|
| Δ⁹-THC | Felder et al., 1995 Mol. Pharmacol., 48 | AM630 | |
| arachidonoyl ethanolamide | Mechoulam et al., 1995 Biochem. Pharmacol., 50 | | |
| 2-arachidonoylglycerol | | | |
| CP55940 | Felder et al., 1995 Mol. Pharmacol., 48 | | |
| [³H]CP55940 | Hanus et al. 1999 Proc. Natl. Acad. Sci. 96 | | |
| HU-210 | | | |
| HU-308 | Huffman et al., 1999, Bioorg. Med. Chem., 7 | SR144528 | Ross et al., 1999 Br. J. Pharmacol., 126 |
| JWH-133 | Ross et al., 1999 Br. J. Pharmacol., 126 | | |
| L-759,633 | Felder et al., 1995 Mol. Pharmacol., 48 | | |
| WIN55212-2 | Munro et al., 1993 Nature, 365 | | |
| [³H]WIN55212-2 | | | |

FIG. 16I

Calcium-sensing CaS receptors

| Agonists | References | Antagonists | References |
|---|---|---|---|
| Ca$^{2+}$ | Riccardi et al., 1995 Proc Natl Acad Sci 92 | 1-arylmethylpyrrolidin-2-yl ethanol amines | Gavai et al., 2005 Bioorg Med Chem Lett, 15 |
| Mg$^{2+}$ | | 2-benzylpyrridine-substituted aryloxypropanols | Yang et al., 2005 Bioorg Med Chem Lett, 15 |
| Neomycin and other aminoglycosides | Quinn et al., 1997 Am J Physiol, 273 | Calhex 231 | Petrel et al., 2003 J Biol Chem., 278 |
| spermine | | 2-methyl-3-phenethyl-3H-pyrimidin-4-ones | Shcherbakova et al., 2005 Bioorg Med Chem Lett, 15 |
| | | N(1)-Arylsulfonyl-N(2)-(1-(1-naphthyl)ethyl)-1,2-diaminocyclohexane | Kessler et al., 2004, Chembiochem., 5 |
| | | NPS 2143 | Nemeth et al., 2001 J Pharmacol Exp Ther., 299 |

FIG. 16J

Chemokine CCR1 receptors

| Agonists | references | Antagonists | References |
|---|---|---|---|
| BP-CCL3 | Zoffmann et al., 2001, J Med Chem, 44 | BX 471 | Liang et al., 2000, J Biol Chem, 275 |
| CCL14 | Chou et al., 2002, Br J Pharmacol, 137 | | |
| CCL15 | Coulin et al., 1997, Eur J Biochem, 248 | vMIP-II | Kledal et al., 1997, Science, 277 |
| [$^{125}$I]CCL2 | Sarau et al., 1997, J Pharmacol Exp Ther, 283 | | |
| CCL23 | | | |
| CCL3 | Chou et al., 2002, Br J Pharmacol, 137 | | |
| CCL4 | | | |
| CCL5 | Combadiere et al., 1995, J Biol Chem, 270 | | |
| CCL7 | Chou et al., 2002, Br J Pharmacol, 137 | | |
| [$^{125}$I]CCL8 | Gong et al., 1997, J Biol Chem, 272 | | |
| Flu-CCL3 | Zoffmann et al., 2001, J Med Chem, 44 | | |
| MIP-1δ | Chou et al., 2002, Br J Pharmacol, 137 | | |

FIG. 16K

Dopamine D2 receptor

| Agonists | References | Antagonists | References |
|---|---|---|---|
| 6,7-ADTN | | (+)-butaclamol | |
| apomorphine | | chlorpromazine | |
| bromocriptine | | clozapine | |
| Dopamine | Lajiness et al., 1993, J. Pharmacol. Exp. Ther., 267 | domperidone | |
| lisuride | Sautel et al., 1995, Neuroreport, 6 | fluphenazine | |
| (-)-N-propylnorapo-morphine | | haloperidol | |
| 7-OH-DPAT | Eorge et al., 1995, Endocrinology, 117 | nemonapride | Eorge et al., 1995, Endocrinology, 117 |
| pergolide | | spiperone | |
| PD128907 | | S-sulpiride | |
| quinelorane | | | |
| quinpirole | | | |

FIG. 16L

Dopamine D3 receptor

| Agonists | References | Antagonists | References |
|---|---|---|---|
| apomorphine | | U99194A | Waters et al., 1993 J. Neural Transm. Gen. Sect., 94 |
| BP 897 | | nafadotride | Sautel et al., 1995 J. Pharmacol. Exp. Ther., 275 |
| bromocriptine | Sautel et al., 1995 Neuroreport, 6 | | |
| Dopamine | | | |
| 7-OHDPAT | Chio et al., 1994 J. Biol. Chem., 269 | | |
| PD128907 | | | |
| pramipexole | | | |
| quinelorane | | | |
| quinpirole | | | |

FIG. 16M

Dopamine D4 receptor

| Agonists | References | Antagonists | References |
|---|---|---|---|
| (-)-apomorphine | | CP293019 | Sanner et al., 1998 Bioorg. Med. Chem., 8 |
| bromocriptine | | | |
| di-propyl-ADTN | Chio et al., 1994 J. Biol. Chem., 269 | L745870 | Bristow et al., 1997 Trends Pharmacol. Sci., 18 |
| dopamine | | NGD941 | Tallman et al., 1997 J. Pharmacol. Exp. Ther., 282 |
| lisuride | | | |
| pergolide | Newman-Tancredi et al., 1997 J. Pharmacol. Exp. Ther., 282 | U101387 | Merchant et al., 1996 J. Pharmacol. Exp. Ther., 279 |
| piribedil | | YM50001 | Hidaka et al., 1995 Neuroreport, 7 |
| quinelorane | | clozapine | |
| quinpirole | | | |

FIG. 16N

| Frizzled FZD2 receptor | |
|---|---|
| Agonists | references |
| WNT-5A | Ma and Wang, 2007 *J Biol Chem*, 282 |

| Frizzled SMO receptor | |
|---|---|
| Agonists | references |
| Oxysterols | Corcoran and Scott 2006 *Proc Natl Acad Sci U S A*. 103 |

| Free fatty acid FFA2 receptor | |
|---|---|
| Agonists | References |
| acetate | Nilsson et al., 2003 *Biochem Biophys Res Commun*, 303 |
| butyrate | Le Poul et al., 2003 *J Biol Chem*, 278 |
| isobutyrate | Brown et al., 2003 *J Biol Chem*, 278 |
| pentanoate | Le Poul et al., 2003 *J Biol Chem*, 278 |
| propionate | |

| Free fatty acid FFA3 receptor | |
|---|---|
| Agonists | References |
| acetate | Brown et al., 2003 *J Biol Chem*, 278 |
| butyrate | |
| isobutyrate | Xiong et al., 2004 *Proc Natl Acad Sci*. 101 |
| pentanoate | |
| propionate | |

NB: Currently no antagonists are known for FZD2, SMO, FFA2 or FFA3

FIG. 16O

GABAB receptor

| Agonists | References | Antagonists | References |
|---|---|---|---|
| (-)-baclofen | | CGP 35348 | Froestl et al., 1995 *J. Med. Chem.*, 38, |
| APPA | | CGP 54626A | |
| CGP 47656 | Kaupmann et al., 1997 *Nature*, 386 | CGP 56999A | |
| GABA | | CGP 62349 | |
| | | CGP 64213 | Kaupmann et al., 1997 *Nature*, 386 |
| | | [$^{125}$I]-CGP 64213 | |
| | | CGP 71872 | |
| | | [$^{125}$I]-CGP 71872 | |
| | | 2-OH-saclofen | |
| | | aclofen | |
| | | SCH 50911 | Bolser et al., 1995 *J Pharmacol Exp Ther.*, 274 |

FIG. 16P

Histamine H3 receptor

| Agonists | References | Antagonists | References |
|---|---|---|---|
| (R)-α-methylhistamine | Lovenberg et al., 2000 *J Pharmacol Exp Ther*, 293 | 4-(3-piperdin-1-yl-propoxy)benzonitrile | Liu et al., 2001 *Mol Pharmacol*, 59, |
| (S)-α-methylhistamine | Wulff et al., 2002 *Eur J Pharmacol*, 453 | 1-[4-(3-piperidin-1-yl propoxy)benzyl]piperidine | Apodaca et al., 2003 *J Med Chem*, 46 |
| N-[³H]α-methylhistamine | Chen et al., 2003 *Eur J Pharmacol*, 467 | A-304121, A-317920, ABT-239 | Esbenshade et al., 2004 *Biochem Pharmacol*, 68 |
| N-α-methylhistamine dimaprit | Liu et al., 2001 *Mol Pharmacol*, 59, | Burimamide, | Liu et al., 2001 *Mol Pharmacol*, 59, |
| GR 175737, Perceptin®, proxyfan | Wulff et al., 2002 *Eur J Pharmacol*, 453 | ciproxifan | Rouleau et al., 2004 *J Neurochem*, 90 |
| histamine | Chen et al., 2003 *Eur J Pharmacol*, 467 | Clobenpropit, clozapine | Lovenberg et al., 2000 *J Pharmacol Exp Ther*, 293 |
| Imbutamine, iodoproxyfan | Kitbunnadaj et al., 2003 *J Med Chem*, 46, | FUB 349, FUB 465, GT 2394 | Ligneau et al., 2000 *Br J Pharmacol*, 131 |
| imetit | Rouleau et al., 2004 *J Neurochem*, 90 | Impentamine, iodophenpropit | Wieland et al., 2001 *J Pharmacol Exp Ther*, 299 |
| immepip | Liu et al., 2001 *Mol Pharmacol*, 59, | [³I]iodoproxyfan, proxyfan | Ligneau et al., 2000 *Br J Pharmacol*, 131 |
| Impentamine, methimepip | Kitbunnadaj et al., 2003 *J Med Chem*, 46, | JB 98064 thioperamide | Wulff et al., 2002 *Eur J Pharmacol*, 453 |
| impromidine | Liu et al., 2001 *Mol Pharmacol*, 59, | VUF 4904 | Wieland et al., 2001 *J Pharmacol Exp Ther*, 299 |
| VUF 5207 | Wieland et al., 2001 *J Pharmacol Exp Ther*, 299 | | |

FIG. 16Q

Histamine H4 receptor

| Agonists | References | Agonists | References |
|---|---|---|---|
| 2-(3-bromophenyl)histamine | Lim et al., 2005 J Pharmacol Exp Ther, 314 | burimamide | Liu et al., 2001 J Pharmacol Exp Ther, 299 |
| (R)-α-methylhistamine | Liu et al., 2001 J Pharmacol Exp Ther, 299 | 5-chloroindole-2-piperazinecarboximide | Terzioglu et al., 2004 Bioorg Med Chem Lett, 14 |
| (S)-α-methylhistamine | Morse et al., 2001 J Pharmacol Exp Ther, 296 | ciproxifan | Esbenshade et al., 2004 Biochem Pharmacol, 68, |
| N-α-methylhistamine | | clobenpropit | |
| CCL16 | Nakayama et al., 2004 J Immunol, 173, | clozapine | Liu et al., 2001 J Pharmacol Exp Ther, 299 |
| dimaprit | Liu et al., 2001 Mol Pharmacol, 59 | iodophenpropit | Zhu et al., 2001 Mol Pharmacol, 59 |
| Histamine, imetit | Liu et al., 2001 J Pharmacol Exp Ther, 299 | JNJ 7777120 | Thurmond et al., 2004 J Pharmacol Exp Ther, 309 |
| HTMT | | [³H]pyrilamine | Nguyen et al., 2001 Mol Pharmacol, 59 |
| immepip | Zhu et al., 2001 Mol Pharmacol, 59 | thioperamide | Liu et al., 2001 J Pharmacol Exp Ther, 299 |
| improgan | | | |
| impromidine | Lim et al 2005 J, Pharmacol Exp Ther, 314 | | |
| methimepip | Kitbunnadaj et al., 2005 J Med Chem, 48, | | |
| methylhistamine | Lim et al 2005 J, Pharmacol Exp Ther, 314 | | |
| VUF 8430 | Lim et al., 2006 J Med Chem, 49 | | |

FIG. 16R

| Leukotriene BLT1 receptor | | | |
|---|---|---|---|
| Agonists | References | Antagonists | References |
| 20-COOH-LTB₄ | Devchand et al., 1996 Nature, 384 | U75302 | Devchand et al., 1996 Nature, 384 |
| 12R-HETE | | | |
| 12-keto-LTB₄ | | | |
| 20-OH-LTB₄ | | | |
| LTB₄ | | | |

FIG. 16S

Melatonin MT1 receptor

| Agonists | References | Antagonists | References |
|---|---|---|---|
| 2-[125I]MLT | Audinot et al., 2003 Naunyn Schmiedebergs Arch Pharmacol, 367 | 4P-PDOT | Audinot et al., 2003 Naunyn Schmiedebergs Arch Pharmacol, 367 |
| agomelatine | | | |
| 6-Cl-MLT | | K185 | Faust et al., 2000 J Med Chem, 43 |
| GR 128107 | Teh and Sugden 1999, Br J Pharmacol, 126 | | |
| GR 196429 | Browning et al., 2000 Br. J. Pharmacol., 129 | | |
| 5-HEAT | Nonno et al., 2000 J Pineal Res, 29, 23 | luzindole | |
| 2-I-MLT | Audinot et al., 2003 Naunyn Schmiedebergs Arch Pharmacol, 367 | | |
| IIK7 | Faust et al., 2000 J Med Chem, 43 | S20928 | Audinot et al., 2003 Naunyn Schmiedebergs Arch Pharmacol, 367 |
| LY 156735 | Mulchahey et al., 2004 Life Sci, 75 | | |
| [3H]MLT | | | |
| 6-OH-MLT | Browning et al., 2000 Br. J. Pharmacol., 129 | S22153 | |
| S24014 | Audinot et al., 2003 Naunyn Schmiedebergs Arch Pharmacol, 367 | S26131 | |
| S24773 | | | |
| S26284 | | | |
| TAK375 | Kato et al., 2005 Neuropharmacology, 48 | | |

FIG. 16T

Metabotropic glutamate mGlu2 receptor

| Agonists | References |
|---|---|
| (1S,3R)-ACPD | Johnson et al., 1999 Neuropharmacology., 38 |
| (2R,3R)-APDC | Cartmell et al., 1998 Br J Pharmacol., 123 |
| (S)-4C3HPG | |
| DCG-IV | Johnson et al., 1999 Neuropharmacology., 38 |
| L-CCG-I | |
| L-glutamate | Schweitzer et al., 2000 Neuropharmacology., 39, |
| [³H]LY35740 | |
| LY379268 | Monn et al., 1999 J Med Chem., 42, |
| MGS0028 | Nakazato et al., 2000 J Med Chem, 43 |

| Antagonists | References |
|---|---|
| eGlu | Schweitzer et al., 2000 Neuropharmacology., 39 |
| LY341495 | Johnson et al., 1999 Neuropharmacology., 38 |
| [³H]LY341495 | |
| (+)-MCPG | Cartmell et al., 1998 Br J Pharmacol., 123 |
| MGS0039 | Chaki et al., 2004 Neuropharmacology, 46 |
| MSOP | Cartmell et al., 1998 Br J Pharmacol., 123 |

FIG. 16U

Metabotropic glutamate mGlu3 receptor

| Agonists | References | | Antagonists | References |
|---|---|---|---|---|
| (1S,3R)-ACPD | Johnson et al., 1999 Neuropharmacology., 38 | | eGlu | Schweitzer et al., 2000 Neuropharmacology, 39 |
| (2R,4R)-APDC | | | | |
| DCG-IV | Cartmell et al., 1998 Br J Pharmacol., 123 | | LY341495 | Johnson et al., 1999 Neuropharmacology., 38 |
| L-CCG-I | Johnson et al., 1999 Neuropharmacology., 38 | | | |
| L-glutamate | | | [$^3$H]LY341495 | |
| [$^3$H]LY341495 | Schweitzer et al., 2000 Neuropharmacology., 39 | | (+)-MCPG | Cartmell et al., 1998 Br J Pharmacol., 123 |
| LY354740 | Monn et al., 1999 J Med Chem., 42, | | | |
| LY379268 | | | MGS0039 | Chaki et al., 2004 Neuropharmacology, 46 |
| NAAG | Schweitzer et al., 2000 Neuropharmacology., 39 | | | |

FIG. 16V

Metabotropic glutamate mGlu4 receptor

| Agonists | references | Agonists | References |
|---|---|---|---|
| (R,S)-4-PPG | Gasparini et al., 1999 *J. Pharmacol. Exp. Ther.*, 289 | | |
| (S)-3,4-DCPG | Thomas et al., 2001 *Neuropharmacology.*, 40 | CPPG | Han and Hampson 1999 *J Biol Chem.*, 274 |
| ACPT-I | Acher et al., 1997 *J Med Chem*, 40, | | |
| [³H]AP4 | Han and Hampson 1999 *J Biol Chem.*, 274, | LY341495 | Kingston et al., 1995 *Neuropharmacology.*, 34 |
| FP0429 | Muto et al., 2007 *Proc Natl Acad Sci U S A*, 104 | | |
| L-AP4 | Acher et al., 1997 *J Med Chem*, 40 | MAP4 | Han and Hampson 1999 *J Biol Chem.*, 274 |
| L-CCG-I | Hayashi et al., 1992 *Br J Pharmacol.*, 107 | | |
| L-glutamate | Han and Hampson 1999 *J Biol Chem.*, 274 | MPPG | |
| L-SOP | | | |

FIG. 16W

Metabotropic glutamate mGlu6 receptor

| Agonists | References | Antagonists | References |
|---|---|---|---|
| (1S,3R)-ACPD | Tuckmantel et al., 1997 Bioorg Med Chem Lett., 7 | DCG-IV | Brabet et al., 1998 Neuropharmacology., 37 |
| (1S,3R)-ACPD | Laurie et al., 1997 Neuropharmacology, 36 | | |
| (2S,1S,2S)-L-CCG-I | | [³H]LY341495 | Wright et al., 2000 Naunyn Schmiedebergs Arch Pharmacol., 362 |
| (R,S)-4-PPG | Thomas et al., 2001 Neuropharmacology, 40 | | |
| (S)-3,4-DCPG | | MAP4 | Pin and Acher 2002 Curr Drug Targets CNS Neurol Disord., 1 |
| ACPT-I | | | |
| 1-benzyl-APDC | Uckmantel et al., 1997 Bioorg Med Chem Lett., 7, | | |
| L-AP4 | Laurie et al., 1997 Neuropharmacology, 36 | MPPG | Ma et al., 1997 Bioorg Med Chem Lett., 7, |
| L-glutamate | | | |
| L-SOP | | α-MSOP | Pin and Acher 2002 Curr Drug Targets CNS Neurol Disord., 1 |
| LY354740 | Monn et al., 1999 J Med Chem., 42 | | |
| LY379268 | | | |

FIG. 16X

Metabotropic glutamate mGlu7 receptor

| Agonists | References | Antagonists | References |
|---|---|---|---|
| (1S,3R)-ACPD | Wright et al., 2000 Naunyn Schmiedebergs Arch Pharmacol., 362 | DCG-IV | |
| (R,S)-4-PPG | Gasparini et al., 1999 J. Pharmacol. Exp. Ther., 289 | LY341495 | |
| | | [³H]LY341495 | |
| L-AP4 | | MAP4 | |
| L-CCG-I | | MCCG | |
| L-glutamate | Wright et al., 2000 Naunyn Schmiedebergs Arch Pharmacol., 362 | (+)-MCPG | |
| | | MPPG | Wright et al., 2000 Naunyn Schmiedebergs Arch Pharmacol., 362 |
| L-SOP | | MSOP | |
| PPG | | MSOPPE | |

FIG. 16Y

Metabotropic glutamate mGlu8 receptor

| Agonists | References | Antagonists | References |
|---|---|---|---|
| (1S,3R)-1-ACPD | Wu et al., 1998 Brain Res. Mol. Brain Res., 53, | | |
| (R,S)-4-PPG | Thomas et al., 2001 Neuropharmacology., 40 | CPPG | Peltekova et al., 2000 Brain Res Mol Brain Res, 76 |
| (S)-3,4-DCPG | | | |
| ACPT-I | de Colle et al., 2000 Eur J Pharmacol, 394 | DCG-IV | Malherbe et al., 1999 Brain Res. Mol. Brain Res., 67 |
| [³H]AP4 | Malherbe et al., 1999 Brain Res. Mol. Brain Res., 67 | LY341495 | Kingston et al., 1998 Neuropharmacology., 37 |
| D-AP4 | Wu et al., 1998 Brain Res. Mol. Brain Res., 53 | | |
| L-AP4 | | MAP4 | Peltekova et al., 2000 Brain Res Mol Brain Res, 76 |
| L-AP4 | | | |
| L-CCG-I | | | |
| L-CCG-I | Malherbe et al., 1999 Brain Res. Mol. Brain Res., 67 | α-MSOP | Pin and Acher 2002 Curr Drug Targets CNS Neurol Disord., 1 |
| L-glutamate | | | |
| L-SOP | | | |
| LY354740 | | | |

FIG. 16Z

Neuropeptide W/neuropeptide B receptors

| NPBW1 | | | NPBW2 | | |
|---|---|---|---|---|---|
| Agonists | References | | Agonists | Antagonists | |
| [$^{125}$I][Tyr$^{1}$]des-Br-NPB-23 | | | NPB-23 | | |
| Br-NPB-29 | Fujii et al., 2002 *J Biol Chem.*, 277 | | NPB-29 | Brezillon et al., 2003 *J Biol Chem.*, 278 | |
| des-Br-NPB-23 | | | [$^{125}$I]NPW | | |
| des-Br-NPB-29 | | | NPW-23 | Shimomura et al., 2002 *J Biol Chem.*, 277 | |
| NPW-23 | Shimomura et al., 2002 *J Biol Chem.*, 277 | | NPW-30 | Brezillon et al., 2003 *J Biol Chem.*, 278 | |
| [$^{125}$I]NPW-23 | | | | | |
| NPW-30 | | | | | |

NB: No antagonists are currently available neither for NPBW1 nor for NPBW2

FIG. 16AA

Neuropeptide Y1 receptors

| Agonists | References | Agonists | References |
|---|---|---|---|
| [125I]NPY | Krause et al., 1992 *Mol Pharmacol*, 41 | 1229U91 | Gehlert et al., 1997 *Peptides*, 18 |
| [3H]NPY | Weng et al., 1995 *Mol Pharmacol*, 48 | BIBO3304 | Dumont and Quirion 2000 *Br J Pharmacol*, 129 |
| [Leu31,Pro34]-NPY | Krause et al., 1992 *Mol Pharmacol*, 41 | BIBP3226 | Gehlert et al., 1997 *Peptides*, 18 |
| [Ala31,Aib32]-NPY | Cabrele et al., 2002 *Biochemistry*, 41 | GR231118 | Dumont and Quirion 2000 *Br J Pharmacol*, 129 |
| NPY | Krause et al., 1992 *Mol Pharmacol*, 41 | [125I]GR231118 | |
| NPY2-36 | Gehlert, et al., 1997 *Peptides*, 18 | SR120819A | Sjödin et al., 2006 *Biochem J*, 393 |
| PP (rat) | Larhammar et al., 1992 *J Biol Chem*, 267 | | |
| [125I]PYY | | | |
| PYY | Dumont and Quirion 2000 *Br J Pharmacol*, 129 | | |

FIG. 16BB

| Neuropeptide Y2 receptors | | | |
|---|---|---|---|
| Agonists | References | Antagonists | References |
| N-α-Ac-PYY$_{25-36}$ | Goumain, et al., 2001 Mol Pharmacol, 60 | BIE0246 | Goumain et al., 2001 Mol Pharmacol, 60 |
| C2-NPY | Gerald et al., 1995 J Biol Chem, 270 | | |
| [$^{125}$I]NPY | Rose et al., 1995 J Biol Chem, 270 | | |
| [D-Trp$^{32}$]-NPY | Gehlert et al., 1996 Mol Pharmacol, 49 | | |
| NPY (human) | Gerald et al., 1995 J Biol Chem, 270 | | |
| [Leu$^{31}$,Pro$^{34}$]-NPY | | | |
| [Ala$^{31}$,Aib$^{32}$]-NPY | Cabrele, et al., 2002 Biochemistry, 41 | | |
| NPY$_{13-36}$ (human) | | | |
| NPY$_{16-36}$ (porcine) | | | |
| NPY$_{3-36}$ (porcine) | | | |
| [$^{125}$I]PYY | | | |
| PYY (human) | Gerald et al., 1995 J Biol Chem, 270 | | |
| [Leu$^{31}$,Pro$^{34}$]-PYY (human) | | | |
| [Pro$^{34}$]-PYY (human) | | | |
| PYY (porcine) | | | |
| PYY$_{13-36}$ (porcine) | | | |

FIG. 16CC

Neuropeptide Y4 receptors

| Agonists | References | Antagonists | References |
|---|---|---|---|
| GR231118 | Tough et al., 2006, *J Pharmacol Exp Ther*, 319 | 1229U91 | Gehlertet al., 1997 *Peptides*, 18 |
| NPY, [Leu$^{31}$,Pro$^{34}$]-NPY | Gregor et al., 1996, *FEBS Lett*, 381 | | |
| [Ala$^{31}$,Aib$^{32}$]-NPY | Cabrele et al., 2002 *Biochemistry*, 41 | | |
| NPY$_{13-36}$ | | | |
| NPY$_{2-36}$ | Lundell et al., 1995 *J Biol Chem*, 270 | | |
| PP | Walker et al., 1997 *Peptides*, 18 | | |
| [Ile$^{31}$,Gln$^{34}$]-PP | | | |
| PP$_{20-36}$ | | | |
| PYY | Gregor et al., 1996, *FEBS Lett*, 381 | | |
| [Leu$^{31}$,Pro$^{34}$]-PYY | Dumont and Quirion 2000 *Br J Pharmacol*, 129 | | |
| [Leu$^{31}$,Pro$^{34}$]-PYY | Gehlert et al., 1997 *Peptides*, 18 | | |
| [Pro$^{34}$]-PYY | Tough et al., 2006 *J Pharmacol Exp Ther*, 319 | | |
| [$^{125}$I]PYY | Lundell et al., 1995 *J Biol Chem*, 270, | | |
| PYY$_{3-36}$ (human) | Walker et al., 1997 *Peptides*, 18 | | |

FIG. 16DD

Neuropeptide Y5 receptors

| Agonists | References | Antagonists | References |
|---|---|---|---|
| [$^{125}$I][PP$_{1-17}$,Ala$^{31}$,Aib$^{32}$]-NPY | Dumont et al., 2003 *Br J Pharmacol*, 139 | CGP 71683A | Dumont et al., 2003 *Br J Pharmacol*, 139 |
| GR231118 | | | |
| [Ala$^{31}$,Aib$^{32}$]-NPY | Hu et al., 1996 *J Biol Chem*, 271 | FMS586 | Kakui et al., 2006 *J Pharmacol Exp Ther*, 317 |
| [D-Trp$^{32}$]-NPY | | | |
| [PP$_{1-17}$,Ala$^{31}$,Aib$^{32}$]-NPY | Cabrele et al., 2002 *Biochemistry*, 41 | JCF 109 | Dumont et al., 2003 *Br J Pharmacol*, 139 |
| NPY | | | |
| [Ala$^{31}$,Aib$^{32}$]-NPY | | [Leu$^{31}$,Pro$^{34}$]-NPY | L-152,804 | Kanatani et al., 2000 *Biochem Biophys Res Commun*, 272 |
| NPY$_{2-36}$ | Hu et al., 1996 *J Biol Chem*, 271 | L-152,804 | |
| PP | | | |
| PYY | | | |
| PYY$_{3-36}$ | | | |

FIG. 16EE

| Neuropeptide FF/neuropeptide AF receptors | | | |
|---|---|---|---|
| NPFF1 | | | |
| Agonists | References | Antagonists | References |
| 1DMe | | BIBP3226 | Mollereau et al., 2002 *Eur J Pharmacol*, 451 |
| [$^{125}$I]1DMe | | | |
| EFWSLAAPQRF-NH$_2$ | Bonini et al., 2000 *J Biol Chem*, 275 | | |
| NPFF | Gouardères et al., 2002 *Neuroscience*, 115, | | |
| PP (frog) | | | |
| RFRP-3 (human) | Mollereau et al., 2002 *Eur J Pharmacol*, 451 | | |
| Y-RFRP-3 | | RF9 | Simonin et al., 2006, *Proc Natl Acad Sci U S A*, 103 |
| [$^{125}$I]Y-RFRP-3 | | | |

FIG. 16FF

| Neuropeptide FF/neuropeptide AF receptors | | | |
|---|---|---|---|
| NPFF2 | | | |
| Agonists | References | Antagonists | References |
| 1DMe | Gouardères et al., 2002 *Neuroscience*, 115, | BIBP3226 | Mollereau et al., 2002 *ur J Pharmacol*, 451 |
| dNPA | Quelven et al., 2005 *Eur J Pharmacol*, 508 | | |
| EFWSLAAPQRF-NH$_2$ | Mollereau et al., 2002 *Eur J Pharmacol*, 451 | | |
| NPFF | Mollereau et al., 2001 *Br J Pharmacol*, 133 | | |
| PP (frog) | | | |
| RFRP-3 (human) | Mollereau et al., 2002 *Eur J Pharmacol*, 451 | RF9 | Simonin et al., 2006, *Proc Natl Acad Sci U S A*, 103 |
| YVPNLPQRF-NH$_2$ | | | |

FIG. 16GG

Nicotinic acid receptor family

GPR81

| Agonists | references |
|---|---|
| Nicotinic acid | Wise et al., 2003 J Biol Chem, 278 |

GPR109A

| Agonists | References |
|---|---|
| (+)-5-(5-bromothiophen-3-yl)-5-methyl-4-oxo-4,5-dihydro-furan-2-carboxylic acid | Taggart et al., 2005 J Biol Chem, 280 |
| D-β-hydroxybutyrate | |
| acifran | |
| acipimox | Wise et al., 2003 J Biol Chem, 278 |
| 5-butyl-1H-pyrazole-3-carboxylic acid | van Herk et al., 2003 J Med Chem, 46 |
| 5-methyl nicotinic acid | |
| nicotinic acid | Wise et al., 2003 J Biol Chem, 278 |
| [³H]nicotinic acid | |
| 3-pyridine-acetic acid | |

GPR109B

| Agonists | References |
|---|---|
| acifran | |
| 5-ethyl-4-oxo-5-phenyl-4,5-dihydro-furan-2-carboxylic acid | Jung et al., 2007 J Med Chem, 50 |
| 1-isopropylbenzotriazole-5-carboxylic acid | Semple et al., 200 6 J Med Chem, 49 |
| 5-methyl-5-(5-methyl-triophen-3-yl)-4-oxo-2-4,5-dihydro-furan-2-carboxylic acid | Jung et al., 2007 J Med Chem, 50 |
| nicotinic acid | Wise et al., 2003 J Biol Chem, 278 |

NB: Currently no antagonists are known for GPR81, GPR109A or GPR109B

FIG. 16HH

Opioid δ Receptor

| Agonists | References | Antagonists | References |
|---|---|---|---|
| β endorphin, | | (-)-naloxone | |
| (-)-bremazocine | | | |
| (-)-cyclazocine | | (-)-quadazocine | |
| (-)-EKC | | | |
| (-)-pentazocine | | BNTX | Toll et al., 1998 |
| DADLE | | | *NIDA Res Monogr*, 178 |
| deltorphin II | Raynor et al., 1994 | CTAP | |
| dihydromorphine | *Mol Pharmacol*, 45 | | |
| diprenorphine | | β-FNA | Yasuda et al., 1993 |
| [³H]diprenorphine | Toll et al., 1998 | | *Proc. Natl. Acad. Sci.*, 90 |
| DPDPE | *NIDA Res Monogr*, 178 | | |
| DSLET | | ICI 174,864 | Neilan et al., 1999 |
| dynorphin 1-11 | Yasuda et al., 1993 | | *Br J Pharmacol*, 128, |
| dynorphin 1-13 | *Proc. Natl. Acad. Sci.*, 90 | | |
| dynorphin 1-17 | | naloxone | Raynor et al., 1994 |
| dynorphin 1-8 | Gong et al., 1998 | | *Mol Pharmacol*, 45 |
| dynorphin B | *FEBS Lett*, 439 | naltrexone | |
| EKC | | | |
| endomorphin-1 | Quock et al., 1997 | naltriben | |
| [Leu]-enkephalin | *Eur J Pharmacol*, 326 | | |
| [Met]-enkephalin | | naltrindole | |
| etonitazene | | | |
| etorphine | | nor-binaltorphimine | |
| fentanyl | | | |
| morphine | | TIPPψ | |
| nalmefene | | | |
| nalorphine | | | |
| α-neoendorphin | | | |
| normorphine | | | |
| SNC80 | | | |

FIG. 16II

Opioid κ receptor

| Agonists | References | Antagonists | References |
|---|---|---|---|
| β endorphin (human) | | (−)-naloxone | Toll et al., 1998 *NIDA Res Monogr*, 178 |
| (±)-EKC | | (−)-quadazocine | |
| (−)-bremazocine | | BNTX | Yasuda et al., 1993 *Proc. Natl. Acad. Sci.*, 90 |
| (−)-cyclazocine | Toll et al., 1998 *NIDA Res Monogr*, 178 | buprenorphine | |
| (−)-EKC | | diprenorphine | Simonin et al., 1995 *Proc Natl Acad Sci* 92 |
| (−)-methadone | Zhu et al., 1997 *J Pharmacol Exp Ther*, 282 | [³H]diprenorphine | |
| (−)-pentazocine | | β-FNA | Jones and Portoghese 2000 *Eur J Pharmacol*, 396 |
| bremazocine | Yasuda et al., 1993 *Proc. Natl. Acad. Sci.*, 90 | GNTI | |
| CI 977 | | nalmefene | |
| DAMGO | Hjorth et al., 1996 *Mol Pharmacol*, 50 | (+)-naloxone | Chen et al., 1993 *Biochem J*, 295 |
| dihydromorphine | Meng et al., 1993 *Proc Natl Acad Sci* 90 | naltrexone | |
| dynorphin 1-11 | | naltriben | |
| dynorphin 1-13 | Neumeyer et al., 2003 *J Med Chem*, 46 | naltrindole | |
| dynorphin 1-13 | | nor-binaltorphimine | |
| [D-Ala²,F₅,Phe⁴]-dynorphin 1-13-NH₂ | | | |
| dynorphin 1-17 | | | |
| [Met⁵]-dynorphin 1-17 | | | |
| dynorphin 1-17-NH₂ | | | |
| [D-Ala²,F₅,Phe⁴]-dynorphin 1-17-NH₂ | | | |
| dynorphin 1-8 | | | |
| dynorphin B | | | |
| E2078 | | | |
| EKC | | | |
| enadoline | | | |
| [Leu]-enkephalin | | | |
| [Met]-enkephalin | | | |
| etorfitazene | | | |
| etorphine | | | |
| fentanyl | | | |
| GR 89696 | | | |

FIG. 16JJ

| Opioid K receptor | |
|---|---|
| Agonists | References |
| ICI 204448 | |
| morphine | |
| nalorphine | |
| naloxone benzoylhydrazone | Toll et al., 1998<br>*NIDA Res Monogr*, 178 |
| α-neoendorphin | Zhu et al., 1997 *J Pharmacol Exp Ther*, 282 |
| β-neoendorphin | |
| normorphine | Yasuda et al., 1993<br>*Proc. Natl. Acad. Sci.*, 90 |
| pentazocine | Hjorth et al., 1996<br>*Mol Pharmacol*, 50 |
| salvinorin A | Meng et al., 1993<br>*Proc Natl Acad Sci* 90 |
| tifluadom | Neumeyer et al., 2003<br>*J Med Chem*, 46 |
| TRK820 | |
| U50488<br>U63640<br>U69593 | |
| [$^3$H]U69593 | |

FIG. 16KK

Opioid μ receptor

| Agonists | References | Antagonists | References |
|---|---|---|---|
| β endorphin | | (-)-bremazocine | |
| (-)-cyclazocine | | (-)-naloxone | |
| (-)-EKC | | (-)-naloxone | |
| (-)-methadone | | (-)-quadazocine | |
| (-)-pentazocine | | BNTX | |
| buprenorphine | | CTAP | |
| codeine | | CTOP | |
| DADLE | | diprenorphine | |
| DAMGO | Raynor et al., 1994 Mol Pharmacol, 45 | diprenorphine | Raynor et al., 1994 Mol Pharmacol, 45 |
| [tyrosyl 3,5-$^3$H]DAMGO | | [15,16-$^3$H]diprenorphine | |
| dihydromorphine | | β-FNA | |
| DSLET | Toll et al., 1998 NIDA Res Monogr, 178 | β-FNA | Toll et al., 1998 NIDA Res Monogr, 178 |
| dynorphin 1-11 | | nalmefene | |
| dynorphin 1-13 | | nalorphine | |
| dynorphin 1-17 | | naloxonazine | |
| dynorphin 1-8 | Gong et al., 1998 FEBS Lett, 439 | [N-allyl-2,3-$^3$H]naloxone | |
| dynorphin B | | naloxone | |
| endomorphin-1 | | benzoylhydrazone | |
| [Leu]-enkephalin | | naloxone | |
| [Met]-enkephalin | | benzoylhydrazone | |
| etonitazene | | naltrexone | |
| etorphine | | naltriben | |
| fentanyl | | naltrindole | |
| morphine | | nor- | |
| normorphine | | binaltorphimine | |
| PL017 | | | |

FIG. 16LL

| Opioid NOP receptor | | | |
|---|---|---|---|
| Agonists | References | Antagonists | References |
| [³H]14-Tyr-N/OFQ | Adapa and Toll 1997 Neuropeptides, 31 | | |
| Ac-RYYRIK-NH₂/SUB<id> | McDonald et al., 2003 Br J Pharmacol, 140, | J-113397 | Ozaki et al., 2000 Eur J Pharmacol, 402 |
| Ac-RYYRIK-NH₂ | Dooley et al., 1997 J Pharmacol Exp Ther, 283 | JTC-801 | Shinkai et al., 2000 J Med Chem, 43 |
| Ac-RYYRWK-NH₂ | McDonald et al., 2003 Br J Pharmacol, 140 | | |
| Ac-RYYRWK-NH₂ | Okada et al., 2000 Biochem Biophys Res Commun, 278 | [Nphe¹]N/OFQ(1-13)NH₂ | Calo et al., 2002 Br J Pharmacol, 136 |
| N/OFQ | Enck et al., 2000 Proc Natl Acad Sci 97 | peptide III-BTD | Becker et al., 1999 J Biol Chem, 274 |
| N/OFQ | Carrà et al., 2005 J Pharmacol Exp Ther, 312 | SB 612111 | Zaratin et al., 2004 J Pharmacol Exp Ther, 308 |
| [³H]N/OFQ | | | |
| [Arg¹⁴Lys¹⁵]N/OFQ | | | |
| N/OFQ(1-13)NH₂ | | | |
| [(pF)Phe⁴]N/OFQ(1-13)NH₂ | | | |
| [F/G]N/OFQ(1-13)NH₂ | | UFP-101 | Calo et al., 2002 Br J Pharmacol, 136 |
| N/OFQ-NH₂ | | | |
| Ro64-6198 | | | |
| UFP-102 | | | |

FIG. 16MM

Orexin OX1 receptor

| Agonists | references | Antagonists | References |
|---|---|---|---|
| Orexin-A | Langmead et al., 2004 Br J Pharmacol, 141 | 1-(2,4-dibromo-phenyl)-3-((4S,5S)-2,2-dimethyl-4-phenyl-[1,3]dioxan-5-yl)-urea | McAtee et al., 2004 Bioorg Med Chem Lett, 14 |
| Orexin-A 2-33 | Lang et al., 2004 J Med Chem, 47 | 1-(2-bromo-phenyl)-3-((4S,5S)-2,2-dimethyl-4-phenyl-[1,3]dioxan-5-yl)-urea | |
| Orexin-B | Langmead et al., 2004 Br J Pharmacol, 141 | SB-334867 | Porter et al., 2001 Bioorg Med Chem Lett, 11 |
| | | SB-408124 | |
| [Ala$^{11}$, D-Leu$^{11}$]Orexin-B | Asahi et al., 2003 Bioorg Med Chem Lett, 13 | SB-410220 | Langmead et al., 2004 Br J Pharmacol, 141 |
| | | [$^3$H]SB-674042 | |

FIG. 16NN

| P2Y12 receptor | | | |
|---|---|---|---|
| Agonists | References | Antagonists | References |
| 2MeSADP | Herbert and Savi 2003 *Semin Vasc Med*, 3 | 2MeSAMP | Takasaki et al., 2001 *Mol Pharmacol*, 60 |
| [³H]2MeSADP | Takasaki et al., 2001 *Mol Pharmacol*, 60 | active metabolite of clopidogrel | Herbert and Savi 2003 *Semin Vasc Med*, 3 |
| 2MeSATP | Herbert and Savi 2003 *Semin Vasc Med*, 3 | AR-C69931MX | Takasaki et al., 2001 *Mol Pharmacol*, 60 |
| ADP | | | |
| ADPβS | Takasaki et al., 2001 *Mol Pharmacol*, 60 | pCMPS | Herbert and Savi 2003 *Semin Vasc Med*, 3 |
| ATP | Herbert and Savi 2003 *Semin Vasc Med*, 3 | | |
| ATPγS | | | |

FIG. 16OO

P2Y13 receptor

| Agonists | References |
|---|---|
| 2MeSADP | |
| [33P]2MeSADP | |
| 2MeSATP | Marteau et al., 2003 *Mol Pharmacol*, 64, |
| ADP | |
| ADPβS | |
| ATP | |
| ATPγS | |

| Antagonists | References |
|---|---|
| 2MeSAMP | |
| Ap₄A | |
| AR-C67085MX | Marteau et al., 2003 *Mol Pharmacol*, 64, |
| AR-C69931MX | |
| PPADS | |
| reactive blue 2 | |
| suramin | |

P2Y14 receptor

| Agonists | References |
|---|---|
| UDP-glucose | Freeman et al., 2001 *Genomics*, 78 |
| UDP-glucuronic acid | |
| UDP-N-acetylglucosamine | |

NB: No antagonists are known for P2Y14

FIG. 16PP

Prostanoid DP2 receptors

| Agonists | References |
|---|---|
| Δ$^{12}$-PGJ$_2$ | |
| 13,14-dihydro-15-keto-PGD$_2$ | |
| 13,14-dihydro-15-keto-PGF$_{2α}$ | |
| 15(R)-15-methyl-PGD$_2$ | Sawyer et al., 2002 *Br J Pharmacol*, 137 |
| 15(S)-15-methyl-PGD$_2$ | Hata et al., 2003 *J Pharmacol Exp Ther*, 306 |
| 15-deoxy-Δ$^{12,14}$-PGD$_2$ | Ulven and Kostenis 2005 *J Med Chem*, 48 |
| 15-deoxy-Δ$^{12,14}$-PGJ$_2$ | |
| CAY 10471 | |
| indomethacin | |
| L-883,595 | Gervais et al., 2005 *Mol Pharmacol*, 67 |
| L-888,291 | |
| L-888,607 | Shichijo et al., 2003 *J Pharmacol Exp Ther*, 307 |
| PGD$_2$ | |
| [$^3$H]PGD$_2$ | |
| PGD$_3$ | |
| PGE$_2$ | |
| PGF$_{2α}$ | |
| PGJ$_2$ | |
| U46619 | |

| Antagonists | References |
|---|---|
| ramatroban | Hata et al., 2005 *J Biol Chem*, 280 |
| [$^3$H]ramatroban | Sugimoto et al., 2005 *Eur J Pharmacol*, 524 |

FIG. 16QQ

Serotonin 5-HT1A receptor

| Agonists | References | Antagonists | References |
|---|---|---|---|
| (−)-quinpirole | | (−)-propranolol | |
| apomorphine | | (−)-tertatolol | |
| aripiprazole | | (R)-flurocarazolol | Newman-Tancredi et al., 1997 Naunyn Schmiedebergs Arch Pharmacol, 355 |
| BMY-14802 | Newman-Tancredi et al., 1999 Naunyn Schmiedebergs Arch Pharmacol, 359 | (S)-flurocarazolol | |
| BMY-7378 | | [$^3$H]-p-MPPF | Newman-Tancredi et al., 1998 Eur J Pharmacol, 355 |
| BRL-15572 | Millan et al., 2002 J Pharmacol Exp Ther, 303 | p-MPPI | |
| bromocriptine | | (+)-butaclamol | |
| buspirone | Shapiro et al., 2003 Neuropsychopharmacology, 28 | chlorpromazine | Roth et al., 2001 Psychopharmacology (Berl), 157 |
| cabergoline | | cyamemazine | |
| clozapine | | fluspirilene | |
| CP 93129 | Newman-Tancredi et al., 1998 Eur J Pharmacol, 355 | GR 125,743 | Kalipatnapu et al., 2004 Biosci Rep, 24 |
| 5-CT | | GR 218,231 | |
| donitriptan | Khawaja et al., 1997 Life Sci, 60 | haloperidol | |
| eletriptan | | iloperidone | Hameg et al., 2003 Biochem Pharmacol, 65 |
| EMDT | Price et al., 1997 Naunyn Schmiedebergs Arch Pharmacol., 356 | iloperidone | |
| FG-5893 | | ketanserin | Schotte et al., 1996 Psychopharmacology (Berl), 124 |
| (+)-flesinoxan | Newman-Tancredi et al., 1992 Biochem J, 285 | methiothepin | |
| fluparoxan | | MPDT | Millan et al., 2000 J Pharmacol Exp Ther, 293 |
| GR-127935 | | NAD 299 | |
| 5-HT | | [$^3$H]NAD 299 | |

FIG. 16RR

Serotonin 5-HT1A receptor

| Agonists | References | Antagonists | References |
|---|---|---|---|
| ipsapirone | | NAN 190 | |
| L-694,247 | | 9-OH-risperidone | |
| L-772,405 | | pimozide | |
| lisuride | Millan et al., 2002 *J Pharmacol Exp Ther*, 303 | pindolol | Newman-Tancredi et al., 1997 *Naunyn Schmiedebergs Arch Pharmacol*, 355 |
| LSD | Newman-Tancredi et al., 1998 *Eur J Pharmacol*, 355 | pipamperone | |
| LY293284 | | pizotifen | |
| LY334370 | Newman-Tancredi et al., 1992 *Biochem J*, 285 | raclopride | Kalkman et al., 2001 *Neuropsychopharmacology*, 25 |
| LY344864 | | Rec 15/3079 | |
| 7-methoxy-1-naphthylpiperazine | John et al., 1999 *J Pharmacol Exp Ther*, 290 | repinotan | |
| nafadotride | | risperidone | Kongsamut et al., 1996 *Eur J Pharmacol*, 317 |
| 1-naphthylpiperazine | | risperidone | |
| naratriptan | Napier et al., 1999 *Eur J Pharmacol*, 368 | ritanserin | |
| ocaperidone | | SB 272183 | Newman-Tancredi et al., 1992 *Biochem J*, 285 |
| 8-OH-DPAT | Millan et al., 2000 *Synapse*, 35 | SB 649915 | |
| [³H]8-OH-DPAT | | SB 714786 | Newman-Tancredi et al., 1998 *Eur J Pharmacol*, 355 |
| olanzapine | | SDZ-216525 | |
| ORG-5222 | | sertindole | |
| PAPP | | spiperone | |
| pergolide | | thioridazine | |

FIG. 16SS

Serotonin 5-HT1A receptor

| Agonists | References | Antagonists | References |
|---|---|---|---|
| piribedil | | tiospirone | |
| quetiapine | Millan et al., 2002 *J Pharmacol Exp Ther*, 303 | | |
| rizatriptan | | | |
| roxindole | | (+)-UH 301 | Newman-Tancredi et al., 1998 *Eur J Pharmacol*, 355 |
| RU 24969 | Newman-Tancredi et al., 1998 *Eur J Pharmacol*, 355 | | |
| S-14506 | | WAY-100135 | Millan et al., 2000 *Synapse*, 35 |
| S-14671 | Newman-Tancredi et al., 1992 *Biochem J*, 285 | | |
| S-15535 | | WAY-100635 | Newman-Tancredi et al., 1998 *Naunyn Schmiedebergs Arch Pharmacol*, 357 |
| [³H]S-15535 | | | |
| S-16924 | | yohimbine | Schotte et al., 1996 *Psychopharmacology (Berl)*, 124 |
| SB 216641 | Russell et al., 1999 *J Med Chem*, 42 | | |
| SL65.0155 | | zotepine | |
| spiroxatrine | Newman-Tancredi et al., 1997 *Naunyn Schmiedebergs Arch Pharmacol*, 355 | | |
| sumatriptan | | | |
| tandospirone | Nichols et al., 2002 *J Med Chem*, 45 | | |
| terguride | | | |
| U92012A | Blair et al., 2000 *J Med Chem*, 43 | | |
| xanomeline | | | |
| zalospirone | | | |
| ziprasidone | | | |
| zolmitriptan | | | |

FIG. 16TT

Serotonin 5-HT1B receptor

| Agonists | References | Antagonists | References |
|---|---|---|---|
| 5-(nonyloxy)-tryptamine | | (-)-pindolol | |
| alniditan | Granas and Larhammar 1999 *Eur J Pharmacol*, 380 | (R)-flurocarazolol | |
| [³H]alniditan | | (S)-flurocarazolol | |
| aripiprazole | | cyanopindolol | |
| BMS 181,101 | Leysen et al., 1996 *Mol Pharmacol*, 50 | [³H]GR-125743 | Roth et al., 2001 *Psychopharmacology (Berl)*, 157 |
| BRL-15572 | | GR-127935 | |
| bromocriptine | Lesage et al., 1998 *Br J Pharmacol*, 123 | ketanserin | |
| cabergoline | | ketanserin | Maroteaux et al., 1992 *Proc Natl Acad Sci U S A*, 89 |
| CGS-12066 | | metergoline | |
| clozapine | Shapiro et al., 2003 *Neuropsychopharmacology*, 28 | methiothepin | Granas and Larhammar 1999 *Eur J Pharmacol*, 380 |
| CP-122288 | | methysergide | |
| 5-CT | | mianserin | Lesage et al., 1998 *Br J Pharmacol*, 123 |
| dihydroergotamine | Newman-Tancredi et al., 2000 *Mol Pharmacol*, 58 | ocaperidone | |
| dipropyl-5-CT | | 5-OH-DPAT | Parker et al., 1996 *J Neurochem*, 67 |
| donitriptan | | 9-OH-risperidone | |
| eletriptan | Price et al., 1997 *Naunyn Schmiedebergs Arch. Pharmacol.*, 356 | pipamperone | |
| [³H]eletriptan | | rauwolscine | Schotte et al., 1996 *Psychopharmacology (Berl)*, 124 |
| F 11356 | | risperidone | |
| GR-55562 | | | |
| GR 127935 | | ritanserin | |
| 5-HT | | S33084 | |

FIG. 16UU

Serotonin 5-HT1B receptor

| Agonists | References | Antagonists | References |
|---|---|---|---|
| [³H]-5-HT | | SB 224289 | Roth et al., 2001 Psychopharmacology (Berl), 157 |
| L-694,247 | Davidson et al., 1997 Br J Pharmacol, 121 | SB 272183 | |
| L-772,405 | | SB 649915 | Maroteaux et al., 1992 Proc Natl Acad Sci U S A, 89 |
| L-775,606 | Selkirk et al., 1998 Br J Pharmacol, 125 | SB 714786 | Granas and Larhammar 1999 Eur J Pharmacol, 380 |
| lisuride | | sertindole | |
| LY344864 | Newman-Tancredi et al., 1999 Naunyn Schmiedebergs Arch Pharmacol, 359 | spiperone | Lesage et al., 1998 Br J Pharmacol, 123 |
| lysergol | | (+)-WAY 100135 | Parker et al., 1996 J Neurochem, 67 |
| 2-Me-5-HT | Leysen et al., 1996 Mol Pharmacol, 50 | yohimbine | |
| 5-MeOT | | yohimbine | Schotte et al., 1996 Psychopharmacology (Berl), 124 |
| 7-methoxy-1-naphthylpiperazine | Granas and Larhammar 1999 Eur J Pharmacol, 380 | zotepine | |
| 1-naphthylpiperazine | | | |
| naratriptan | | | |
| 8-OH-DPAT | | | |
| [³H]8-OH-DPAT | | | |
| olanzapine | | | |
| ORG-5222 | | | |
| oxymetazoline | | | |
| pergolide | | | |
| rizatriptan | | | |
| roxindole | | | |

FIG. 16VV

| Serotonin 5-HT1B receptor | |
|---|---|
| Agonists | References |
| RU 24969 | |
| SB 216641 | |
| SL65.0155 | Shapiro et al., 2003 *Neuropsychopharmacology*, 28 |
| sumatriptan | |
| [³H]sumatriptan | Newman-Tancredi et al., 2000 *Mol Pharmacol*, 58 |
| terguride | Price et al., 1997 *Naunyn Schmiedebergs Arch. Pharmacol.*, 356 |
| TFMPP | |
| tryptamine | Leysen et al., 1996 *Mol Pharmacol*, 50 |
| xanomeline | |
| ziprasidone | |
| zolmitriptan | |

FIG. 16WW

Serotonin 5-HT1D receptor

| Agonists | References | Antagonists | References |
|---|---|---|---|
| alniditan | Lesage et al., 1998 Br J Pharmacol, 123 | m-CPP | Millan et al., 2002 J Pharmacol Exp Ther, 303, |
| [³H]alniditan | | bufotenine | |
| aripiprazole | Shapiro et al., 2003 Neuropsychopharmacology, 28 | cyanopindolol | |
| BRL-15572 | | fluspirilene | Weinshank et al., 1992 Proc. Natl. Acad. Sci. U.S.A., 89 |
| bromocriptine | | GR-127935 | |
| cabergoline | | haloperidol | |
| CGS-12066 | Price, et al., 1997 Naunyn Schmiedebergs Arch. Pharmacol., 356 | ketanserin | Schotte et al., 1996 Psychopharmacology (Berl), 124 |
| clozapine | | L-772,405 | |
| CP-122288 | | metergoline | |
| 5-CT | Millan et al., 2002 J Pharmacol Exp Ther, 303, | methiothepin | Hamblin and Metcalf 1991 Mol Pharmacol, 40 |
| dihydroergotamine | | methysergide | |
| dimethyltryptamine | | MPDT | |
| dipropyl-5-CT | Weinshank et al., 1992 Proc. Natl. Acad. Sci. U.S.A., 89 | ocaperidone | Leysen et al., 1996 Mol Pharmacol, 50, |
| donitriptan | | 9-OH-risperidone | |
| eletriptan | | pipamperone | |
| [³H]eletriptan | Schotte et al., 1996 Psychopharmacology (Berl), 124 | rauwolscine | Millan et al., 2000 J Pharmacol Exp Ther, 293 |
| EMDT | | risperidone | |
| F 11356 | Domenech et al., 1997 Naunyn Schmiedebergs Arch Pharmacol, 356 | ritanserin | |
| GR 127935 | | | |
| 5-HT | | | |

FIG. 16XX

Serotonin 5-HT1D receptor

| Agonists | References | Antagonists | References |
|---|---|---|---|
| [³H]5-HT | Shapiro et al., 2003 Neuropsychopharmacology, 28 | S33084 | Millan et al., 2002 J Pharmacol Exp Ther, 303, |
| lisuride | | SB 224289 | |
| LY344864 | Price, et al., 1997 Naunyn Schmiedebergs Arch. Pharmacol., 356 | SB 272183 | Weinshank et al., 1992 Proc. Natl. Acad. Sci. U.S.A., 89 |
| (+)-lysergic acid | | | |
| lysergol | | SB 277011-A | |
| α-Me-5-HT | Millan et al., 2002 J Pharmacol Exp Ther, 303, | SB 649915 | Schotte et al., 1996 Psychopharmacology (Berl), 124 |
| 2-Me-5-HT | | | |
| 5-MeOT | Weinshank et al., 1992 Proc. Natl. Acad. Sci. U.S.A., 89 | SB 714786 | |
| 7-methoxy-1-naphthylpiperazine | | sertindole | |
| 1-naphthylpiperazine | Napier, et al., 1999 Eur J Pharmacol, 368, | spiperone | Hamblin and Metcalf 1991 Mol Pharmacol, 40 |
| naratriptan | | (+)-WAY 100135 | |
| 8-OH-DPAT | Glennon et al., 2000 J Med Chem, 43 | yohimbine | Leysen et al., 1996 Mol Pharmacol, 50, |
| [³H]8-OH-DPAT | | | |
| olanzapine | Leysen et al., 1996 Mol Pharmacol, 50, | | |
| ORG-5222 | | | |
| oxymetazoline | | zotepine | Millan et al., 2000 J Pharmacol Exp Ther, 293 |
| pergolide | | | |
| quetiapine | | | |
| rizatriptan | | | |
| roxindole | | | |

FIG. 16YY

| Serotonin 5-HT1D receptor | |
|---|---|
| Agonists | References |
| RU 24969 | Price, et al., 1997 Naunyn Schmiedebergs Arch. Pharmacol., 356 |
| SB 216641 | |
| SL65.0155 | Millan et al., 2002 J Pharmacol Exp Ther, 303, |
| sumatriptan | Weinshank et al., 1992 Proc. Natl. Acad. Sci. U.S.A., 89 |
| [$^3$H]sumatriptan | Napier, et al., 1999 Eur J Pharmacol, 368 |
| terguride | Phebus et al., 1997 Life Sci, 61 |
| TFMPP | |
| tryptamine | Schotte et al., 1996 Psychopharmacology (Berl), 124 |
| xanomeline | |
| ziprasidone | |
| zolmitriptan | |

FIG. 16ZZ

Serotonin 5-ht1e receptor

| Agonists | references | Antagonists | References |
|---|---|---|---|
| m-CPP | Baiet al., 2004 Eur J Pharmacol, 484 | fluspirilene | |
| BRL-15572 | | metergoline | |
| clozapine | Schotte et al., 1996 Psychopharmacology (Berl), 124 | methiothepin | Schotte et al., 1996 Psychopharmacology (Berl), 124 |
| 5-CT | Adham et al., 1993 Proc Natl Acad Sci U S A, 90, | methylergonovine | |
| dihydroergotamine | | methysergide | McAllister et al., 1992 Proc Natl Acad Sci U S A, 89, |
| DOI | Parker et al., 1996 J Neurochem, 67 | 1-naphthylpiperazine | |
| donitriptan | | 9-OH-risperidone | Adham et al., 1993 Proc Natl Acad Sci 90 |
| eletriptan | John et al., 1999 J Pharmacol Exp Ther, 290, | rauwolscine | |
| EMDT | | risperidone | Parker et al., 1996 J Neurochem, 67 |
| ergonovine | Bai et al., 2004 Eur J Pharmacol, 484, | sertindole | |
| ergotamine | | yohimbine | |
| 5-fluorotryptamine | Schotte et al., 1996 Psychopharmacology (Berl), 124 | zotepine | |
| GR-127935 | | | |
| 5-HT | | | |
| [³H]5-HT | | | |
| LY344864 | | | |
| lysergol | | | |

FIG. 16AAA

| Serotonin 5-ht1e receptor | |
|---|---|
| α-Me-5-HT | |
| 2-Me-5-HT | |
| 5-MeO-DMT | Bai et al., 2004 *Eur J Pharmacol*, 484 |
| 5-MeOT | |
| naratriptan | Schotte et al., 1996 *Psychopharmacology (Berl)*, 124 |
| 8-OH-DPAT | Adham et al., 1993 *Proc Natl Acad Sci U S A*, 90, |
| olanzapine | |
| ORG-5222 | Parker et al., 1996 *J Neurochem*, 67 |
| quetiapine | |
| rizatriptan | John et al., 1999 *J Pharmacol Exp Ther*, 290, |
| sumatriptan | Bai et al., 2004 *Eur J Pharmacol*, 484, |
| TFMPP | |
| tryptamine | Schotte et al., 1996 *Psychopharmacology (Berl)*, 124 |
| xanomeline | |
| ziprasidone | |
| zolmitriptan | |

FIG. 16BBB

| Serotonin 5-HT1F receptor | | | |
|---|---|---|---|
| Agonists | references | Antagonists | references |
| BRL-15572 | Dhawan, et al., 1996 Pharmacol. Rev., 48 | metergoline | |
| clozapine | | metergoline | |
| 5-CT | Horan et al., 1993 J Pharmacol Exp Ther, 266 | methiothepin | Wang et al., 1994 FEBS Lett., 348 |
| 5-CT | | methylergonovine | |
| dihydroergotamine | | methysergide | Mollereau et al., 1994 FEBS Lett. 341 |
| dipropyl-5-CT | Zajac et al., 1983 Biochem. Biophys. Res. Commun., 111 | methysergide | |
| DOI | | 1-naphthylpiperazine | Zajac et al., 1983 Biochem. Biophys. Res. Commun., 111, |
| donitriptan | | | |
| eletriptan | Wang et al., 1994 FEBS Lett., 348, | risperidone | Horan et al., 1993 J Pharmacol Exp Ther, 266, |
| ergotamine | | | |
| ergotamine | Mollereau et al., 1994 FEBS Lett. 341, | sertindole | |
| GR-127935 | | | |
| 5-HT | Hu et al., 1998 J Neurosci, 18, | yohimbine | |
| 5-HT | | | |
| [³H]-5-HT | | yohimbine | |
| LY334370 | Pan et al., 2002 J Neurophysiol, 88 | | |
| [³H]LY334370 | | | |
| LY344864 | | | |
| α-Me-5-HT | | | |

FIG. 16CCC

| Serotonin 5-HT1F receptor | |
|---|---|
| Agonists | References |
| 2-Me-5-HT | Dhawan, et al., 1996 *Pharmacol. Rev.*, 48 |
| 5-MeO-DMT | |
| 5-MeOT | |
| NAN 190 | Horan et al., 1993 *J Pharmacol Exp Ther*, 266 |
| naratriptan | |
| 8-OH-DPAT | Zajac et al., 1983 *Biochem. Biophys. Res. Commun.*, 111 |
| olanzapine | Wang et al., 1994 *FEBS Lett*, 348, |
| quetiapine | |
| rizatriptan | Mollereau et al., 1994 *FEBS Lett*, 341, |
| sumatriptan | |
| sumatriptan | Hu et al., 1998 *J Neurosci*, 18, |
| TFMPP | |
| tryptamine | Pan et al., 2002 *J Neurophysiol*, 88 |
| xanomeline | |
| zolmitriptan | |

FIG. 16DDD

Serotonin 5-ht5a receptor

| Agonists | References | | Antagonists | References |
|---|---|---|---|---|
| 5-CT | Matthes et al., 1993 *Mol. Pharmacol.*, 43 | | (-)-propranolol | Rees et al., 1994 *FEBS Lett.*, 355, |
| [³H]5-CT | | | bufotenine | |
| donitriptan | Grailhe et al., 2001 *Eur J Pharmacol*, 418, | | clozapine | Matthes et al., 1993 *Mol. Pharmacol.*, 43 |
| EMDT | | | ergotamine | Grailhe et al., 2001 *Eur J Pharmacol*, 418 |
| 5-HT | Erlander et al., 1993 *Proc Natl Acad Sci U S A*, 90, | | ketanserin | |
| [¹²⁵I]LSD | | | methiothepin | Erlander et al., 1993 *Proc Natl Acad Sci U S A*, 90, |
| lysergic acid | | | methysergide | |
| 8-OH-DPAT | John et al., 1999 *J Pharmacol Exp Ther*, 290 | | MPDT | Glennon et al., 2000 *J Med Chem*, 43 |
| RU 24969 | | | ritanserin | |
| sumatriptan | Rees et al., 1994 *FEBS Lett.*, 355, | | SB 699551 | Grailhe et al., 2001 *Eur J Pharmacol*, 418 |
| TFMPP | | | yohimbine | |

ELECTRIFIED COMPOSITIONS FOR DETERMINING THE RISK OF DEVELOPING ADOLESCENT IDIOPATHIC SCOLIOSIS THROUGH THE USE OF GI PROTEIN RECEPTOR

CROSS REFERENCE TO RELATED APPLICATIONS

This is a continuation of U.S. application Ser. No. 13/123,146, filed on Apr. 7, 2011, now abandoned, which is a National Entry Application of PCT application no. PCT/CA2009/001453 filed on Oct. 13, 2009 and published in English under PCT Article 21(2), which itself claims benefit of U.S. provisional application Ser. No. 61/104,442 filed on Oct. 10, 2008 and of U.S. provisional application Ser. No. 61/228,769, filed on Jul. 27, 2009. All documents above are incorporated herein in their entirety by reference.

STATEMENT REGARDING FEDERALLY SPONSORED RESEARCH OR DEVELOPMENT

N/A.

FIELD OF THE INVENTION

The present invention relates to the diagnosis of a predisposition to developing a scoliosis (e.g., adolescent idiopathic scoliosis (AIS)) and to screening assays for identifying compounds for treating scoliosis.

BACKGROUND OF THE INVENTION

Scoliosis is a medical condition in which a person's spine is curved from side to side, and may also be rotated. It is an abnormal lateral curvature of the spine. On an x-ray, the spine of an individual with a typical scoliosis may look more like an "S" or a "C" than a straight line.

Spinal deformities and scoliosis in particular represent the most prevalent type of orthopedic deformities in children and adolescents, while idiopathic scoliosis (AIS) represents the most common form of scoliosis. The etiology of adolescent idiopathic scoliosis (AIS) is unclear. AIS affects mainly girls in number and severity but in spite of several studies suggesting a genetic predisposition, the form of inheritance remains uncertain (Axenovich T I et al., *Am J Med Genet* 1999, 86(4): 389-394; Wise C A et al., *Spine* 2000, 25(18): 2372-2380; Blank R D et al., *Lupus* 1999, 8(5): 356-360; Giampietro P F et al., *Am J Med Genet* 1999, 83(3):164-177). Several divergent perspectives have been postulated to better define this etiology (Machida M., *Spine* 1999, 24(24): 2576-2583; Roth J A et al., *J Biol Chem* 1999, 274(31): 22041-22047; Hyatt B A et al., *Nature* 1996, 384(6604): 62-65; von Gall C et al., *Eur J Neurosci* 2000, 12(3): 964-972). Genetics, growth hormone secretion, connective tissue structure, muscle structure, vestibular dysfunction, melatonin secretion, and platelet microstructure are major areas of focus. The current opinion is that there is a defect of central control or processing by the central nervous system (CNS) that affects a growing spine and that the spine's susceptibility to deformation varies from one individual to another.

There is unfortunately no method approved by the FDA yet to identify children or adolescents at risk of developing IS to predict which affected individuals require treatment to prevent or stop progression of the disease (Weinstein S L, Dolan L A, Cheng J C et al. Adolescent idiopathic scoliosis. *Lancet* 2008; 371:1527-37). Consequently, the application of current treatments, such as bracing or surgical correction, is delayed until the detection of a significant deformity or a demonstration of clear progression, resulting in a delayed and less-than-optimal treatment. (Society SR. Morbidity & Mortality Committee annual Report 1997.). Among patients with IS requiring treatment, 80 to 90% will be treated by bracing and around 1% will need surgery to correct the deformity by spinal instrumentation and fusion of the thoracic and/or lumbar spine with the risk of having complications. (Weiss H R, Goodall D. Rate of complications in scoliosis surgery—a systematic review of the Pub Med literature. *Scoliosis*. 2008; 3:9). Today in the United States there are approximately one million children between ages 10 and 16 with some degree of IS. One out of every six children diagnosed with scoliosis will have a curve that progresses to a degree that requires active treatment. About 29,000 scoliosis surgeries are done every year in North America, resulting in significant psychological and physical morbidity. (Goldberg M S, Mayo N E, Poitras B et al. The Ste-Justine Adolescent Idiopathic Scoliosis Cohort Study. Part I: Description of the study. *Spine* 1994; 19:1551-61; Poitras B, Mayo N E, Goldberg M S et al. The Ste-Justine Adolescent Idiopathic Scoliosis Cohort Study. Part IV: Surgical correction and back pain. *Spine* 1994; 19:1582-8).

There is a need for methods for classifying subjects having diseases involving spinal deformities (e.g., scoliosis, such as AIS), for diagnosing a predisposition to scoliosis and for identifying compounds for preventing or treating these diseases.

The present description refers to a number of documents, the content of which is herein incorporated by reference in their entirety.

SUMMARY OF THE INVENTION

The present invention demonstrates for the first time that cells from scoliotic patients (idiopathic scoliosis patients) exhibit a broad impairment in G-protein coupled receptor (GPCR) signaling. This impairment was measured in several different GPCRs and in various cell types including bone-forming cells, muscle-forming cells as well as blood cells.

A variety of hormones, neurotransmitters and biologically active substances control, regulate, or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G protein-coupled receptors ("GPCR"s). Binding of a specific signaling molecule to the GPCR can cause a conformational change in the receptor, resulting in a form that is able to bind and activate a G protein, thereby triggering a cascade of intracellular events that eventually leads to a biological response. Typically, GPCRs interact with G proteins to regulate the synthesis of intracellular second messengers such as cyclic AMP, inositol phosphates, diacylglycerol and calcium ions.

More specifically, in accordance with the present invention, there is provided a method (e.g., an in vitro method) for determining whether a test compound is useful for preventing or treating scoliosis (e.g., an idiopathic scoliosis (IS), such as Infantile Idiopathic Scoliosis, Juvenile Idiopathic Scoliosis, Adolescent Idiopathic Scoliosis (AIS) or adult scoliosis), said method comprising: (a) contacting a cell expressing a receptor (i.e. at least one receptor) coupled to an inhibitory guanine nucleotide-binding ($G_i$) protein with a ligand to said receptor in the presence or absence of said test compound; (b) determining the magnitude of the signal induced by said ligand in said cell; wherein a higher signal in the presence relative to the absence of said test compound is indicative that said test compound is useful for preventing or treating a scoliosis (e.g., an Idiopathic Scoliosis, such as AIS).

This method can be used for screening for compounds able to modulate $G_i$-protein-signaling impairment generally. It can however also be used to determine which compound is the most effective for modulating and in particular reducing or counteracting the $G_i$-protein-signaling impairment in cells from a specific group of patient or for a specific patient. Indeed, the most effective compound for these purposes may vary from one patient to the next. The method of screening of the present invention may therefore be used to identify which compound is the most effective in counteracting the $G_i$-protein-signaling impairment in a specific group of patients or in one patient in particular.

The present invention also provides a method (e.g., an in vitro method) for diagnosing a predisposition to developing a scoliosis (e.g., an Idiopathic Scoliosis such as Infantile Idiopathic Scoliosis, Juvenile Idiopathic Scoliosis or Adolescent Idiopathic Scoliosis (AIS)) in a subject comprising:
(a) contacting a cell expressing a receptor coupled to an inhibitory guanine nucleotide-binding ($G_i$) protein from said subject with a ligand to said receptor;
(b) determining the magnitude of the signal induced by said ligand in said cell;
(c) comparing said signal to a corresponding reference signal;
(d) determining said predisposition based on said comparison.

As used herein the terms "predisposition to developing a scoliosis" refer to a genetic or metabolic predisposition of a subject to develop a scoliosis (i.e. spinal deformity) and/or a more severe scoliosis at a future time.

In another aspect, the present invention provides a method of classifying a human subject having an idiopathic scoliosis, such as Infantile Idiopathic Scoliosis, Juvenile Idiopathic Scoliosis or Adolescent Idiopathic Scoliosis (AIS) comprising:
(a) contacting a cell expressing a receptor coupled to an inhibitory guanine nucleotide-binding ($G_i$) protein from said subject with a ligand to said receptor; and
(b) determining the magnitude of the signal induced by said ligand in said cell, whereby the results of the determining step enables the classification of the subject having idiopathic scoliosis (e.g., AIS) in one idiopathic scoliosis subgroup.

In an embodiment, the above-mentioned idiopathic scoliosis is AIS. In an embodiment, the AIS subject (i) is classified in subgroup 1 if the magnitude of the signal is about 34% or less relative to the magnitude of a corresponding signal measured in a cell from a control subject, (ii) is classified in subgroup 2 if the magnitude of the signal is between about 34% and about 57% relative to the magnitude of a corresponding signal measured in a cell from a control subject, and (iii) is classified in subgroup 3 if the magnitude of the signal is between about 57% to about 80% relative to the magnitude of a corresponding signal measured in a cell from a control subject.

As such, the method of the present invention may also be advantageously used to determine, for example, the type and/or severity of the disease or the nature of the defect underlying the disease (i.e., "classification" or "stratification" of the subjects). This is particularly interesting if the most effective drug for treating or preventing idiopathic scoliosis (e.g., AIS) varies between subjects affected by idiopathic scoliosis of different types and/or severities. The method for classifying of the present invention may therefore permit a better selection of the drug to be used for a particular patient. This method is also useful to classify/stratify already diagnosed scoliotic patients (e.g., adult scoliosis).

In an embodiment, the above-mentioned subject is a likely candidate for developing a scoliosis, such as idiopathic scoliosis (e.g., Infantile Idiopathic Scoliosis, Juvenile Idiopathic Scoliosis or Adolescent Idiopathic Scoliosis (AIS)). As used herein the terms "likely candidate for developing scoliosis" include subjects (e.g., children) of which at least one parent has a scoliosis (e.g., adolescent idiopathic scoliosis). Among other factors, age (adolescence), gender and other family antecedent are factors that are known to contribute to the risk of developing a scoliosis and are used to a certain degree to assess the risk of developing a scoliosis. In certain subjects, scoliosis develops rapidly over a short period of time to the point of requiring a corrective surgery (often when the deformity reaches a Cobb's angle $\geq 50°$). Current courses of action available from the moment a scoliosis such as AIS is diagnosed (when scoliosis is apparent) include observation (when Cobb's angle is around 10-25°), orthopaedic devices (when Cobb's angle is around 25-30°), and surgery (over 45°). A more reliable determination of the risk of progression could enable to 1) select an appropriate diet to remove certain food products identified as contributors to scoliosis; 2) select the best therapeutic agent; and/or 3) select the least invasive available treatment such as postural exercises, orthopaedic device, or less invasive surgeries or surgeries without fusions (a surgery that does not fuse vertebra and preserves column mobility). The present invention encompasses selecting the most efficient and least invasive known preventive actions or treatments in view of the determined risk of developing scoliosis.

The methods of the invention may be performed using cell expressing one or more receptor(s) coupled to a $G_i$ protein (also known as $G_i$ alpha subunit). "Receptor" as used herein refers to wild-type receptors as well as to fragments and/or variants thereof that retains the activity (i.e. GPCR-mediated activity) of the wild-type receptors. GPCRs coupled to the $G_i$ protein (hereinafter referred to as $G_i$PCRs) include, for example, CD47, serotonin receptors (5-HT), adenosine receptors, adrenergic receptors, cannabinoid receptors, histamine receptors, prostaglandin receptors and dopamine receptors. FIGS. 15A-15G present a non exhaustive list of GiPCRs suitable for use in the method of the present invention.

In an embodiment, the above-mentioned receptor coupled to a $G_i$ protein is a serotonin receptor, an $\alpha$-adrenergic receptor, an adenosine receptor, a cannabinoid receptor or any combination thereof. In a further embodiment, the above-mentioned receptor is 5-HT1A, $\alpha$2-AD, A3 or CB2. In another embodiment, the above-mentioned receptor is not a melatonin receptor (e.g., MT2).

In an embodiment, the above-mentioned method is performed on more than one receptor coupled to a $G_i$ protein. In another embodiment, the above-mentioned method is performed using more than one ligand specific for a receptor coupled to a $G_i$ protein. In another specific embodiment, each ligand is specific to a different receptor coupled to a $G_i$ protein (e.g., 2, 3, 4, 5 or 6 ligands). FIGS. 16A-16DDD present a non exhaustive list of G$_i$PCRs ligands. In a specific embodiment, ligands for use in the present invention are not MT2 ligands.

Any sample (e.g., cells, tissues) in which one or more G$_i$-coupled receptors and/or G$_i$ proteins may be expressed may be used in accordance with the methods of the present invention. The cells may naturally or recombinantly express one or more G$_i$-coupled receptor(s), and/or a G$_i$ protein. For recombinant expression, a nucleic acid encoding a G$_i$PCR and/or a nucleic acid encoding a G$_i$ protein is introduced into a suitable cell, and the cell is incubated under conditions that provide for expression of the protein(s). The cells used herein naturally express one or more receptors coupled to G$_i$ proteins and were selected in part for their accessibility for collection from subjects. Hence, cells such as osteoblasts, osteoclasts, peripheral blood mononuclear cell (PBMC) (inherently including principally lymphocytes but also monocytes) and myoblasts are advantageously accessible and may conveniently be used in the methods of the present invention. Blood cells (e.g., PBMCs, platelets (thrombocytes), etc.) in particular are particularly accessible and provide for a more rapid testing. Any blood cell can be used for the methods of the present invention so long as it possesses at least one GPCR receptor coupled to a Gi protein. In an embodiment, the cells are obtained or derived from a subject having an idiopathic scoliosis (e.g., Infantile Idiopathic Scoliosis, Juvenile Idiopathic Scoliosis or Adolescent Idiopathic Scoliosis (AIS)). For the present invention, PBMCs do not need to be established in cultures since methods described herein can be performed in cell suspension with fresh or frozen PBMCs.

Any ligand of a given G$_i$-protein coupled receptor may be used in accordance with certain aspects of the present invention. Ligands (e.g., natural or synthetic) of G$_i$PCRs are well known in the art, and several of these ligands are commercially available (from Tocris Bioscience, for example). FIGS. 16A-16DDD presents a non-exhaustive list of G$_i$PCR ligands suitable for use in the method of the present invention either alone or in combination with other ligands. In a specific embodiment, the above-mentioned ligand is a known agonist of the receptor. In an embodiment, the above-mentioned ligand is (a) 1-[3-(3,4-Methylenedioxyphenoxy)propyl]-4-phenyl-piperazine maleate (known as BP554 maleate) for the 5-HT1A receptor, (b) 5-bromo-N-(4,5-dihydro-1H-imidazol-2-yl)-6-quinoxalinamine (known as UK14304) for the α2-AD receptor; (c) 1-Deoxy-1-[6-[[(3-iodophenyl)methyl]amino]-9H-purin-9-yl]-N-methyl-β-D-ribofuranuronamide (known as IB-MECA) for the A3 receptor; (d) N-Cyclohexyl-7-chloro-1-[2-(4-morpholinyl)ethyl]quinolin-4(1H)-one-3-carboxamide (known as CB65) for the CB2 receptor.

It should be understood that a variety of different test compounds may be screened by the above methods. Test compounds encompass numerous chemical classes, though typically they are organic molecules, preferably small organic compounds having a molecular weight of more than 50 and less than about 2,500 Daltons. Test compounds comprise functional groups necessary for structural interaction with proteins, particularly hydrogen bonding, and typically include at least an amine, carbonyl, hydroxyl or carboxyl group, preferably at least two of the functional chemical groups. The test compounds often comprise cyclical carbon or heterocyclic structures and/or aromatic or polyaromatic structures substituted with one or more of the above functional groups. Test compounds are also found among biomolecules including peptides (e.g., peptides targeting one or more defective protein(s) involved in the transduction of the signal through receptors coupled to G$_i$ proteins), nucleic acids (e.g., oligonucleotides such as antisense molecules targeting a defective gene involved in the transduction of the signal through receptors coupled to G$_i$ proteins), antibodies, saccharides, fatty acids, steroids, purines, pyrimidines, derivatives, structural analogs or combinations thereof. Test compounds may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In an embodiment, the reference signal is a signal obtained in a corresponding sample (e.g., a cell) obtained or derived from a control subject, such as a subject (e.g., age- and/or gender-matched) who has not developed a scoliosis (e.g., idiopathic scoliosis such as Infantile Idiopathic Scoliosis, Juvenile Idiopathic Scoliosis or Adolescent Idiopathic Scoliosis (AIS)), or who is not predisposed to developing a scoliosis. In that case, a lower signal in the cell from the subject relative to the corresponding reference signal is indicative that the subject has a predisposition to developing a scoliosis, whereas a higher or a substantially identical signal is indicative that the subject does not have a predisposition to developing a scoliosis.

In another embodiment, the above-mentioned reference signal is a signal obtained in a corresponding sample (e.g., a cell) obtained or derived from a subject (e.g., age- and/or gender-matched) who has developed a scoliosis (e.g., idiopathic scoliosis such as Infantile Idiopathic Scoliosis, Juvenile Idiopathic Scoliosis or Adolescent Idiopathic Scoliosis (AIS)), or who is known to be predisposed to developing a scoliosis. In that case, a lower or a substantially identical signal in the cell from the subject relative to the corresponding reference signal is indicative that the subject has a predisposition to developing a scoliosis, whereas a higher signal is indicative that the subject does not have a predisposition to developing a scoliosis.

In an embodiment, the corresponding sample is a cell of the same type (e.g., both the test sample and the reference sample(s) are lymphocytes) as that from the subject. In an embodiment, the assay will be assayed in plates (e.g., 96-wells, 384-wells, etc.) containing the test sample and a control sample. In another embodiment, the plates also contain reference samples from a healthy subject and from subjects of the groups 1, 2 and 3.

In an embodiment, a lower or higher signal refers to a difference of at least about 10%, in further embodiments at least about 15%, 20%, 25%, 30%, 35%, 40%, 45%, 50%, 55%, 60%, 65%, 70% 75%, 80%, 85%, 90%, 95% 100%, 150% or 200% between the signal obtained with the test sample (sample obtained from the subject being tested) relative to the reference signal. In an embodiment, a substantially identical signal refers to a signal that differs by less than 10%, in further embodiments by less than 9%, 8%, 7%, 6% or 5%, as compared to the reference signal.

The changes in the magnitude of the signal induced by the ligand (e.g. an agonist) may be detected using any methods. Methods for measuring the magnitude or intensity of the signal (e.g., intracellular response) mediated through GiPCRs are well known in the art. The magnitude of the signal may be determined, for example, by measuring the level of a molecule, such as a second messenger (e.g., cAMP, $Ca^{2+}$) or a gene product (e.g., mRNA or protein) whose level is modulated following triggering of the receptor by a ligand. The magnitude of the signal may also be determined, for example, by measuring changes in protein-protein interactions (e.g., by fluorescence resonance energy transfer [FRET] or bioluminescence resonance energy transfer [BRET]) following triggering of the receptor by a ligand. Other methods to measure the magnitude or intensity of the signal mediated through GiPCRs include, for example, measurement of cAMP levels (Medhurst et al., 2003. In: J Neurochem., 84), measurement of thallium flux using GIRK-thallium Flux Assay (Niswender et al., 2008; In: Mol Pharmacol. 73(4)), Patch-clamp (Saugstad et al., 1996. In: J. Neurosci. 16), measurement of GTPγS binding using [$^{35}$S] GTPγS labelling assay (Riobo et al., 2006. In: Proc Natl Acad Sci USA, 103), and measurement of the changes in impedance (Peters et al., 2007. In: J Biomol. Screen. 12: 312-9). In an embodiment, the magnitude of the signal is determined using the changes in impedance that occurs in the cell following receptor triggering (e.g., cellular dielectric spectroscopy [CDS]). Such measurement may be made, for example, using the real-time cell electronic sensing (RT-CES™) technology (ACEA Biosciences Inc., San Diego, Calif., USA) (Huang et al., Analyst, 2008, 133(5): 643-648; Solly et al., Assay Drug Dev. Technol, 2004, 2(4): 363-372) or using the CELLKEY™ label-free cellular analysis technology (MDS Sciex, Concord, Ontario, Canada) according to the method described below.

In embodiment, the methods are performed in a format suitable for high throughput assays, e.g., 96- or 384-well format, and suitable robots, (e.g., pipetting robots), and instrumentation may be used.

Also provided by the present invention are kits for practicing the above-mentioned methods. The kits may include, for example, one or more reagent(s) to determine a $G_i$ protein-coupled receptor signal, as well as buffers, cells, control samples (e.g., sample from a healthy subject, reference samples of patients of the group 1, 2 and 3), containers, etc. for performing the subject assays. The various components of the kit may be present in separate containers or certain compatible components may be pre-combined into a single container, as desired.

In addition to above-mentioned components, the kits typically further include instructions for using the components of the kit to practice the methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

In another aspect, the present invention provides a method for preventing and/or treating a scoliosis (e.g., idiopathic scoliosis such as Infantile Idiopathic Scoliosis, Juvenile Idiopathic Scoliosis or Adolescent Idiopathic Scoliosis (AIS)) comprising administering an effective amount of a compound (and/or a composition comprising a compound) identified by the above-described screening method to a subject.

Compositions (e.g., pharmaceutical compositions) are prepared by formulating the compounds (e.g., peptides, small molecules) identified by the above-described screening method, with any suitable pharmaceutical carrier/excipient or combination of pharmaceutical carriers/excipients. Preparations may be made for administration by any route, such as intravenous, intramuscular, subcutaneous, oral, rectal, vaginal, transdermal, transmucosal, sublingual and the like.

In an embodiment, the above-mentioned subject is a mammal, in a further embodiment, a human.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 9 shows that the altered response of Gi-coupled receptors to ligand stimulation is detected in PBMCs from family #24. The maximal impedance of all shown members of the family was measured by Cellular Dielectric Spectroscopy (CDS). *** means p<0.001;

FIGS. 10A and 10B show that the altered response of Gi-coupled receptors to ligand stimulation is detected in PBMCs from four families: 23, 24, 29 and 39. The maximal impedance of all shown members of the families were measured by Cellular Dielectric Spectroscopy (CDS). *** means p<0.001;

FIGS. 11A-11F show ranges of values obtained in osteoblasts from control subjects and AIS patients belonging to functional groups 1, 2 and 3 using (FIG. 11A) 300 μM melatonin, (FIG. 11B) 300 μM iodomelatonin, (FIG. 11C) 300 μM BP554, (FIG. 11D) 300 μM UK14304, (FIG. 11E) 300 μM IB-meca and (FIG. 11F) 300 μM CB65, as measured by Cellular Dielectric Spectroscopy (CDS);

FIGS. 15A-15G show a list of known Gi-protein coupled receptors; and

FIGS. 16A-16DDD show a list of known ligands to Gi-protein coupled receptors.

DESCRIPTION OF ILLUSTRATIVE EMBODIMENTS

Figure 1:
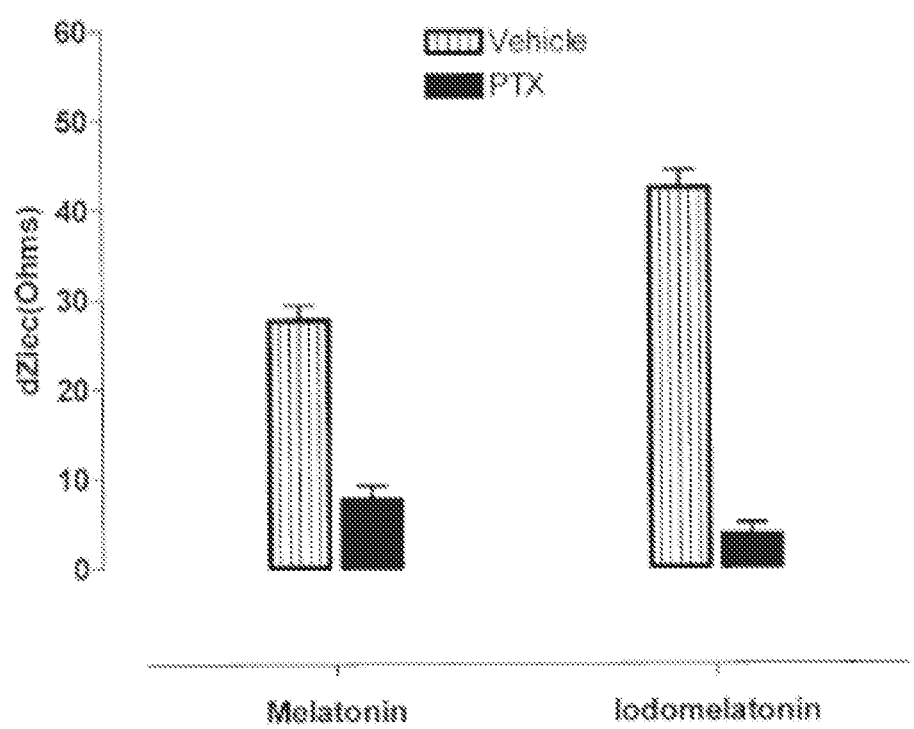
FIG. 1 presents the contribution of Gi proteins in melatonin signaling detected by CDS. Data in the graph were generated from maximum impedance responses and correspond to the mean±SE of 3 independent experiments performed in triplicate.

The present invention is illustrated in further details by the following non-limiting examples.

Example 1

Clinical Characteristics of Subjects (Control, AIS and Asymptomatic)

The clinical characteristics of the examined healthy subjects (controls), AIS subject and asymptomatic subjects are presented in Tables I-III below, respectively.

TABLE I

Clinical data of healthy control subjects.

| Case Number | Gender | Age |
|---|---|---|
| 5 | Female | 10.6 |
| 11 | Male | 11.3 |
| 20 | Female | 10.0 |
| 21 | Female | 10.4 |
| 23 | Male | 10.3 |
| 33 | Male | 10.1 |
| 43 | Female | 14.9 |
| 60 | Female | 14.4 |
| 61 | Female | 16.3 |
| 68 | Female | 12.9 |
| 69 | Female | 14.5 |
| 86 | Female | 13.7 |
| 4110 | Female | 17.3 |
| 4112 | Male | 13.6 |
| 4115 | Female | 14.7 |
| 4121 | Male | 13.8 |
| 4124 | Female | 12.8 |
| 4126 | Female | 14.6 |
| 4131 | Male | 15.5 |
| 4135 | Male | 15.8 |
| 4137 | Female | 16.8 |
| 4138 | Female | 13.1 |
| 4140 | Male | 14.9 |
| 4142 | Female | 15.3 |
| 4143 | Female | 13.1 |
| 4148 | Male | 14.8 |
| 4149 | Female | 15.4 |
| 4150 | Female | 15.2 |
| 4159 | Male | 14.0 |
| 4161 | Male | 13.3 |
| 4174 | Female | 12.9 |
| 4179 | Female | 16.6 |
| 4181 | Male | 15.9 |
| 4182 | Female | 15.7 |
| 4190 | Male | 16.3 |
| 4191 | Female | 15.7 |
| 4193 | Female | 17.3 |
| 4195 | Female | 16.3 |
| 4200 | Female | 13.6 |
| 4205 | Male | 11.3 |

TABLE I-continued

Clinical data of healthy control subjects.

| Case Number | Gender | Age |
|---|---|---|
| 4206 | Male | 11.4 |
| 4209 | Female | 15.8 |

*All reported data is that from first collection date.

TABLE II

Clinical data of AIS patients

| Case Number Group | Gender | Age | Cobb Angle | Curve Pattern |
|---|---|---|---|---|
| 113 / 3 | Female | 9.7 | 10 | Right Thoracic |
| 151 / 3 | Female | 13.1 | 31 | Right Thoracic |
| 155 / 2 | Female | 15.4 | 20 | Left Thoracolumbar |
| 159 / 3 | Female | 8.3 | 7 | Left Lumbar |
| 165 / 3 | Female | 10.8 | 26 | Right Thoracic |
|  |  |  | 23 | Left Lumbar |
| 168 / 3 | Female | 14.2 | 16 | Right Thoracic |
|  |  |  | 18 | Left Thoracolumbar |
| 208 / 3 | Female | 9.8 | 26 | Left Thoracolumbar |
| 254 / 3 | Female | 15.2 | 28 | Left Thoracolumbar |
| 271 / 3 | Female | 12.4 | 23 | Right Thoracic |
| 275 / 2 | Female | 11.0 | 27 | Right Thoracic |
|  |  |  | 1 | Left Lumbar |
| 276 / 3 | Female | 13.1 | 19 | Right Thoracic |
|  |  |  | 19 | Left Lumbar |
| 281 / 3 | Female | 12.6 | 7 | Left Thoracolumbar |
| 282 / 2 | Female | 9.7 | 20 | Left Lumbar |
| 302 / 3 | Female | 14.4 | 14 | Right Thoracic |
|  |  |  | 12 | Left Lumbar |
| 306 / 2 | Female | 13.1 | 13 | Right Thoracic |
|  |  |  | 18 | Left Lumbar |
| 327 / 1 | Female | 16.4 | 21 | Right Thoracic |
| 336 / 3 | Female | 14.0 | 6 | Right Thoracic |
|  |  |  | 12 | Left Lumbar |
| 404 / 3 | Female | 14.6 | 25 | Right Thoracic |
| 425 / 3 | Female | 24.6 | 52 | Left Thoracolumbar |
| 475 | Female | 13.2 | 19 | Left Thoracolumbar |
| 541 / 2 | Male | 15.3 | 13 | Right Thoracic |
| 542 / 2 | Female | 15.6 | 21 | Right Thoracic |
|  |  |  | 26 | Left Thoracolumbar |
| 543 / 2 | Female | 10.9 | 10 | Right Thoracic |
|  |  |  | 8 | Left Thoracolumbar |
| 544 / 2 | Female | 15.1 | 8 | Left Thoracic |
|  |  |  | 2 | Right Thoracolumbar |
| 548 / 3 | Female | 15.6 | 16 | Right Lumbar |
| 1020 / 3 | Female | 19.9 | 59 | Right Thoracic |
|  |  |  | 55 | Left Lumbar |
| 1060 / 3 | F | 12.0 | 48 | Right thoracic |
|  |  |  | 38 | Left lumbar |
| 1198 / 3 | Female | 16.3 | 20 | Right Thoracolumbar |
| 1311 / 2 | F | 15.52 | 42 | Right thoracic |
| 1332 / 3 | F | 13.11 | 35 | Right thoracic |
| 1385 / 2 | Female | 16.1 | 27 | Left Thoracic |
|  |  |  | 42 | Right Thoracic |
|  |  |  | 23 | Left Lumbar |
| 1468 / 3 | Male | 15.5 | 69 | Right Thoracolumbar |
| 1474 / 1 | Male | 17.9 | 54 | Right Thoracic |
|  |  |  | 52 | Left Lumbar |
| 1488 / 1 | Male | 15.4 | 87 | Right Thoracic |
| 1513 / 3 | Female | 15.6 | 11 | Right Thoracic |
|  |  |  | 12 | Left Lumbar |
| 1520 / 3 | Female | 14.6 | 54 | Right Thoracic |
|  |  |  | 42 | Left Thoracolumbar |
| 1545 / 3 | Female | 13.5 | 57 | Right Thoracic |
| 1549 / 1 | Female | 14.8 | 24 | Right Thoracic |
|  |  |  | 55 | Left Thoracolumbar |
| 1550 / 2 | Female | 12.3 | 60 | Right Thoracic |
|  |  |  | 51 | Left Lumbar |
| 1552 / 3 | Female | 18.5 | 30 | Left Thoracic |
|  |  |  | 66 | Right Thoracic |
|  |  |  | 37 | Left Lumbar |
| 1554 / 3 | Female | 14.7 | 49 | Right Thoracolumbar |
| 1557 / 2 | Female | 12.1 | 83 | Right Thoracic |
|  |  |  | 54 | Left Lumbar |
| 1562 / 3 | Female | 19.1 | 51 | Right Thoracic |
|  |  |  | 41 | Left Lumbar |
| 1566 / 3 | Female | 12.2 | 53 | Left Thoracic |
|  |  |  | 74 | Right Thoracic |

*All reported data is that from first collection date.

TABLE III

Clinical data of asymptomatic at-risk subjects studied.

| Case Number Group Number | Gender | Age |
|---|---|---|
| 3004 / 2 | Female | 8.6 |
| 3006 / 3 | Male | 5.8 |
| 3009 / 2 | Female | 3.0 |
| 3018 / 3 | Female | 11.3 |
| 3023 / 3 | Female | 9.5 |
| 3027 / 2 | Female | 14.1 |
| 3030 / 3 | Male | 10.7 |
| 3040 / 3 | Male | 9.7 |
| 3043 / 3 | Female | 4.7 |
| 3054 / 1 | Female | 8.2 |
| 3057 / 3 | Female | 15.3 |
| 3058 / 3 | Female | 8.0 |
| 3062 / 3 | Male | 14.5 |
| 3065 / 3 | Female | 12.2 |
| 3067 / 3 | Female | 12.0 |
| 3068 / 3 | Male | 12.0 |
| 3070 / 2 | Female | 8.5 |
| 3071 / 3 | Male | 5.5 |

TABLE III-continued

Clinical data of asymptomatic at-risk subjects studied.

| Case Number Group Number | Gender | Age |
|---|---|---|
| 3080 3 | Female | 10.0 |
| 3081 3 | Male | 16.2 |
| 3082 3 | Female | 7.6 |
| 3095 3 | Male | 10.7 |
| 3096 3 | Female | 8.5 |
| 3098 3 | Male | 12.5 |
| 3099 3 | Female | 10.4 |
| 3115 3 | Male | 10.6 |
| 3116 3 | Female | 9.5 |
| 3123 3 | Female | 10.8 |
| 3124 3 | Male | 15.0 |
| 3159 3 | Female | 5.1 |

*All reported data is that from first collection date.

Clinical Characteristics of Subjects from which Cells were Isolated for Examples 3-4 and 8-10.

The institutional review boards of The Sainte-Justine Hospital, The Montreal Children's Hospital, The Shriners Hospital for Children in Montreal and McGill University approved this study. Parents or legal guardians of all participants gave written informed consent, and minors gave their assent. All patients with IS were examined by one of the six orthopedic surgeons participating in this study. A person was deemed to be affected if history and physical examination were consistent with the diagnosis of IS and a minimum of a ten degree curvature in the coronal plane with vertebral rotation was found by radiograph. A summary of demographics and clinical characteristics of these subjects are shown in Table IV below. These subjects are also included in Table II above.

A number of young asymptomatic children born from one parent affected by IS were also enrolled in the study to evaluate the performance of the test in the asymptomatic population. Each subject was examined by the same orthopedic surgeon in a clinic for early detection of IS at Sainte-Justine University Hospital. These subjects are also included in Table III above.

Healthy children were recruited as controls in Montreal's elementary schools after an informed written consent was obtained from their parents or legal guardians; minors also gave their assent. This recruitment was approved by The Montreal English School Board, The Affluent School Board and all institutional review boards mentioned above. Each normal subject was also examined by the same orthopedic surgeon using Adam's forward bending-test with a scoliometer (Table IV) to rule out any hidden scoliosis before entering the study. These subjects are also included in Table I above.

TABLE IV

Summary of clinical characteristics of the AIS subjects presented in Examples 3-4 and 8-10.

| Subjects | Mean Age (Years) | Mean Single Scoliosis Cobb Angle (°) | | | Mean Double Scoliosis Cobb Angle (°) Thoracic + Lumbar | Heredity |
|---|---|---|---|---|---|---|
| | | Thoracic | Lumber | Thoracolumbar | | |
| IS severely affected (N = 19) | 14.8 ± 2.3 | 72 ± 21 | — | 59 ± 14 | 48.6 ± 18.9 (thoracic angle) 48.9 ± 14.8 (lumbar angle) | 4/19 |
| | | N = 11 | N = 0 | N = 2 | N = 2 | |
| IS moderately affected (N = 25) | 13.0 ± 2.2 | 18.8 ± 6.7 | 18.0 ± 2.8 | 15.7 ± 8.9 | 18.8 ± 9.4 (thoracic angle) 17.6 ± 11.3 (lumbar angle) | 8/25 |
| | | N = 7 | N = 2 | N = 7 | N = 8 | |
| Healthy control subjects (N = 42) | 14.1 ± 2.1 | — | — | — | — | 0 |
| At-risk control subjects (N = 30) | 10.2 ± 3.2 | — | — | — | — | 30/30 |

Example 2

Material and Methods

The response of $G_i$ protein-coupled receptors was investigated in various cell types (osteoblasts, myoblasts and PBMCs (including principally lymphocytes)) obtained from patients with clinically well-defined AIS and compared with an age- and gender-matched control subjects (not affected by a scoliosis).

Three populations were investigated: patients with IS, healthy controls without any family history of scoliosis, and asymptomatic offspring, born from at least one scoliotic parent, who are considered at-risk of developing scoliosis. A group of 44 patients with IS (19 AIS patients with curvatures greater than 45° and 25 AIS patients with curvatures between 10° and 29°) (Table II above), as well as 42 healthy control subjects (Table I above) and 30 asymptomatic children at-risk of developing scoliosis (Table III above) were recruited and examined every 6 months. All subjects were Caucasians.

Osteoblasts and Myoblasts

Bone specimens were obtained intraoperatively from vertebras (varying from T3 to L4 according to the surgical procedure performed), while with trauma cases used as non-scoliotic controls bone specimens were obtained from other anatomical sites (tibia or femur, and in one case from an iliac crest biopsy). Osteoblasts and myoblasts isolated as previously described (Moreau A, Wang D S, Forget S et al. Melatonin Signaling Dysfunction in Adolescent Idiopathic Scoliosis. *Spine* 2004; 29:1772-81; Azeddine et al., 2007 *Molecular determinants of melatonin signaling dysfunction in adolescent idiopathic scoliosis*. Clin Orthop Relat Res. 2007, 462:45-52), were cultured at 37° C./5% $CO_2$ in MEM supplemented with 10% fetal bovine serum (FBS) and 100 µg/mL streptomycin. Prior to the experiment, cells were seeded into the CELLKEY™ label-free cellular analysis system standard 96-well plates at a density of $5 \times 10^4$/well and grown for 24 h and incubated in standard conditions (37° C./5% $CO_2$). In some plates, Pertussis toxin (100 ng/mL, Sigma, Oakville, ON, Canada) treatment was performed 16 h before the CDS assay. Following overnight incubation, plates were placed onto the CELLKEY™ label-free cellular analysis system and growth medium was exchanged to assay buffer (Hanks, Balanced Salt Solution containing 20 mM HEPES and 0.1% BSA) before starting the experiment. Cells were then allowed to equilibrate at room temperature for 30 min. Pre-addition measurements were made for 5 min to obtain a baseline reading. Then, ligands (melatonin, 2-lodomelatonin, BP554 maleate, UK14304, IB-MECA and/or CB65) were added simultaneously to all 96 wells using an integrated fluidics system. Activation of endogenous receptors resulted in a change in impedance that started occurring immediately after fluid addition and mixing. The quick update rate (2 s.) of the CELLKEY™ label-free cellular analysis system allows detection of these immediate changes in impedance. Impedance measurements were collected for 10 min to 15 min at 28° C. after ligand addition to monitor cellular responses to ligand interaction and to generate CELLKEY™ label-free cellular analysis system response profiles that are characteristic of the signaling mechanisms used.

PBMCs

Blood samples were obtained from patients and control groups and collected in blood collection tubes containing EDTA and then centrifuged on a Ficoll-Plaque (GE Healthcare, Mississauga, ON, Canada) solution to obtain PBMCs (containing principally lymphocytes). PBMC fractions were preserved frozen in FBS with 10% DMSO and kept in liquid nitrogen until thawed and assayed. PBMCs were harvested from stock tissue culture flask and washed three times with assay buffer. Cells were isolated from the heparinized peripheral by ficoll-Hypaque density gradient centrifugation, and cultured in RPMI 1640 medium supplemented with 10% FBS, 100 µg/mL streptomycin and 1% of phytohemagglutinin. Following 48 h of incubation at 37° C./$CO_2$ cells were washed three times with assay buffer and seeded into the CELLKEY™ label-free cellular analysis system small 96-well plates. Typically, an average of $1 \times 10^5$ cells to $1.5 \times 10^5$ were added to each well and allowed to settle for 30 min at room temperature. This resulted in a single layer of cells on top of the electrodes. After the cells settled, the cell plate was placed on the instrument and experiments were initiated in the manner described below after the acquisition of 5 min of baseline measurements. All experiments were conducted at 28° C.

Cellular Dielectric Spectroscopy (CDS)

The response induced by the various ligands to their receptors was measured by cellular dielectric spectroscopy (CDS) using the CELLKEY™ label-free cellular analysis technology. (MDS Sciex, San Francisco, Calif., USA). The CELLKEY™ label-free cellular analysis system integrates a proprietary impedance measurement system, custom 96-well microliter plate, onboard 96-well fluidics, and environment control and custom acquisition and analysis software in a full solution package (MDS Sciex) that is compatible with commercially available robotic platforms. Small voltage at 24 frequencies, from 1 KHz to 10 MHz, is applied to a monolayer of cells settled in a 96-well microplate containing electrodes at the bottom, and the resultant current is measured at an update rate of 2 s. The system is thermally regulated and experiments can be conducted between 28 and 37° C., and for examples presented herein was typically 28° C. Onboard fluid additions and exchanges are handled by 96-well head fluid delivery device with a range of 5-500 µL. In addition to the cell plate location, the CELLKEY™ label-free cellular analysis system includes two additional stations for 96- or 384-well compound plates. All aspects of assay set up, execution, and data acquisition and analysis are controlled by CELLKEY™ label-free cellular analysis software.

Agonist and antagonist activity of natural or synthetic ligands may be accurately quantified under conditions of low receptor expression (when using primary and first passage cells derived from patients, for example) using the CELLKEY™ label-free cellular analysis technology.

cAMP Assay in Osteoblasts

Osteoblasts from patients with IS and control subjects were seeded in quadruplicate on 24-well plates ($1 \times 10^5$ cells per well) and tested as previously described (Moreau A, Wang D S, Forget S et al. Melatonin Signaling Dysfunction in Adolescent Idiopathic Scoliosis. *Spine* 2004; 29:1772-81). All assays were performed in duplicate.

Statistical Analysis

Three experiments in duplicate were carried out for each subject, and results are mean±SE of these measurements. The assay coefficient of variation was found typically less than 10%. All concentration response curves were analyzed by non-linear regression using the GRAPHPAD™ software (San Diego, Calif.). For statistical analysis, multiple comparisons were performed with One-way analysis of variance (ANOVA) followed by a post-hoc test of Newman-Keuls. Probability values less than 0.05 were taken as significant.

Data are presented as mean±SE. Multiple comparisons of means were performed with one-way analysis of variance (ANOVA) followed by a post-hoc test of Dunnett, using the GRAPHPAD™ Prism 4.0 software. Only P values <0.05 were considered significant.

Example 3

CDS Detecting Relative Part of Gi Protein-Mediated Pathway in Melatonin Signaling The ability of CDS to detect the relative part of the Gi protein-mediated pathway in melatonin signaling was determined by blocking this pathway with pertussis toxin (PTX). This toxin ADP-ribosylates the a subunit of the heterotrimeric Gi protein and thereby prevents its activity. The MG63 osteoblast cell line was serum-starved for 16 h in the absence or presence of 100 ng/mL of PTX to inhibit the $\alpha_i$ subunit of Gi protein. Cells were then stimulated with 10 µM of melatonin or iodomelatonin at 37° C. for 5 min. Cellular responses were measured with CELLKEY™ label-free cellular analysis system as described in the Material and Methods section.

Results presented in FIG. 1 show that the PTX treatment dramatically inhibits the cellular response measured by CDS in MG63 osteoblast cell line following stimulation with either melatonin or iodomelatonin. The inhibition extent was about 75% for melatonin and 90% for iodomelatonin, indicating the major effects Gi protein have on melatonin signaling measured by CDS.

Example 4

Comparison of Melatonin Impairment Measured by cAMP and CDS

Figure 2:
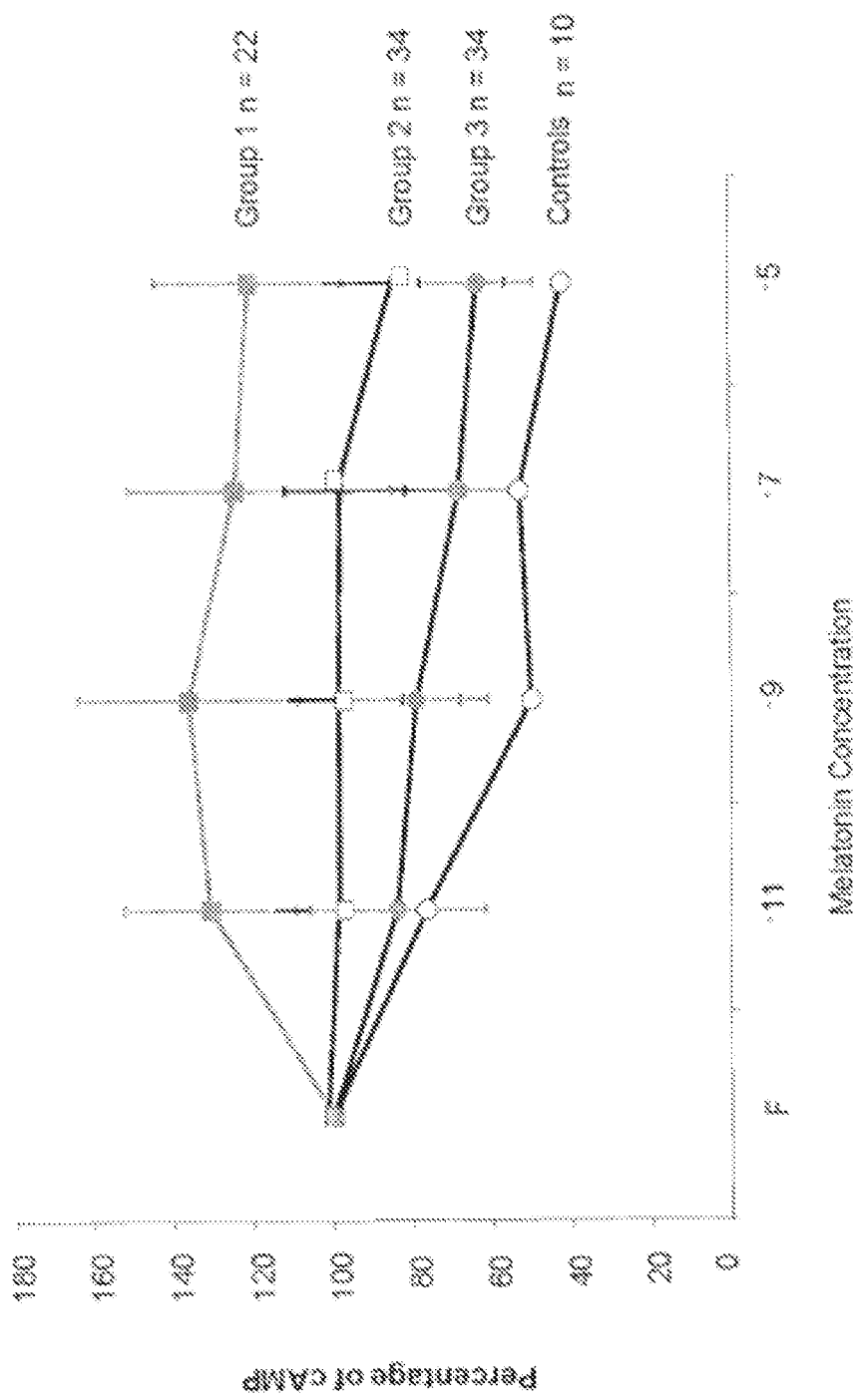
FIG. 2 shows osteoblasts from control subjects (non-IS) and patients with IS were pre-treated with forskolin to induce adenylate cyclase activity and subsequent cAMP production. Cells were then challenged with increasing concentration of melatonin and the functional status of melatonin signaling was estimated by the ability of melatonin to reduce cAMP levels. Data were normalized with cAMP production induced by forskolin in the absence of melatonin.
Figure 3A:
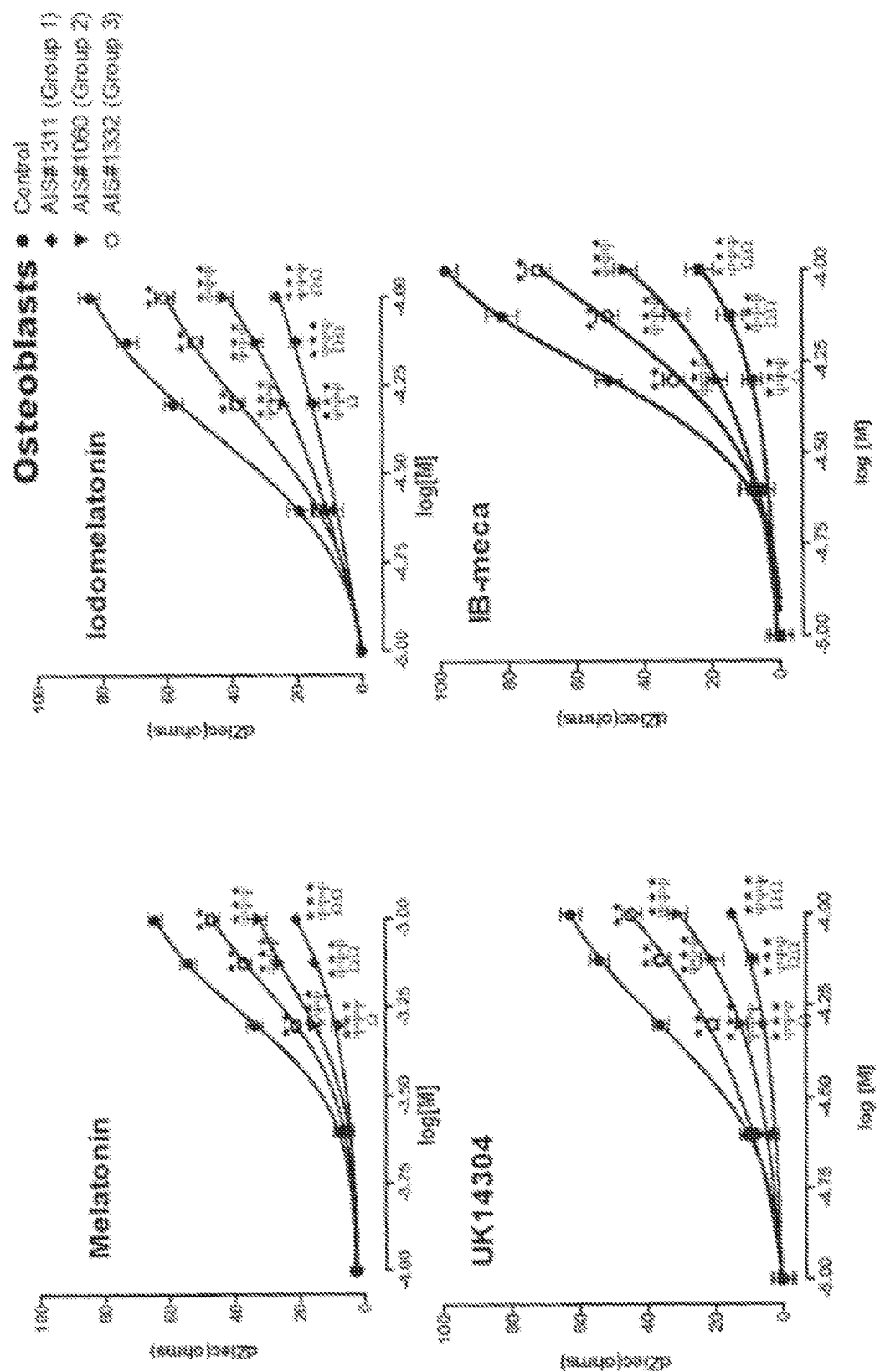
FIGS. 3A and 3B show the response of different receptors coupled to $G_i$ proteins expressed on osteoblasts obtained from AIS patients or control subjects following activation by a specific ligand, as measured by Cellular Dielectric Spectroscopy (CDS). Comparisons to control (*), Group 3 (Ψ) or Group 2 (Ω) are indicated by: *, Ψ, Ω, $p<0.05$; , ΨΨ, ΩΩ, $p<0.01$; *, ΨΨΨ, $p<0.001$.
Figure 3B:
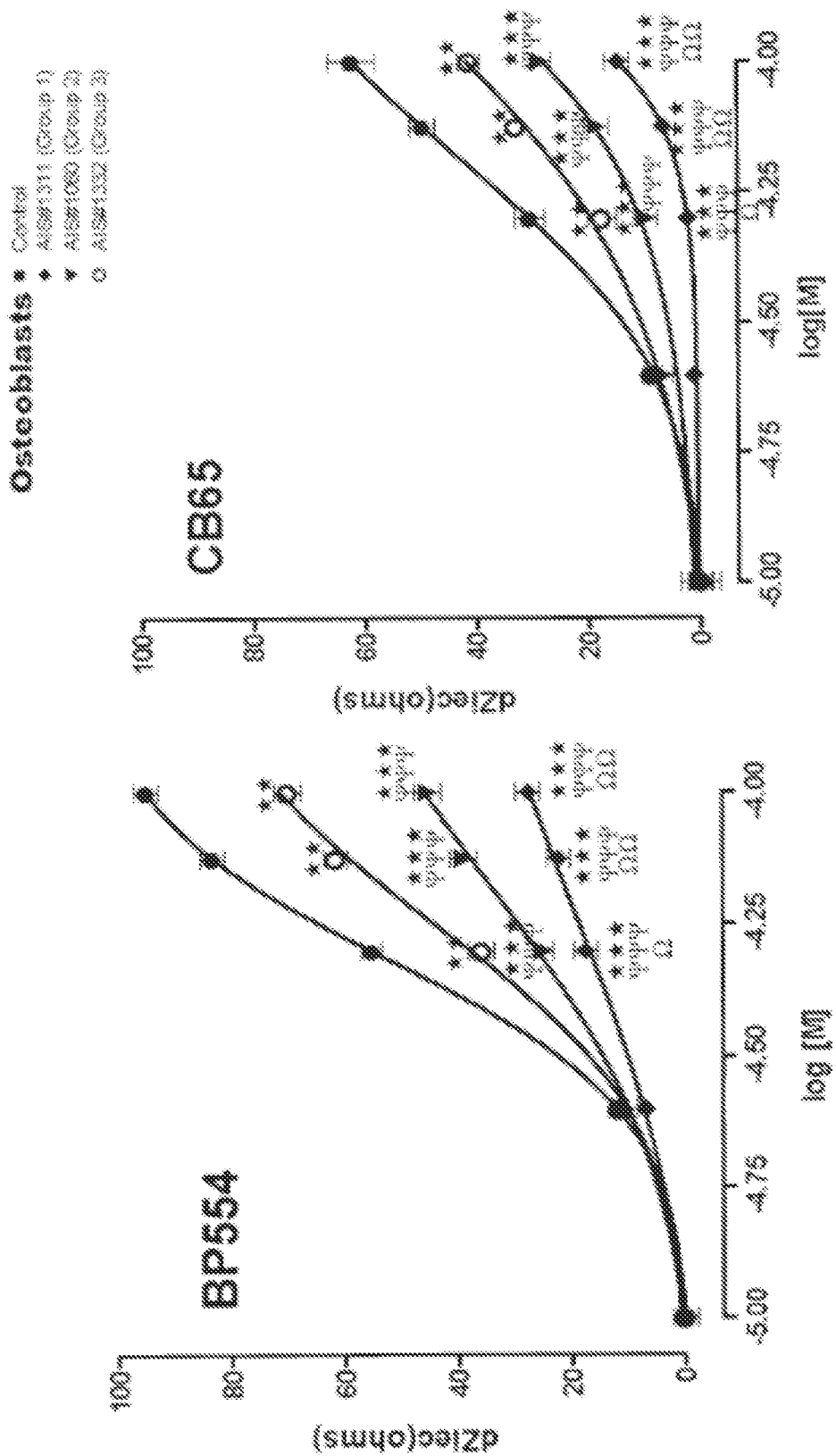

First osteoblasts derived from healthy controls and three severely affected IS patients (surgical cases exhibiting a Cobb's angle >45°) were pre-treated with forskolin to induce adenylate cyclase activity and subsequent cAMP production. Cells were then challenged with increasing concentration of melatonin and the functional status of melatonin signaling was estimated by the ability of melatonin to reduce cAMP levels. Data were normalized with cAMP production induced by forskolin in the absence of melatonin. As expected, osteoblasts from IS patients exhibited high cAMP production in response to melatonin subsequently to forskolin stimulation when compared to those from healthy control subjects (FIG. 2). Furthermore, the extent of this production was different between the three IS patients. These data are consistent with previous findings, (Goldberg M S, Mayo N E, Poitras B et al. The Ste-Justine Adolescent Idiopathic Scoliosis Cohort Study. Part I: Description of the study. *Spine* 1994; 19:1551-61.) thus confirming the occurrence of a melatonin signaling dysfunction of different degrees in the osteoblasts of these patients.

Figure 4A:
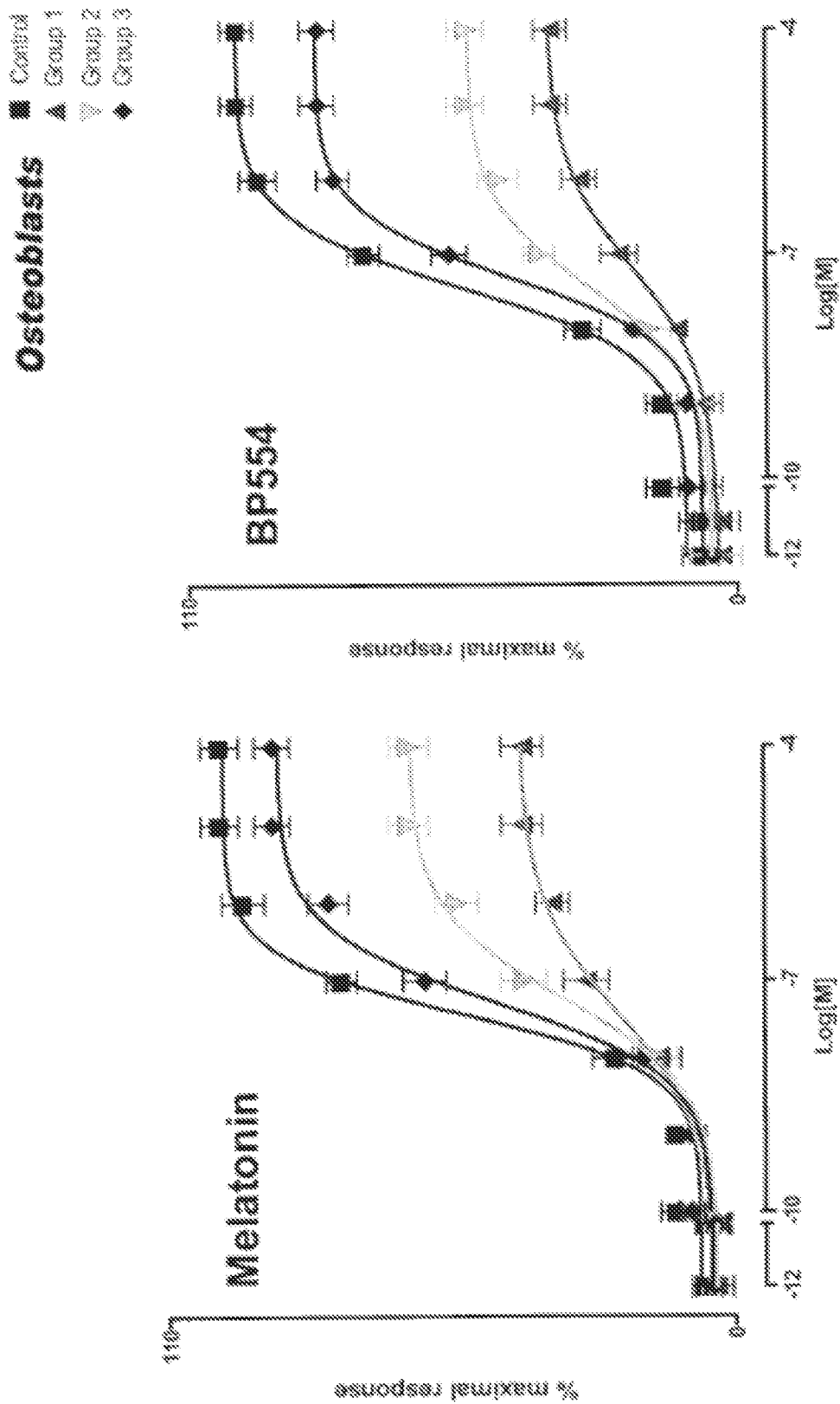
FIGS. 4A-4C compare Gi coupled protein signaling dysfunction using different ligands presented as percentage of maximal response measured by Cellular Dielectric Spectroscopy (CDS). Increasing concentrations of melatonin, iodomelatonin, BP554, UK14304, IB-meca and CB65 were applied to osteoblasts from control subject (non-IS) and patients with IS (Groups 1, 2 and 3). The subsequent cellular response was measured by CDS in the CELLKEY™ label-free cellular analysis instrument. Curves were generated from maximum impedance magnitude. Data were normalized to maximal response in cells from control patients, and are expressed as mean±SE of three independent experiments performed in duplicate.
Figure 4B:
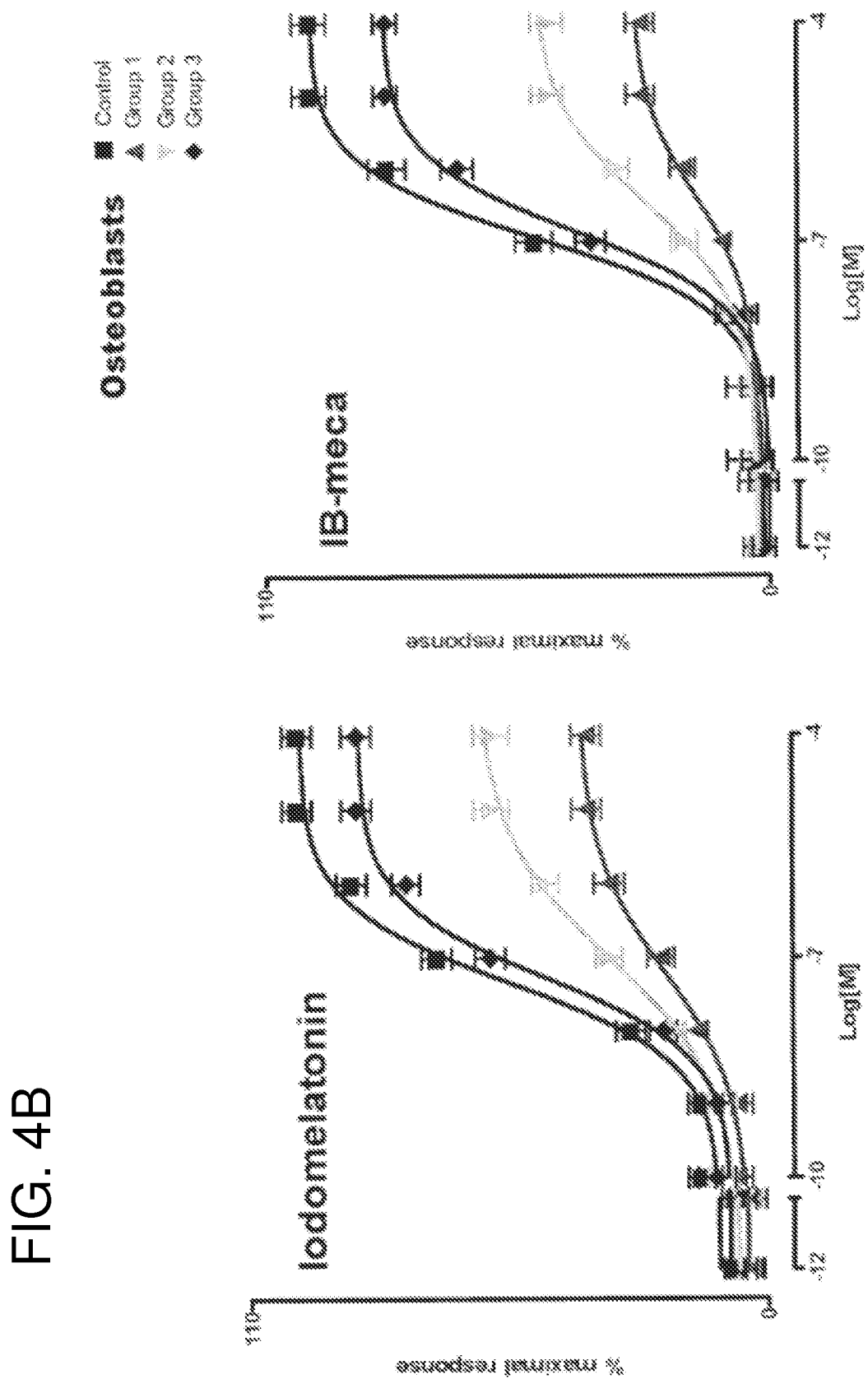
Figure 4C:
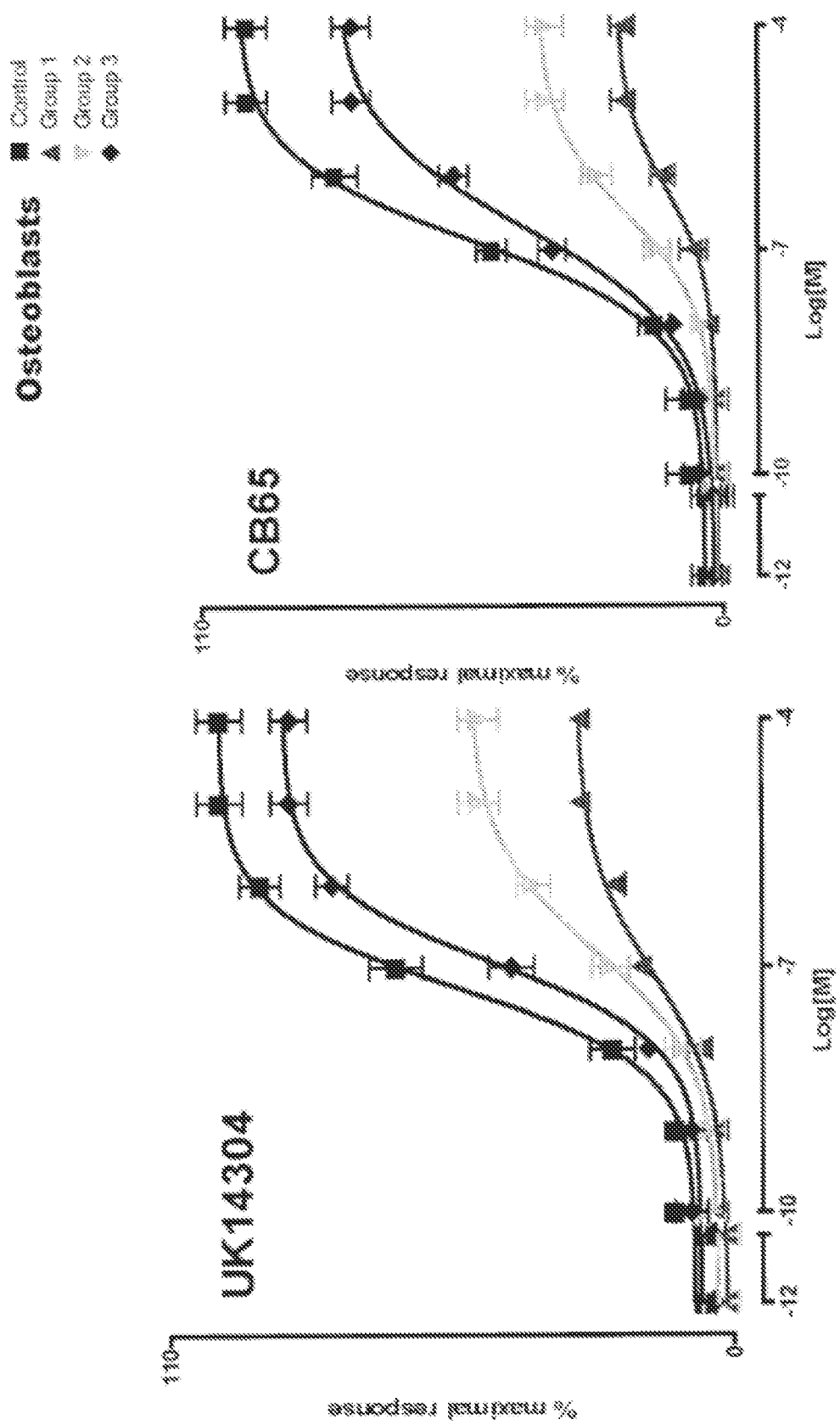
Figure 5A:
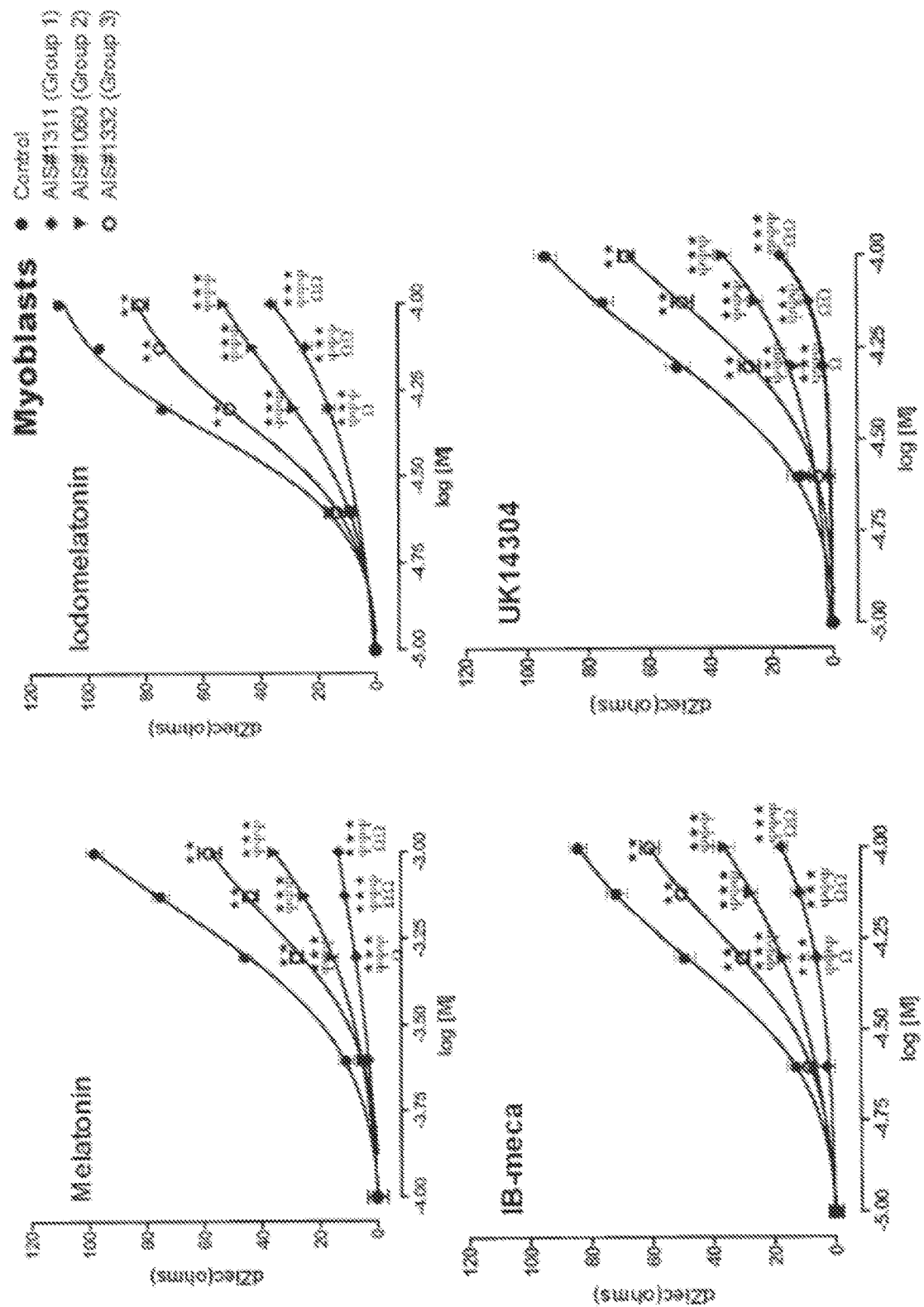
FIGS. 5A and 5B show the response of different receptors coupled to $G_i$ proteins expressed on myoblasts obtained from AIS patients or control subject following activation by a specific ligand, as measured by Cellular Dielectric Spectroscopy (CDS). Comparisons to control (*), Group 3 (Ψ) or Group 2 (Ω) are indicated by: *, Ψ, Ω, p<0.05; , ΨΨ, ΩΩ, p<0.01; *, ΨΨΨ, p<0.001.
Figure 5B:
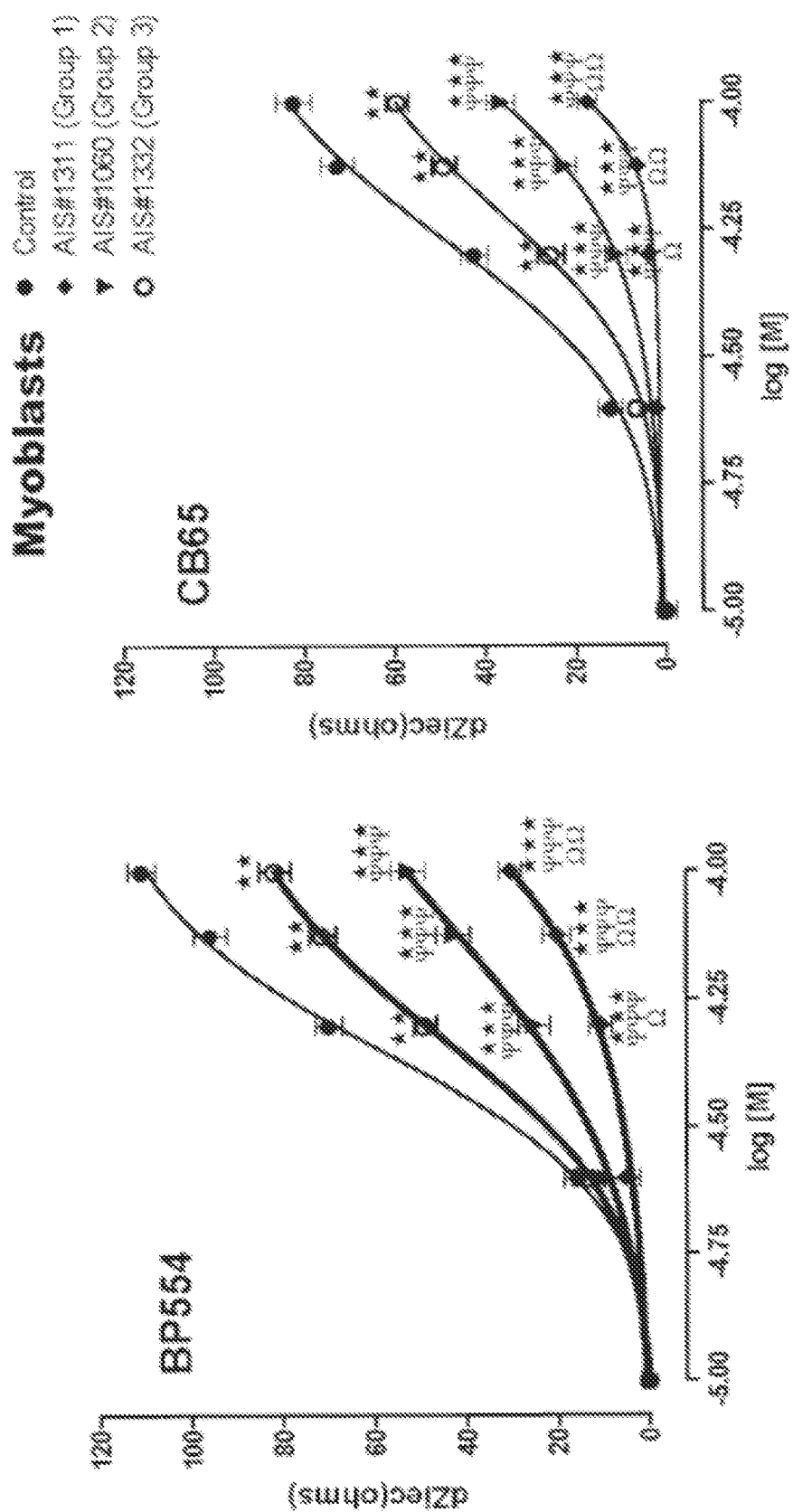
Figure 6A:
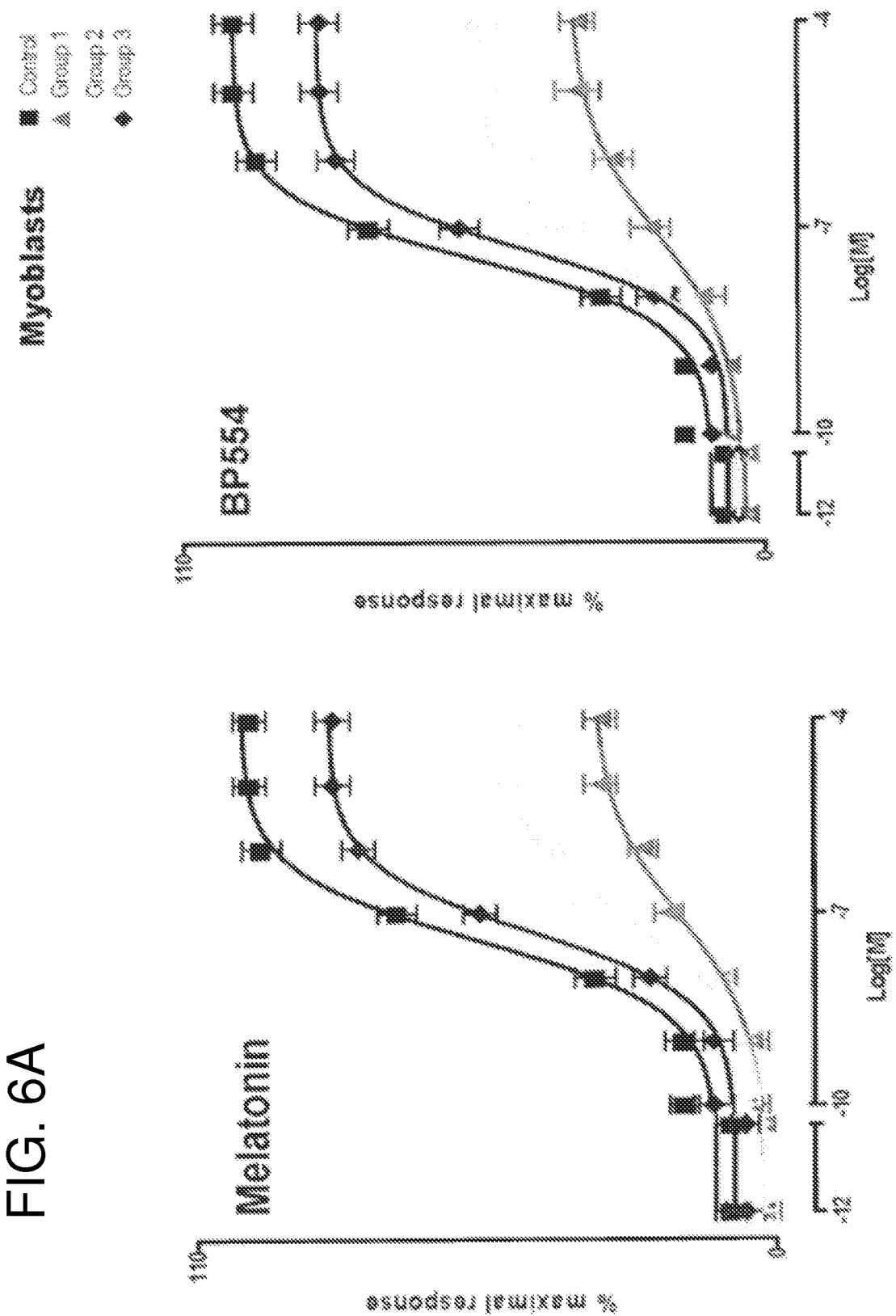
FIGS. 6A-6C compare Gi coupled protein signaling dysfunction using different ligands presented as percentage of maximal response measured by Cellular Dielectric Spectroscopy (CDS). Increasing concentrations of melatonin, iodomelatonin, BP554, UK14304, IB-meca and CB65 were applied to myoblasts from control subject (non-IS) and patients with IS (Groups 1, 2 and 3). The subsequent cellular response was measured by CDS in the CELLKEY™ label-free cellular analysis instrument. Curves were generated from maximum impedance magnitude. Data were normalized to maximal response in cells from control patients, and are expressed as mean±SE of three independent experiments performed in duplicate.
Figure 6B:
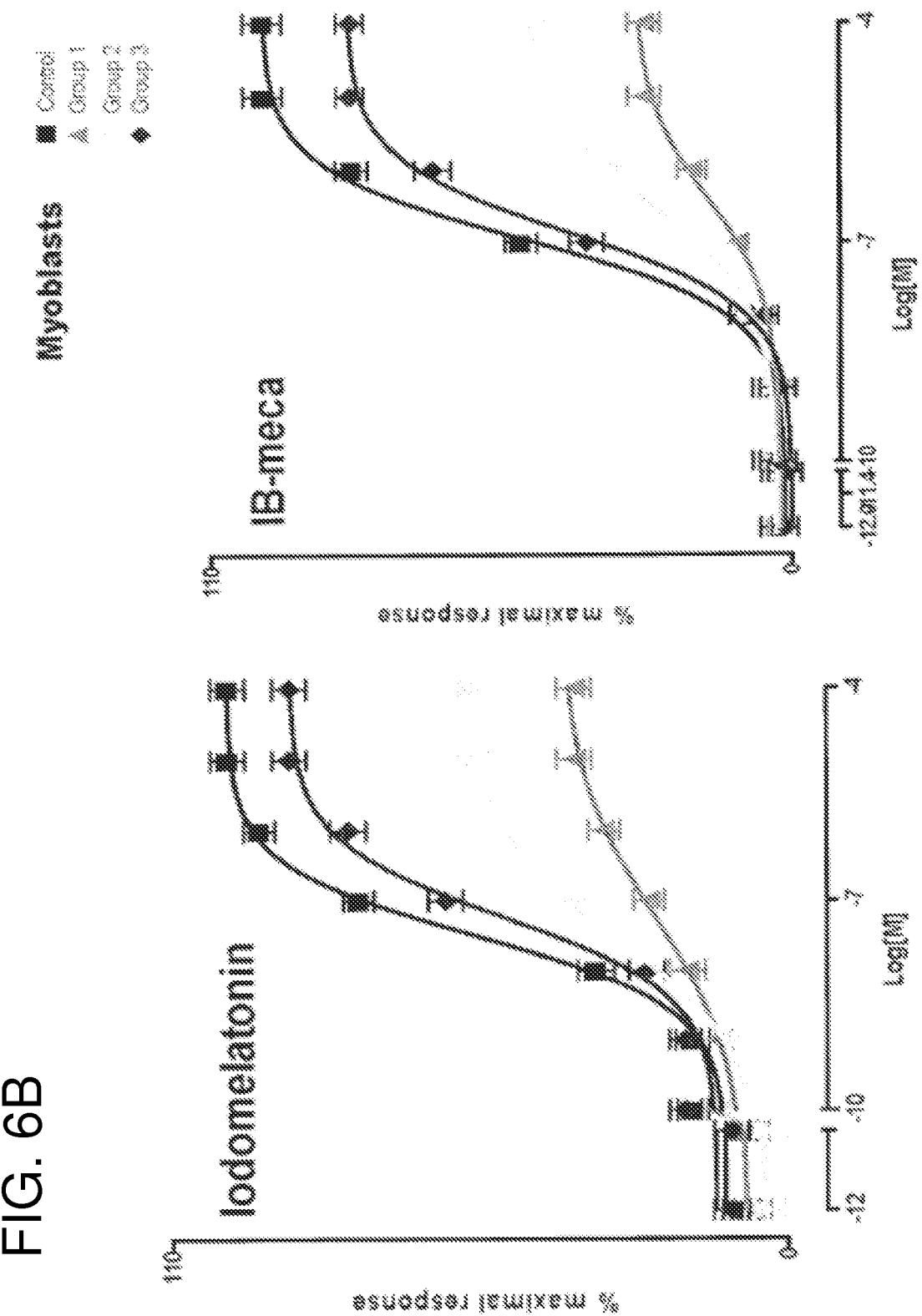
Figure 6C:
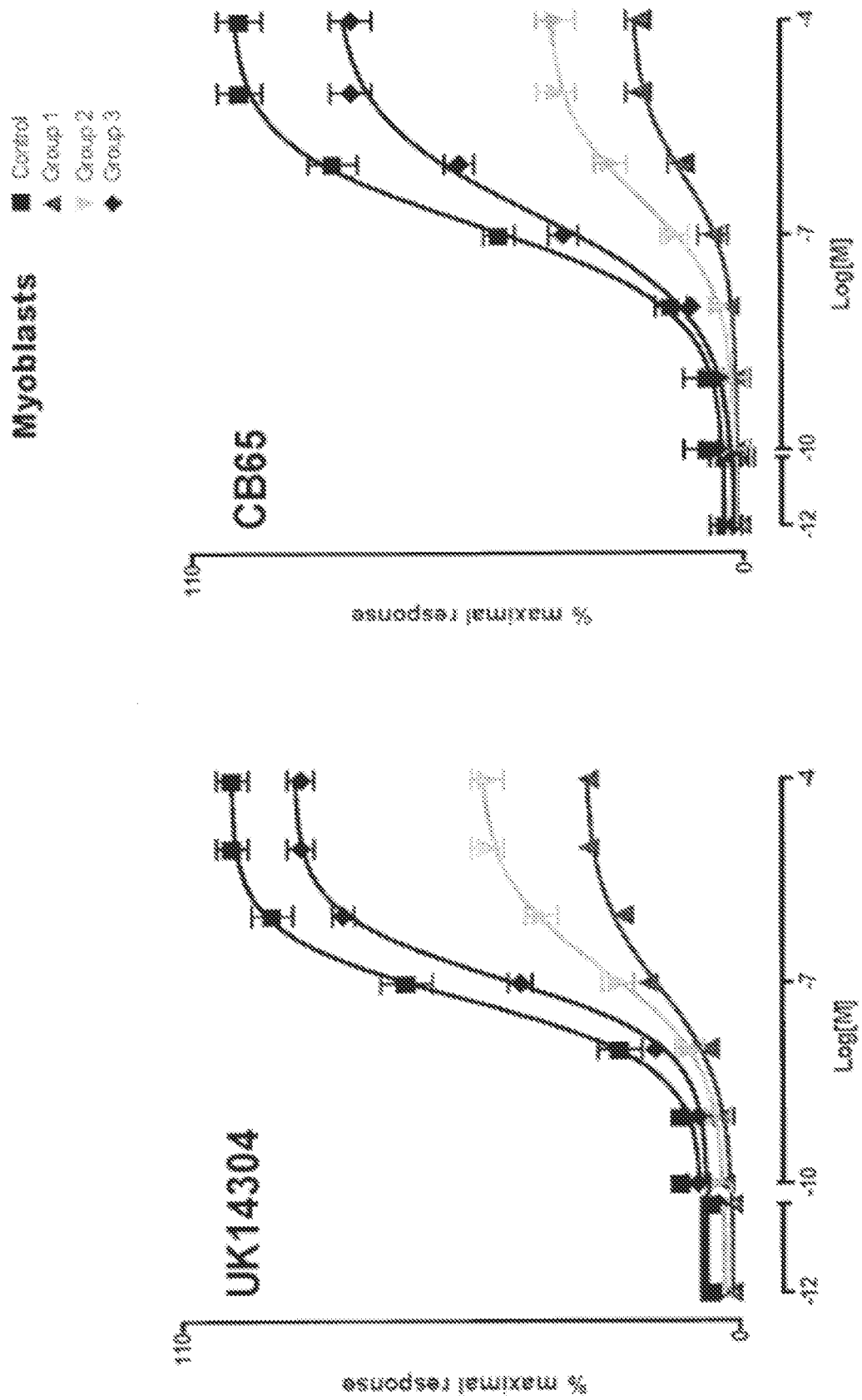
Figure 7A:
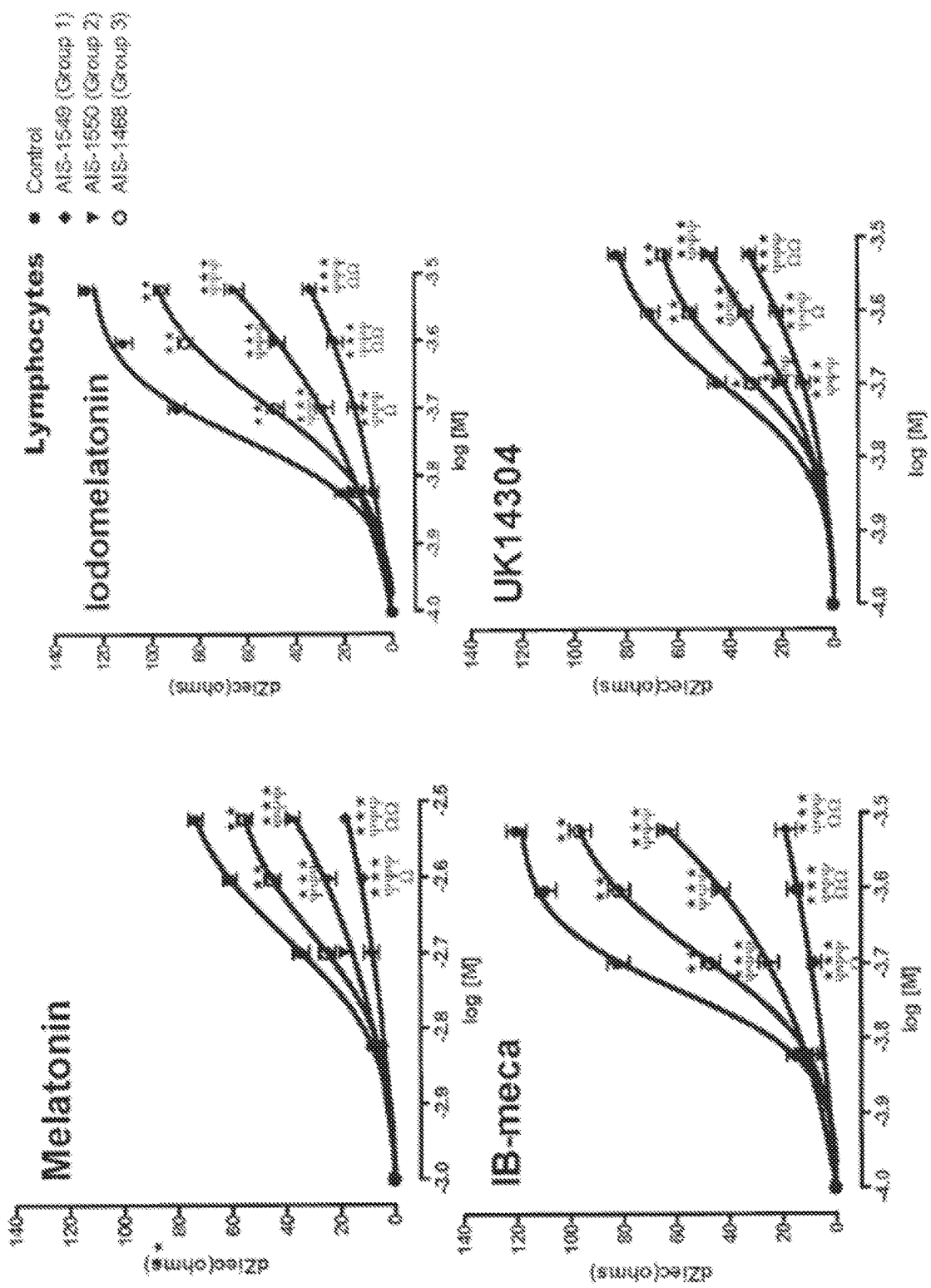
FIGS. 7A and 7B show the response of different receptors coupled to $G_i$ proteins expressed on PBMCs obtained from AIS patients or control subjects following activation by a specific ligand, as measured by Cellular Dielectric Spectroscopy (CDS). Comparisons to control (*), Group 3 (Y) or Group 2 (0) are indicated by: *, Ψ, Ω, p<0.05; , ΨΨ, ΩΩ, p<0.01; *, ΨΨΨ, p<0.001.
Figure 7B:
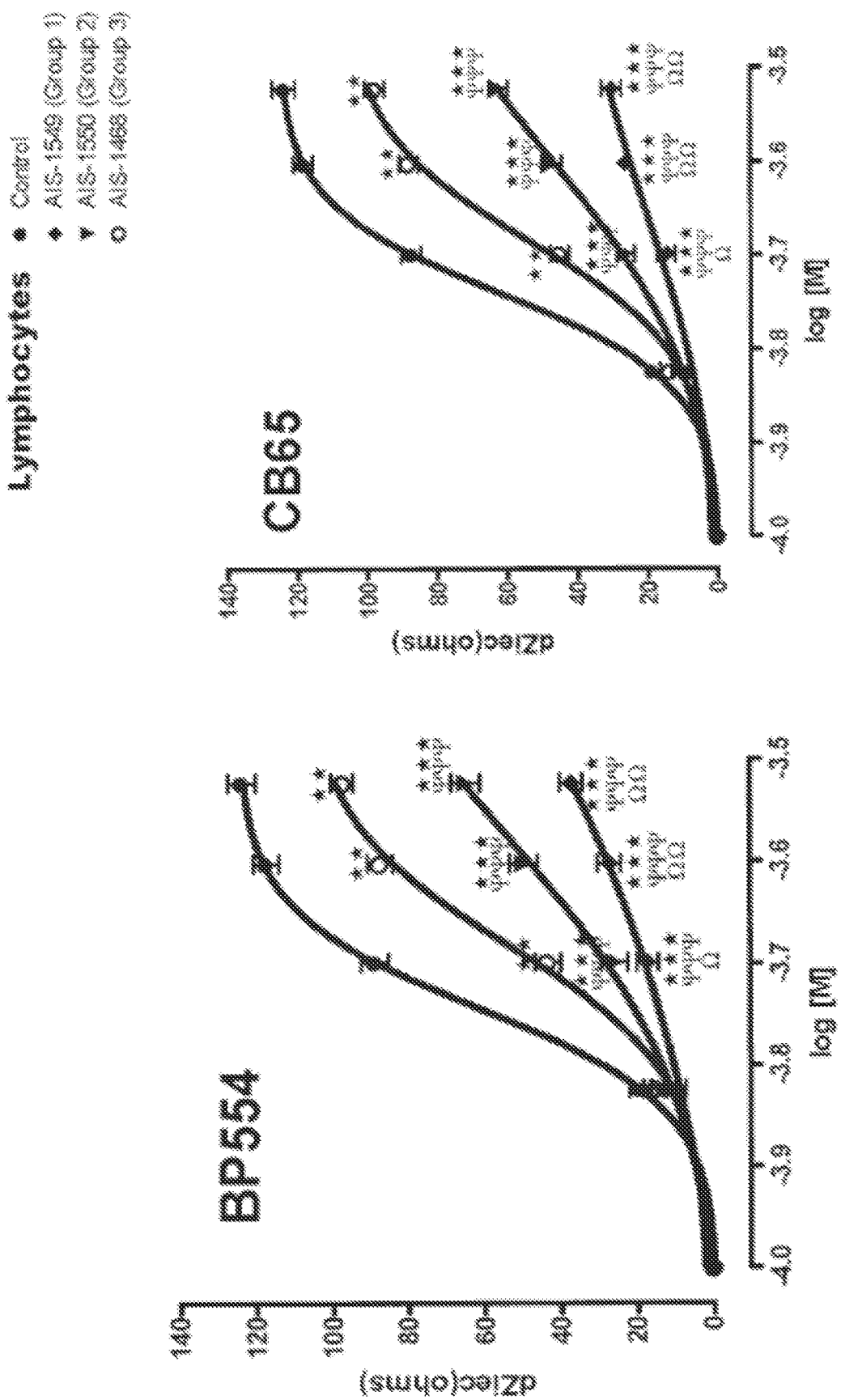
Figure 8A:
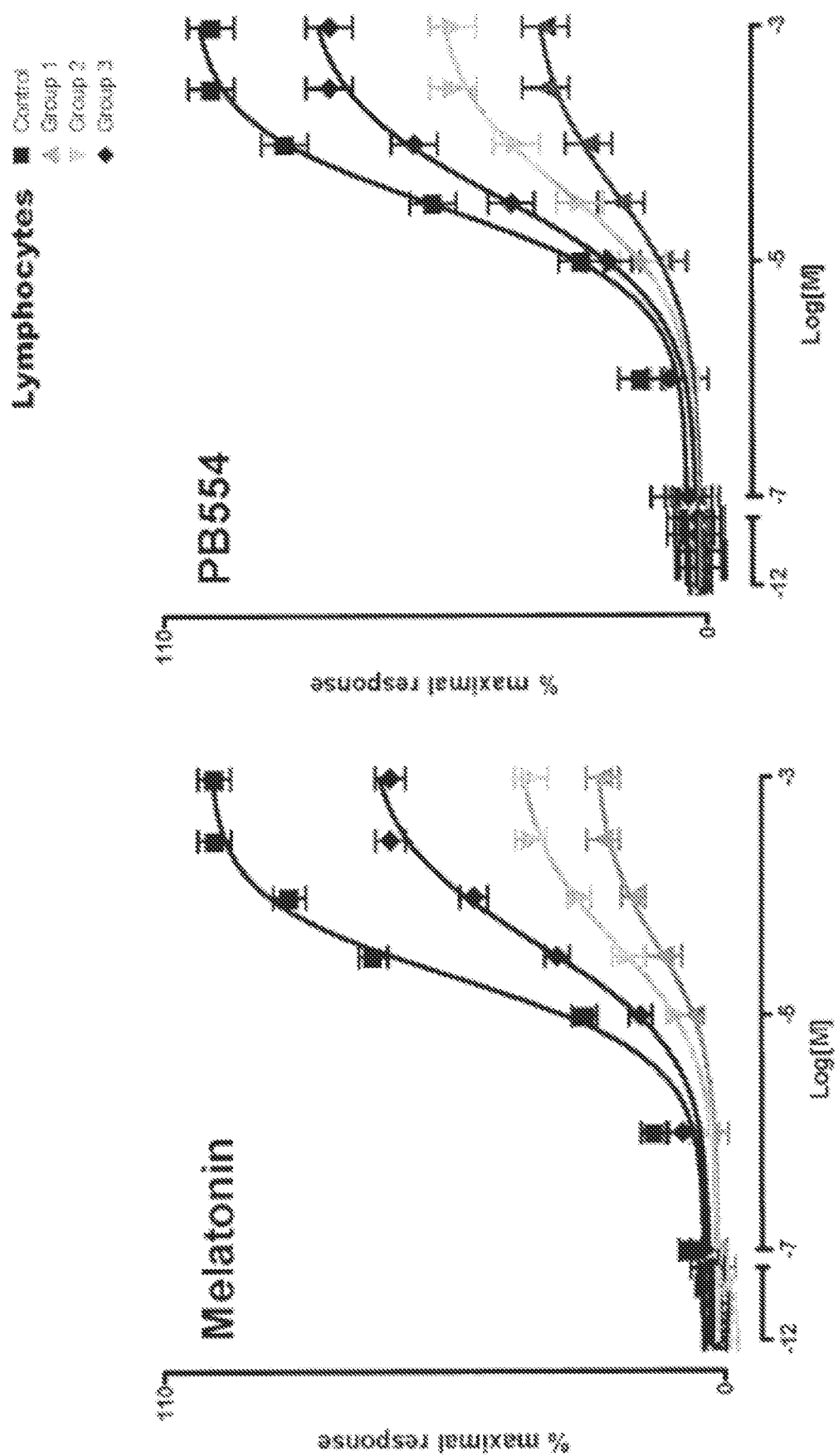
FIGS. 8A-8C compare Gi coupled protein signaling dysfunction using different ligands presented as percentage of maximal response measured by Cellular Dielectric Spectroscopy (CDS). Increasing concentrations of melatonin, iodomelatonin, BP554, UK14304, IB-meca and CB65 were applied to PBMCs (containing principally lymphocytes) from control subjects (non-IS) and patients with IS (Groups 1, 2 and 3). The subsequent cellular response was measured by CDS in the CELLKEY™ label-free cellular analysis instrument. Curves were generated from maximum impedance magnitude. Data were normalized to maximal response in cells from control patients, and are expressed as mean±SE of three independent experiments performed in duplicate.
Figure 8B:
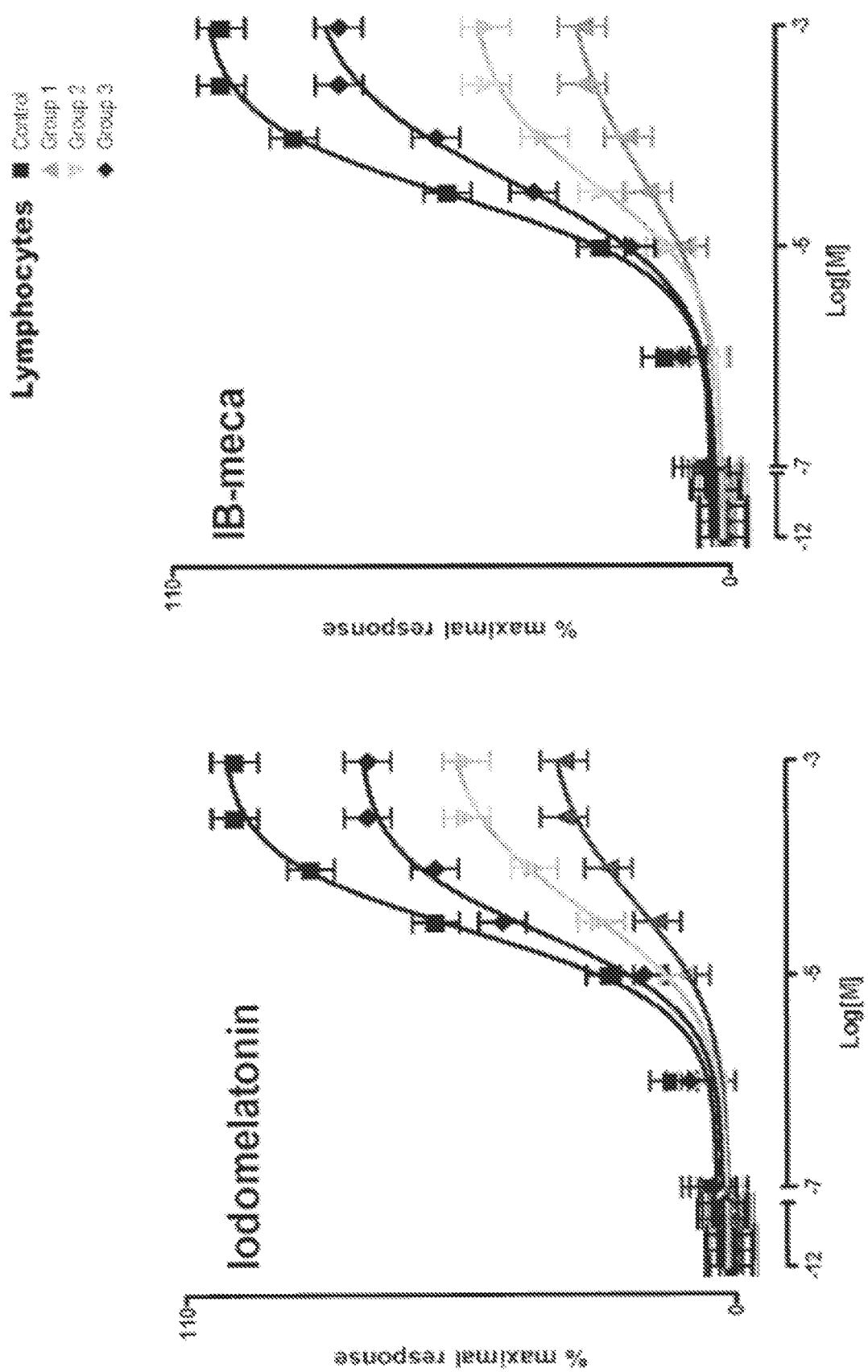
Figure 8C:
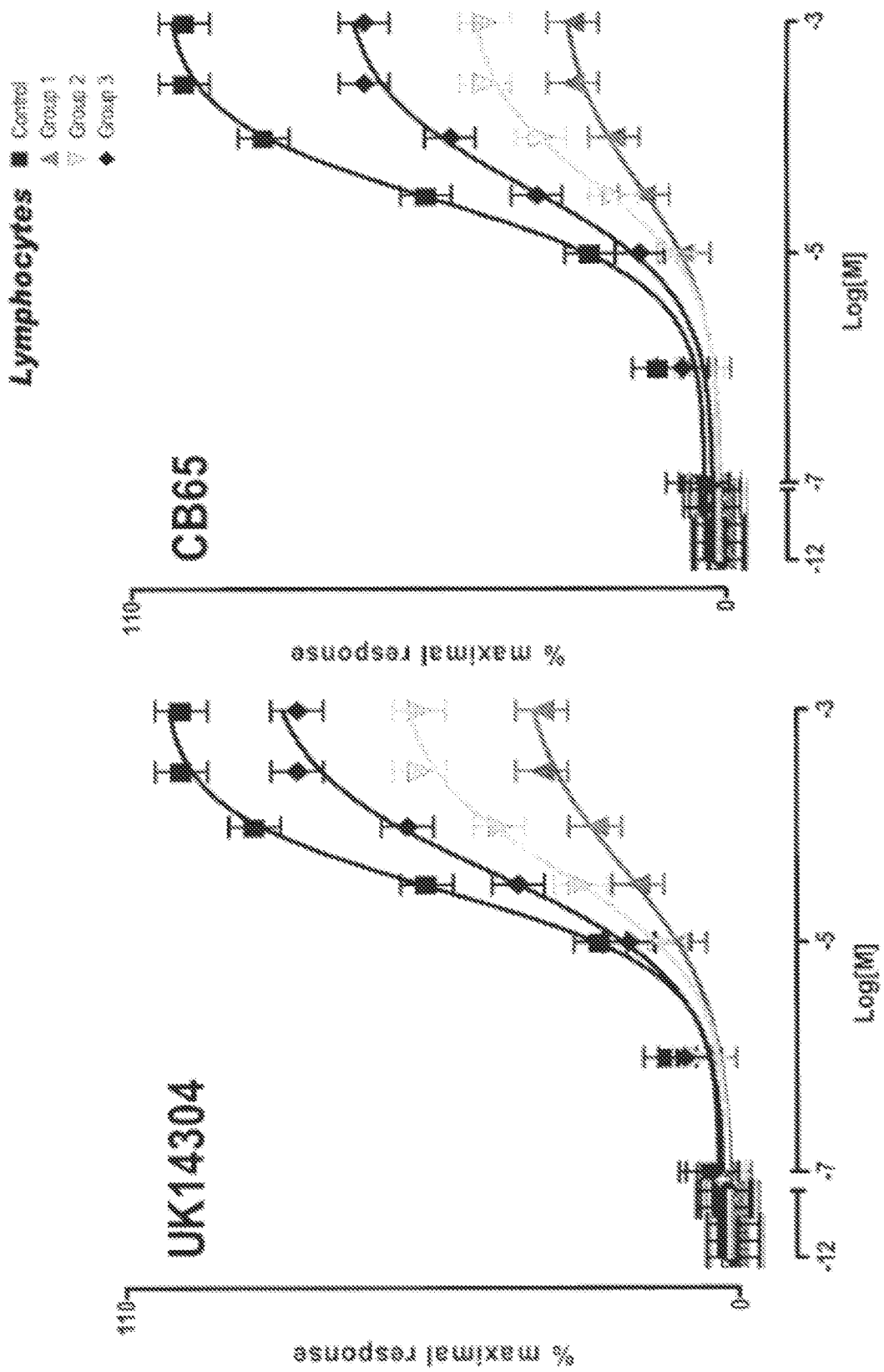
Figure 11A:
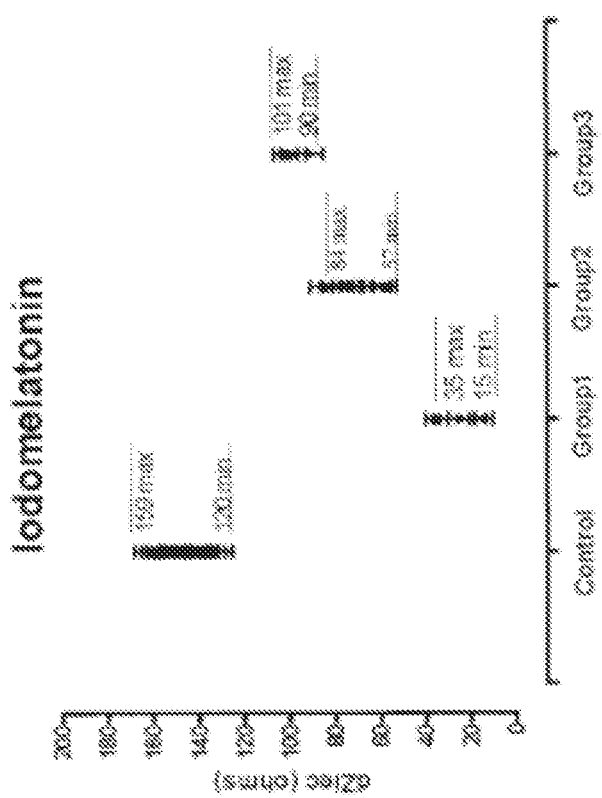
Figure 11B:
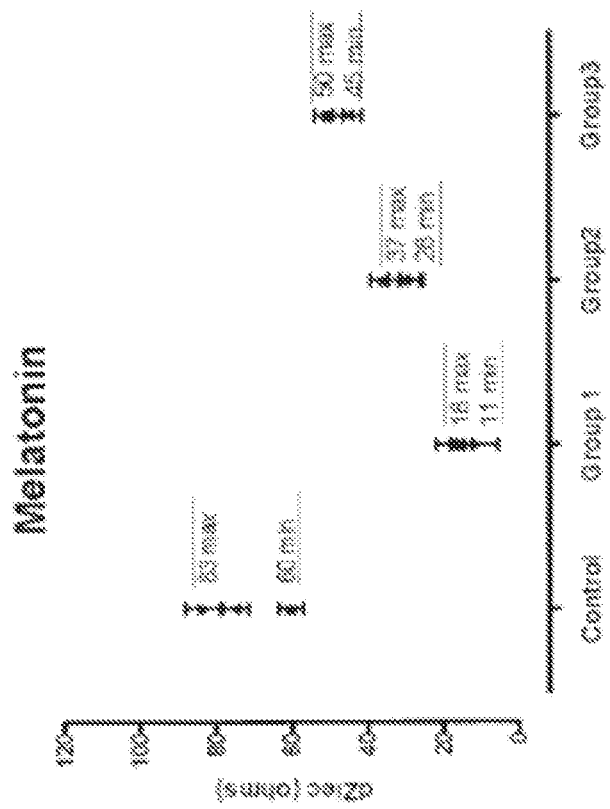
Figure 11D:
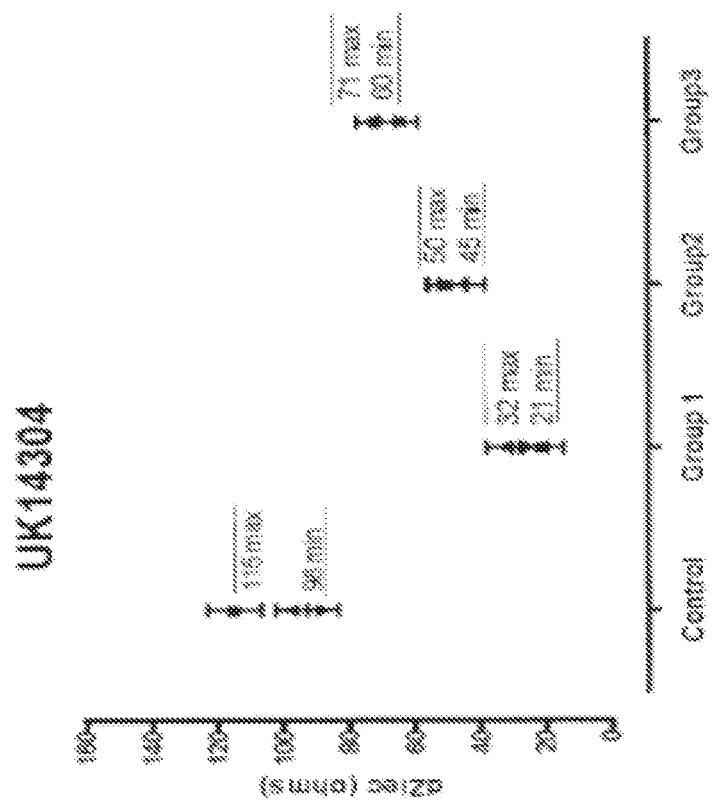
Figure 11C:
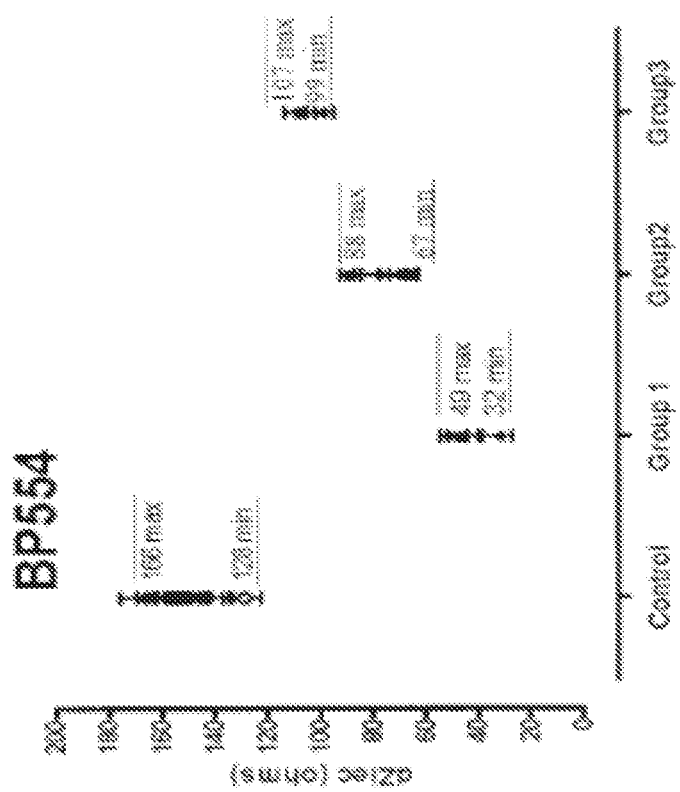

The ability of a CDS assay to detect this defect was then assessed by studying the effect of various concentrations of melatonin and iodomelatonin on CDS response of these cells. Increasing concentrations of melatonin or iodomelatonin were applied to osteoblasts and PBMCs (including principally lymphocytes) from healthy control subjects (Control) and patients with IS (Groups 1, 2 and 3). The subsequent cellular response was measured by CDS in the CELLKEY™ label-free cellular analysis instrument. Curves were generated from maximum impedance magnitude. Data were normalized to maximal response in cells from control patients, and were expressed as mean±SE of three independent experiments performed in duplicate. Results obtained showed that melatonin and iodomelatonin evoked similar responses in a concentration-dependent manner in osteoblasts from both control and IS patients. However, the magnitude of response was significantly lower in IS osteoblasts (FIGS. 4A-4C). On the other hand, a significant difference in the extent of CDS response was also observed between the three IS patients. These results indicate that the dysfunction of melatonin signaling in IS and the disparity of this defect among patients can be detected by CDS in IS patients.

Interestingly, the screening of PBMCs in response to melatonin or iodomelatonin, using CDS, revealed similar features than those obtained with osteoblasts (FIGS. 4A-4C and 8A-8C), demonstrating that melatonin signaling dysfunction also occurs in PBMCs.

Example 5

Comparison of the Response of Different Gi-Coupled Receptors in Various Cell Types Isolated from IS Vs. Control Subjects As shown in FIGS. 3 to 8, osteoblasts, myoblasts and PBMCs isolated from AIS patients and stimulated with ligands specific for different Gi-protein coupled receptors (MT2, 5-HT1A, α2-AD, A3 or CB2) have an altered response (i.e. change in impedance following stimulation) as compared to that of cells from a normal, non-scoliotic subject, thus demonstrating that IS patients have a generalized impairment in Gi-protein-mediated signaling. As shown in Table V below, an impaired Gi-protein coupled receptor response was measured in cells from all IS subjects (phase I and phase II) tested. Also, cells from 12/31 asymptomatic at risk subjects (subjects having an IS parent) showed a defect in Gi-protein coupled receptor response. Interestingly, 4 out of the 12 subjects in which impaired Gi-protein coupled receptor response was detected later developed symptoms of scoliosis, as determined by X-rays analysis, demonstrating that the impaired/defective Gi-protein coupled receptor response may be used for the prognosis of IS (or of a predisposition to developing IS).

TABLE V

Summary of data obtained with control, AIS and asymptomatic at risk subjects

| Patients | Healthy Control | Asymptomatic at risk | AIS Phase II (10°-44°) | AIS Phase I (≥45°) |
| --- | --- | --- | --- | --- |
| Total number | 42 | 31 | 25 | 14 |
| Unaffected | 100% | 62% (19/31) | 0 | 0 |
| Affected | 0% | 38% (12/31) | 100% | 100% |
| Group 1 | 0% | 3% (1/31) | 4% (1/25) | 21% (3/14) |
| Group 2 | 0% | 6% (2/31) | 32% (8/25) | 21% (3/14) |
| Group 3 | 0% | 29% (9/31) | 64% (16/25) | 58% (8/14) |

Example 6

Measurement of Gi-Coupled Receptor Responses in Cells Obtained from Members of an AIS Family FIGS. 9-10 show that an altered response of different Gi-coupled receptors is detected in PBMCs (including principally lymphocytes) isolated from both the IS affected mother and daughter, but not in cells from the unaffected father and son. Interestingly, the Gi-coupled receptor responses measured in cells obtained from the mother and daughter are very similar (Group 2, as defined below), suggesting that the defect has been genetically transmitted by the mother to the daughter. Also, the defect is maintained in the mother although she underwent surgery to reduce spine curvature. The clinical data for the daughter are as follows: Age 13.5, curve pattern: right thoracic, Cobb angle: 6.

Example 7

Stratification/Classification of AIS Subjects Based on Gi-Coupled Receptor Responses Measured in Osteoblasts FIGS. 11A-11F show the range of mean values obtained for control (n=3) and IS subjects (n=9) using the different Gi-coupled receptor ligands as measured in osteoblasts. The minimal (min) and maximal (max) values represent the mean of three independent measurements performed in duplicate (six values in total) for a given patient/control subject. All AIS subject tested showed a lower Gi-coupled receptor response as compared to control subjects, but it was observed that AIS subjects typically show three types of response (as represented by the three different curves for AIS subjects in FIGS. 3 to 8), and thus may be classified into three groups. AIS subjects having the lowest values (low $G_i$-coupled receptor response) were classified as subgroup 1, AIS subject having the highest values ("high" $G_i$-coupled receptor response, but always lower than control subjects) were classified as subgroup 3, and AIS subjects having values between those of Groups 1 and 3 ("intermediate" $G_i$-coupled receptor response) were classified as subgroup 2. The data (dZiec values and % of control) obtained using various ligands are summarized in Table VI below. Duplicates (n1 and n2) of three independent experiments are presented.

TABLE VI

Stratification/classification of AIS subjects based on Gi-coupled receptor responses

| | dZiec values/% of control | | | | | |
|---|---|---|---|---|---|---|
| | Exper. 1 | | Exper. 2 | | Exper. 3 | |
| Subject | n1 | n2 | n1 | n2 | n1 | n2 |
| Melatonin | | | | | | |
| CTR#60 | 55.81/— | 53.31/— | 63.72/— | 67.72/— | 59.25/— | 61.03/— |
| AIS#1474 | 16.53/29.6% | 13.03/24.4% | 15.18/23.8% | 15.18/22.4% | 17.34/29.3% | 16.12/26.4% |
| AIS#1550 | 28.28/50.7% | 30.78/57.7% | 29.43/46.2% | 32.43/47.9% | 29.34/49.5% | 31.12/51% |
| AIS#1020 | 29.38/52.6% | 31.88/59.8% | 40.33/63.3% | 39.33/58.1% | 34.34/58% | 36.12/59.2% |
| CTR#61 | 68.79/— | 66.29/— | 80.84/— | 84.84/— | 74.30/— | 76.08/— |
| AIS#1549 | 17.30/25.1% | 16.80/25.3% | 18.41/22.8% | 20.41/24.1% | 17.34/23.3% | 19.12/25.1% |
| AIS#1468 | 44.92/65.3% | 46.42/70% | 54.79/67.8% | 54.79/64.6% | 49.34/66.4% | 51.12/67.2% |
| AIS#1513 | 38.90/56.5% | 39.40/59.4% | 50.81/62.9% | 51.81/61.1% | 44.34/59.7% | 46.12/60.6% |
| CTR#69 | 76.12/— | 73.62/— | 89.58/— | 93.58/— | 82.34/— | 84.12/— |
| AIS#1488 | 9.79/12.9% | 11.29/15.3% | 10.91/12.2% | 10.91/11.7% | 12.34/15% | 12.12/14.4% |
| AIS#1198 | 23.94/39.3% | 31.44/42.7% | 31.91/35.6% | 25.91/27.7% | 27.41/33.3% | 29.19/34.7% |
| AIS#1385 | — | — | — | — | — | — |
| Iodomelatonin | | | | | | |
| CTR#60 | 142.55/— | 139.55/— | 149.20/— | 161.20/— | 152.18/— | 142.58/— |
| AIS#1474 | 33.02/23.2% | 32.02/23.0% | 38.33/25.7% | 32.33/20.1% | 39.97/26.3% | 36.37/25.5% |
| AIS#1550 | 55.99/39.3% | 48.99/35.1% | 60.90/40.8% | 62.90/39.0% | 62.74/41.2% | 59.14/41.5% |
| AIS#1020 | 69.57/48.8% | 66.57/47.7% | 85.25/57.1% | 97.25/60.3% | 83.71/55.0% | 74.11/52.0% |
| CTR#61 | 130.88/— | 127.88/— | 138.31/— | 150.31/— | 140.90/— | 131.30/— |
| AIS#1549 | 9.21/7.0% | 6.21/4.9% | 18.70/13.5% | 20.70/13.8% | 20.25/14.4% | 20.65/15.7% |
| AIS#1468 | 91.38/69.8% | 88.38/69.1% | 101.69/73.5% | 113.69/75.6% | 102.83/73.0% | 93.23/71.0% |
| AIS#1513 | 83.92/64.1% | 80.92/63.3% | 94.08/68.0% | 106.08/70.6% | 95.30/67.6% | 85.70/65.3% |
| CTR#69 | 150.99/— | 147.99/— | 161.10/— | 173.10/— | 162.34/— | 152.74/— |
| AIS#1488 | 25.43/16.8% | 27.43/18.5% | 30.31/18.8% | 27.31/15.8% | 19.17/11.8% | 19.57/12.8% |
| AIS#1198 | 61.05/40.4% | 61.05/41.3% | 65.29/40.5% | 70.29/40.6% | 60.97/37.6% | 57.37/37.6% |
| AIS#1385 | 66.51/44.1% | 67.51/45.6% | 79.93/49.6% | 81.93/47.3% | 79.02/48.7% | 69.42/45.4% |
| IB-meca | | | | | | |
| CTR#60 | 148.22/— | 160.22/— | 172.73/— | 180.73/— | 161.48/— | 169.48/— |
| AIS#1474 | 31.25/21.1% | 30.25/18.9% | 36.61/21.2% | 37.61/20.8% | 29.93/18.5% | 37.93/22.4% |
| AIS#1550 | 65.47/44.2% | 67.47/42.1% | 81.23/47.0% | 79.23/43.8% | 69.35/42.9% | 77.35/45.6% |
| AIS#1020 | 74.19/50.1% | 76.19/47.6% | 87.32/50.6% | 85.32/47.2% | 76.76/47.5% | 84.76/50.0% |
| CTR#61 | 127.27/— | 139.27/— | 155.44/— | 163.44/— | 142.36/— | 150.36/— |
| AIS#1549 | 5.11/4.0% | 17.11/12.3% | 26.78/17.2% | 34.78/21.3% | 16.94/11.9% | 24.94/16.6% |
| AIS#1468 | 98.77/77.6% | 110.77/79.5% | 121.90/78.4% | 129.90/79.5% | 111.34/78.2% | 119.34/79.4% |
| AIS#1513 | 78.36/61.6% | 90.36/64.9% | 104.12/67.0% | 112.12/68.6% | 92.24/64.8% | 100.24/66.7% |
| CTR#69 | 154.52/— | 166.52/— | 179.10/— | 187.10/— | 167.81/— | 175.81/— |
| AIS#1488 | 39.34/25.5% | 41.34/24.8% | 47.91/26.8% | 45.91/24.5% | 39.63/23.6% | 47.63/27.1% |
| AIS#1198 | 63.58/41.1% | 75.58/45.4% | 85.63/47.8% | 93.63/50.0% | 75.61/45.1% | 83.61/47.6% |
| AIS#1385 | 73.49/47.6% | 75.49/45.3% | 85.15/47.5% | 83.15/44.4% | 75.32/44.9% | 83.32/47.4% |
| CB65 | | | | | | |
| CTR#60 | 143.28/— | 155.28/— | 173.77/— | 181.77/— | 159.53/— | 167.53/— |
| AIS#1474 | 36.30/25.3% | 38.30/24.7% | 46.79/26.9% | 44.79/24.6% | 37.55/23.5% | 45.55/27.2% |

TABLE VI-continued

Stratification/classification of AIS subjects based on Gi-coupled receptor responses

| | dZiec values/% of control | | | | | |
|---|---|---|---|---|---|---|
| | Exper. 1 | | Exper. 2 | | Exper. 3 | |
| Subject | n1 | n2 | n1 | n2 | n1 | n2 |
| AIS#1550 | 55.13/38.5% | 57.13/36.8% | 66.49/38.3% | 64.49/35.5% | 56.81/35.6% | 64.81/38.7% |
| AIS#1020 | 61.81/43.1% | 73.81/47.5% | 74.95/43.1% | 82.95/45.6% | 69.38/43.5% | 77.38/46.2% |
| CTR#61 | 144.08/— | 156.08/— | 168.59/— | 176.59/— | 157.34/— | 165.34/— |
| AIS#1549 | 36.48/25.3% | 28.48/18.2% | 32.23/19.1% | 40.23/22.8% | 30.36/19.3% | 38.36/23.2% |
| AIS#1468 | 82.16/57.0% | 94.16/60.3% | 107.91/64.0% | 115.91/65.6% | 96.04/61.0% | 104.04/62.9% |
| AIS#1513 | 107.73/74.8% | 119.73/76.7% | 129.10/76.6% | 137.10/77.6% | 119.41/75.9% | 127.41/77.1% |
| CTR#69 | 141.68/— | 153.68/— | 163.73/— | 171.73/— | 153.70/— | 161.70/— |
| AIS#1488 | 41.30/29.2% | 43.30/28.2% | 54.43/33.2% | 52.43/30.5% | 43.87/28.5% | 51.87/32.1% |
| AIS#1198 | 72.90/51.5% | 84.90/55.2% | 94.57/57.8% | 102.57/59.7% | 84.73/55.1% | 92.73/57.3% |
| AIS#1385 | 66.15/46.7% | 78.15/50.9% | 84.86/51.8% | 92.86/54.1% | 76.50/49.8% | 84.50/52.3% |
| | | | BP554 | | | |
| CTR#60 | 140.49/— | 152.49/— | 162/— | 170/— | 152.25/— | 160.25/— |
| AIS#1474 | 39.94/28.4% | 41.94/27.5% | 51.45/31.8% | 50.45/29.7% | 43.7/28.7% | 46.7/29.1% |
| AIS#1550 | 74.64/53.1% | 86.64/56.8% | 91.46/56.5% | 99.46/58.5% | 84.05/55.2% | 92.05/57.4% |
| AIS#1020 | 62.57/44.5% | 64.57/42.3% | 78.63/48.5% | 76.63/45.1% | 66.6/43.7% | 74.6/46.6% |
| CTR#61 | 132.45/— | 144.45/— | 154.6/— | 162.6/— | 144.53/— | 152.53/— |
| AIS#1549 | 16.43/12.4% | 28.43/19.7% | 38.57/24.9% | 46.57/28.6% | 28.5/19.7% | 36.5/23.9% |
| AIS#1468 | 84.51/63.8% | 96.51/66.8% | 104.4/67.5% | 112.4/69.1% | 95.45/66.0% | 103.45/67.8% |
| AIS#1513 | 91.15/68.8% | 103.15/71.4% | 113.38/73.3% | 121.38/74.6% | 103.27/71.5% | 111.27/72.9% |
| CTR#69 | 145.69/— | 157.69/— | 165.87/— | 173.87/— | 156.78/— | 164.78/— |
| AIS#1488 | 44.06/30.2% | 46.06/29.2% | 54.24/32.7% | 52.24/30.0% | 45.15/28.8% | 53.15/32.3% |
| AIS#1198 | 59.83/41.1% | 64.83/41.1% | 74.63/45.0% | 70.63/40.6% | 63.73/40.6% | 71.73/43.5% |
| AIS#1385 | 73.41/50.4% | 68.41/43.4% | 86.15/51.9% | 85.15/49.0% | 72.78/46.4% | 73.78/44.8% |
| | | | UK14304 | | | |
| CTR#60 | 100.78/— | 106.78/— | 125.27/— | 127.27/— | 111.02/— | 119.02/— |
| AIS#1474 | 20.6/20.4% | 20.6/19.3% | 23.35/18.6% | 24.35/19.1% | 19.48/17.5% | 19.48/16.4% |
| AIS#1550 | 53.62/53.2% | 45.62/42.7% | 56.75/45.3% | 44.75/35.2% | 46.19/41.6% | 54.19/45.5% |
| AIS#1020 | 42.74/42.4% | 39.74/37.2% | 43.5/34.7% | 51.5/40.5% | 41.62/37.5% | 49.62/41.7% |
| CTR#61 | 90.39/— | 94.39/— | 102.1/— | 110.1/— | 92.75/— | 101.75/— |
| AIS#1549 | 27.08/30.0% | 29.08/30.8% | 34.45/33.7% | 36.45/33.1% | 32.76/35.3% | 36.76/36.1% |
| AIS#1468 | 65.72/72.7% | 67.72/71.7% | 77.77/76.2% | 75.77/68.8% | 67.75/68.8% | 75.75/73.0% |
| AIS#1513 | 58.45/64.7% | 60.45/64.0% | 71.58/70.1% | 69.58/63.2% | 61.02/65.8% | 69.02/67.8% |
| CTR#69 | 103.67/— | 105.67/— | 98.38/— | 100.38/— | 94.02/— | 92.02/— |
| AIS#1488 | 26.24/25.3% | 25.55/24.2% | 25.92/26.3% | 18.92/18.8% | 26.55/28.2% | 26.24/28.5% |
| AIS#1198 | 44.16/42.6% | 46.16/43.7% | 56.22/57.1% | 54.22/54.0% | 46.19/49.1% | 54.19/58.9% |
| AIS#1385 | — | — | — | — | — | — |

TABLE VII

Differences observed between minimal and maximal values for each group and minimal and maximal values from control subjects for various ligands in osteoblasts. Values were calculated from the data shown in FIGS. 11A-11F.

| | | Absolute dZiec | % of control signal (min/max) |
|---|---|---|---|
| Melatonin | | | |
| Group 1 | min diff. | 18/60 | 30% |
| | max diff. | 11/83 | 13% |
| Group 2 | min diff. | 37/60 | 62% |
| | max diff. | 28/83 | 34% |
| Group 3 | min diff. | 50/60 | 83% |
| | max diff. | 45/83 | 54% |
| Iodomelatonine | | | |
| Group 1 | min diff. | 35/120 | 29% |
| | max diff. | 15/159 | 9% |
| Group 2 | min diff. | 84/120 | 70% |
| | max diff. | 57/159 | 36% |
| Group 3 | min diff. | 101/120 | 84% |
| | max diff. | 90/159 | 57% |
| BP554 | | | |
| Group 1 | min diff. | 49/128 | 38% |
| | max diff. | 32/166 | 19% |
| Group 2 | min diff. | 88/128 | 69% |
| | max diff. | 67/166 | 40% |
| Group 3 | min diff. | 107/128 | 84% |
| | max diff. | 99/166 | 60% |
| UK14304 | | | |
| Group 1 | min diff. | 32/98 | 33% |
| | max diff. | 21/115 | 18% |
| Group 2 | min diff. | 50/98 | 51% |
| | max diff. | 45/115 | 39% |
| Group 3 | min diff. | 71/98 | 72% |
| | max diff. | 60/115 | 52% |
| IB-meca | | | |
| Group 1 | min diff. | 43/132 | 33% |
| | max diff. | 20/172 | 12% |
| Group 2 | min diff. | 80/132 | 61% |
| | max diff. | 73/172 | 42% |
| Group 3 | min diff. | 115/132 | 87% |
| | max diff. | 98/172 | 55% |

TABLE VII-continued

Differences observed between minimal and maximal values for each group and minimal and maximal values from control subjects for various ligands in osteoblasts. Values were calculated from the data shown in FIGS. 11A-11F.

| | | Absolute dZiec | % of control signal (min/max) |
|---|---|---|---|
| CB65 | | | |
| Group 1 | min diff. | 47/138 | 34% |
| | max diff. | 34/169 | 20% |
| Group 2 | min diff. | 88/138 | 64% |
| | max diff. | 60/169 | 36% |
| Group 3 | min diff. | 123/138 | 89% |
| | max diff. | 100/169 | 55% |

TABLE VIII

Differences observed between minimal and maximal values for each group and minimal and maximal values for control subjects for iodomelatonine in PBMCs. Values were calculated from the data shown in FIG. 12A.

| Iodomelatonine | | Absolute dZiec | % of control signal (min/max) |
|---|---|---|---|
| Group 1 | min diff. | 36/124 | 29% |
| | max diff. | 16/225 | 7% |
| Group 2 | min diff. | 75/124 | 60% |
| | max diff. | 49/225 | 22% |
| Group 3 | min diff. | 110/124 | 89% |
| | max diff. | 86/1125 | 38% |

Example 8

Stratification/Classification of IS Subjects Based on Gi-Coupled Receptor Responses Measured in PBMCs A cohort of individuals with (n=45) (see Table II) or without AIS (n=42) (See Table I) was tested to determine the sensitivity and specificity of the cell-based assay with CDS by investigating the functional status of melatonin signaling in PBMCs (including principally lymphocytes) from each of these individuals.

PBMCs were isolated from control subjects, IS subjects as described in Example 2 above. The signaling effect of 300 µM of iodomelatonin as measured by Cellular Dielectric Spectroscopy (CDS) was determined.

Figure 12A:
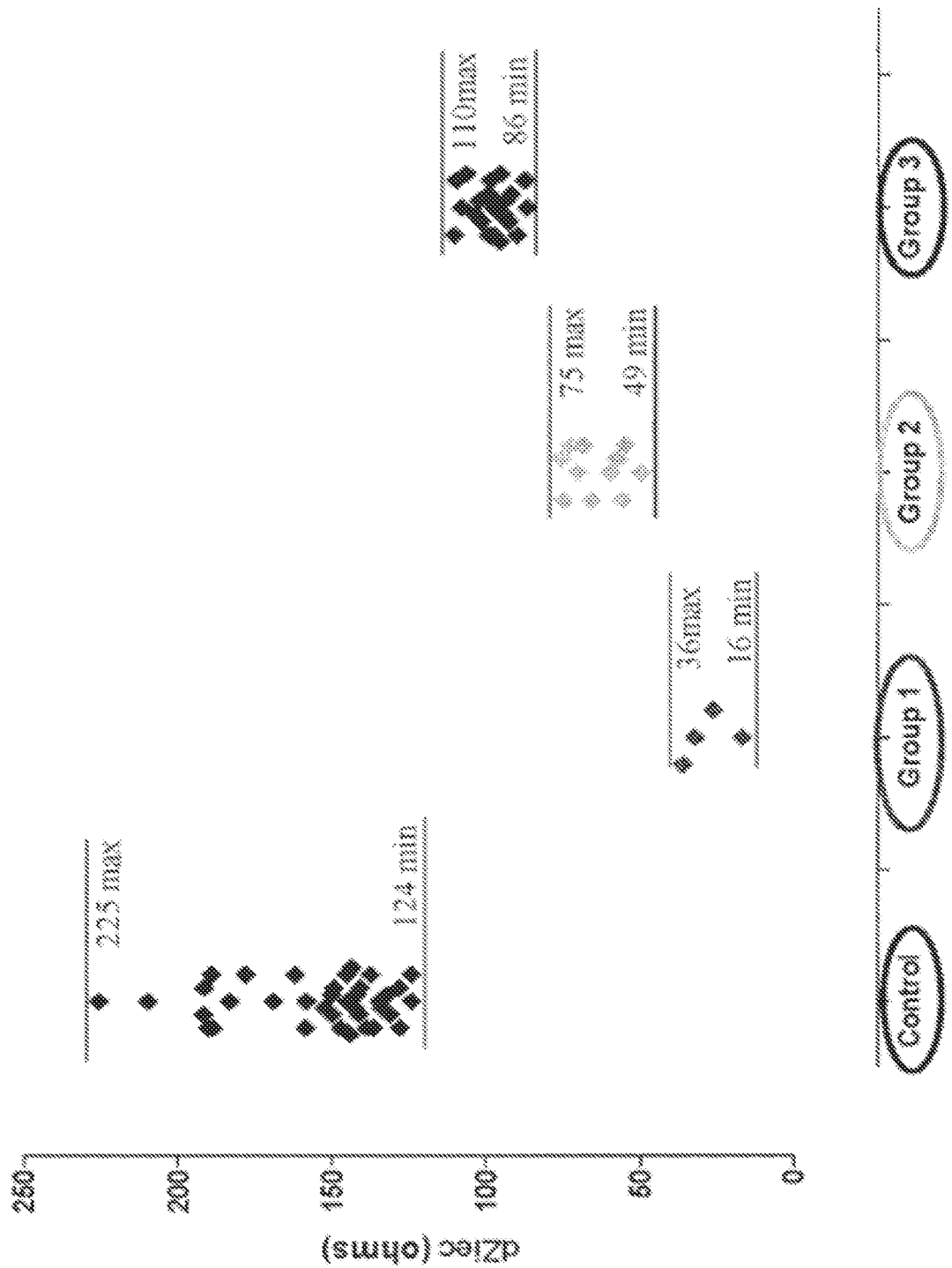
FIGS. 12A and 12B show ranges of values obtained in PBMCs from control subjects and AIS patients (FIG. 12A) or asymptomatic at risk subjects (FIG. 12B), using 300 μM of iodomelatonin as measured by Cellular Dielectric Spectroscopy (CDS). Each point represents the mean of three wells on individual subjects and the assay coefficient of variation found was typically less than 10%.

FIG. 12A shows that all patients with IS were less responsive to iodomelatonin when compared to healthy volunteers tested (control). Similar results were obtained with melatonin (data not shown), thereby indicating a high selectivity for this assay. The minimal magnitude measured in PBMCs from healthy volunteers in response to iodomelatonin was 124 ohms under experimental conditions. None of the AIS patients tested exhibited a CDS response reaching such magnitude. The maximal magnitude measured in IS patients was 110 ohms, while the minimum was 16 ohms. Melatonin signaling responses to iodomelatonin in normal/healthy subjects was thus greater than 120 ohms. A CDS response range between 10 and 40 ohms for IS patients was classified in group 1, 40 and 80 ohms in group 2, and finally between 80 and 120 ohms for IS patients in group 3. Of all AIS patients tested, 11% (5/44), 30% (13/44) and 59% (26/44) were diagnosed as belonging to the functional groups 1, 2 and 3, respectively. According to their CDS response, there was no ambiguity in classifying these patients. The mean of CDS response for group 1 was 27.86±4.18 and 65.71±3.42 for group 2, while it was 97.94±1.36 for group 3 and 155.17±3.91 for the control group. These differences were highly significant (P<0.001). These results demonstrate that the functional test based on the evaluation of melatonin signaling in PBMCs with the CDS assay effectively distinguishes patients with IS not only from healthy individuals but also from different functional groups. These results demonstrate the sensitivity, specificity and dynamic range of this functional test as a diagnostic tool. See also Table VII showing Differences observed between minimal and maximal values for each group and minimal and maximal values for control subjects for iodomelatonine in PBMCs.

Example 9

Predicting the Risk of Developing IS in PBMCs

Healthy controls (n=42) (Table I) or subjects considered at risk of developing this disease (n=30) (Table III) were tested to determine the ability of this assay to predict the risk of developing IS.

PBMCs were isolated asymptomatic at-risk subjects as described in Example 2 above. The signaling effect of 300 µM of iodomelatonin as measured by Cellular Dielectric Spectroscopy (CDS) was determined in these cells and compared with that measured in the healthy controls described in Example 6 above.

Figure 12B:
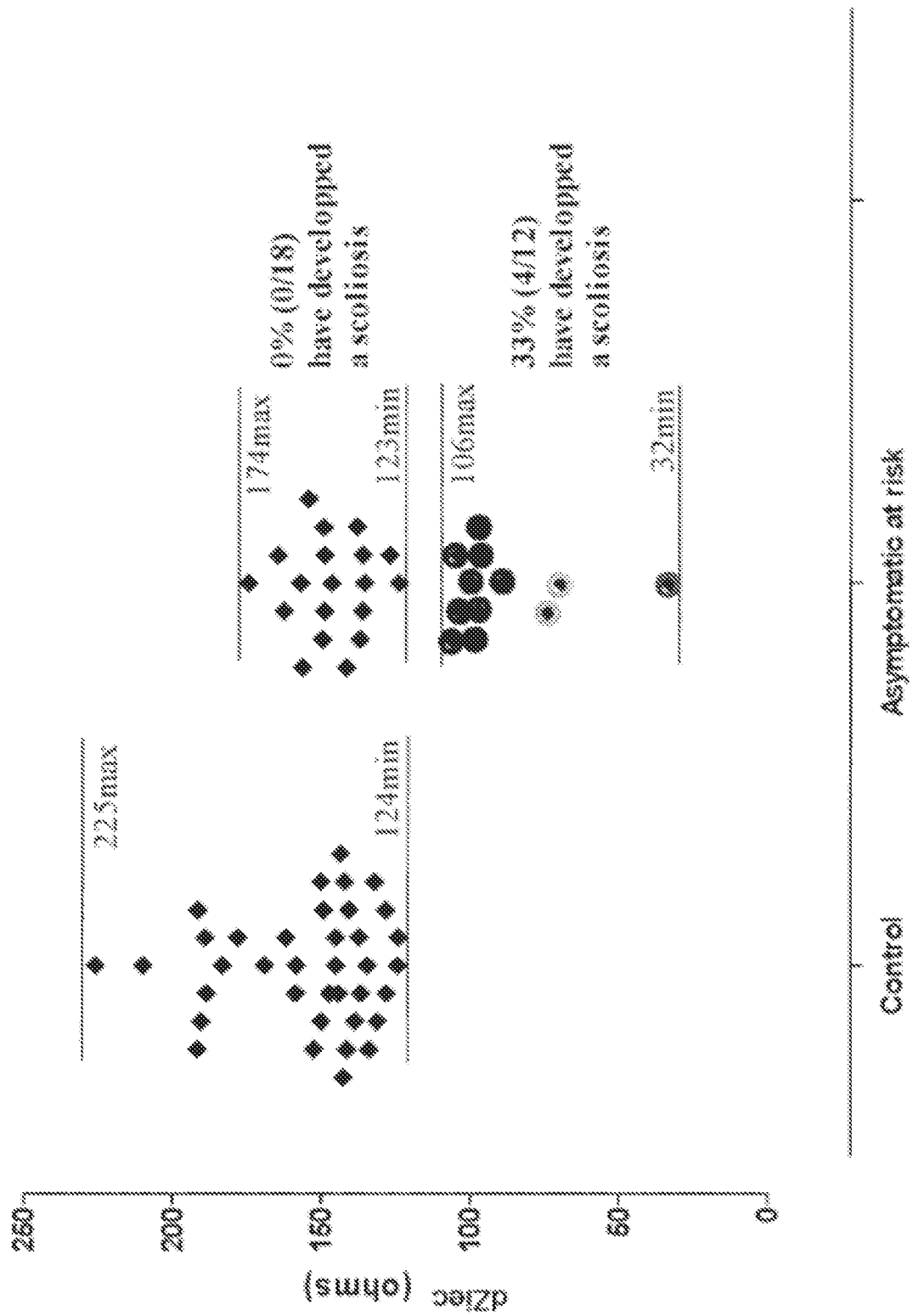

The functional screening of PBMCs from asymptomatic children born from at least one scoliotic parent revealed that the melatonin signaling defect can be detected in this cohort (FIG. 12B). Of all asymptomatic children tested, 60% (19/31) exhibited a CDS response in the range of normal magnitudes (>120 ohms), whereas the CDS response was reduced in 40% (12/31). The latter group was considered more susceptible to developing scoliosis. Among these 12 children at high risk, 4 (33%) have developed a spinal deformity 24 months later, exhibiting a mean Cobb angle of 11.7° as confirmed by radiography (data not shown). None of the 19 in the normal range has developed a scoliosis.

It is known that the prevalence of IS is increased in asymptomatic children born from at least one affected parent. Results presented above corroborate this fact and confirm that this category of children is more susceptible of developing IS. The risk of developing scoliosis was predicted in 40% of asymptomatic children tested (i.e. 12/31), and 33% of them developed a spinal deformity several months later. For instance the then asymptomatic patient #3116 in Table III (who was then 9 years old), at age 11 presented a curve pattern right thoracic and left lumbar with a Cobb angle of 9-14°.

The lack of spinal deformity manifestation in the remaining 67% of the suspected children is likely related to their age. Indeed, the deformity of the spine is recognized to occur in children between 10 and 16 years of age. However, the mean age of asymptomatic children enrolled in the present study was 10.2±3.2 years, and they have been followed up for 24 months. Therefore, not all tested children would have reached the appropriate age for developing the spinal deformity during this period.

Among all tested children (including those of age 10 or older (scoliosis appears around in the age 10)), neither asymptomatic children exhibiting normal melatonin signaling nor control children without familial history of scoliosis have developed any spinal deformity during the study period.

Example 10

Figure 13A:
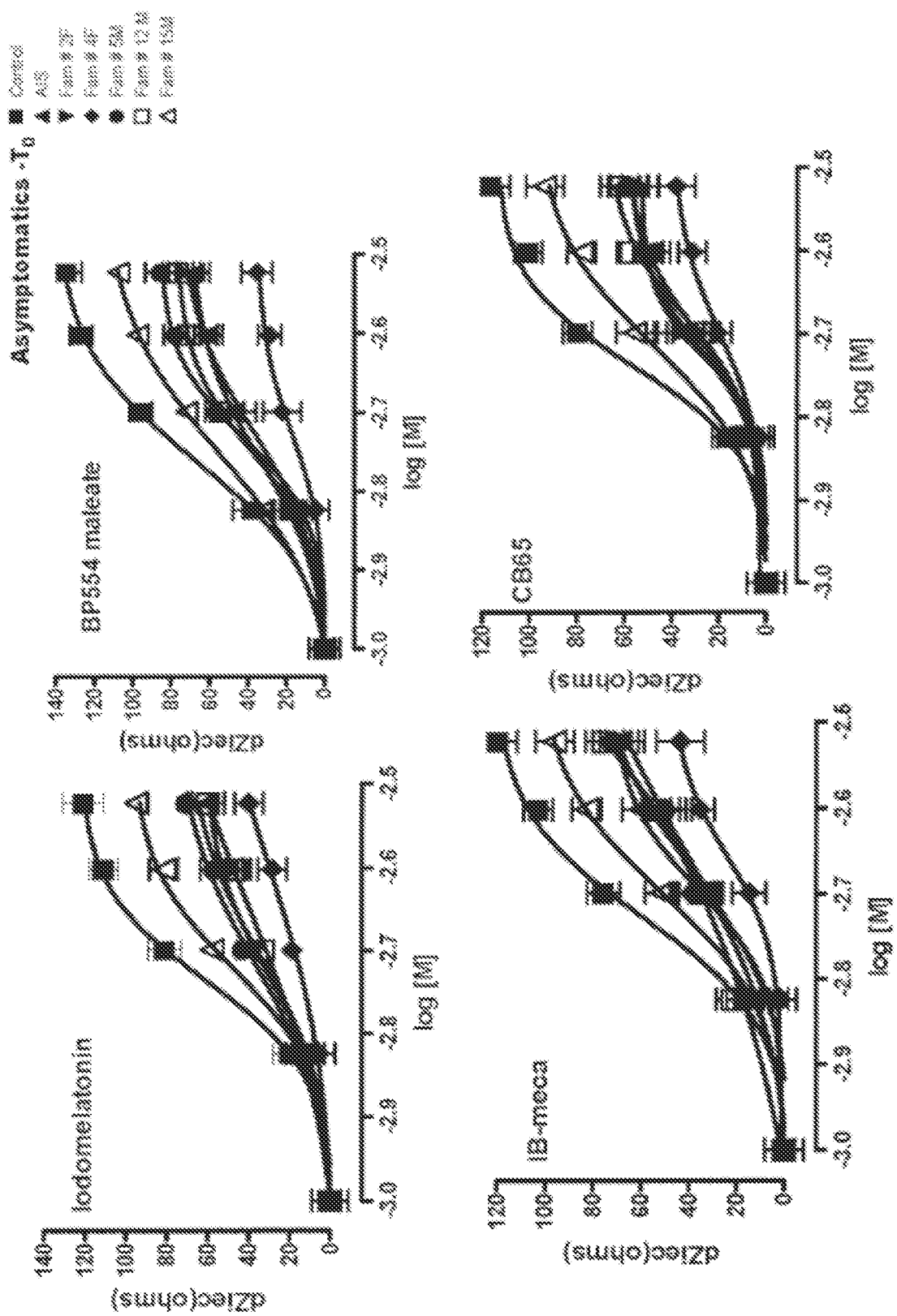
FIGS. 13A and 13B show the response of different receptors coupled to $G_i$ proteins expressed on PBMCs obtained from asymptomatic at risk patients, AIS subjects and control subjects and following activation by a specific ligand, as measured by Cellular Dielectric Spectroscopy (CDS) at time zero (To) and eighteen months later ($T_{18}$).
Figure 13B:
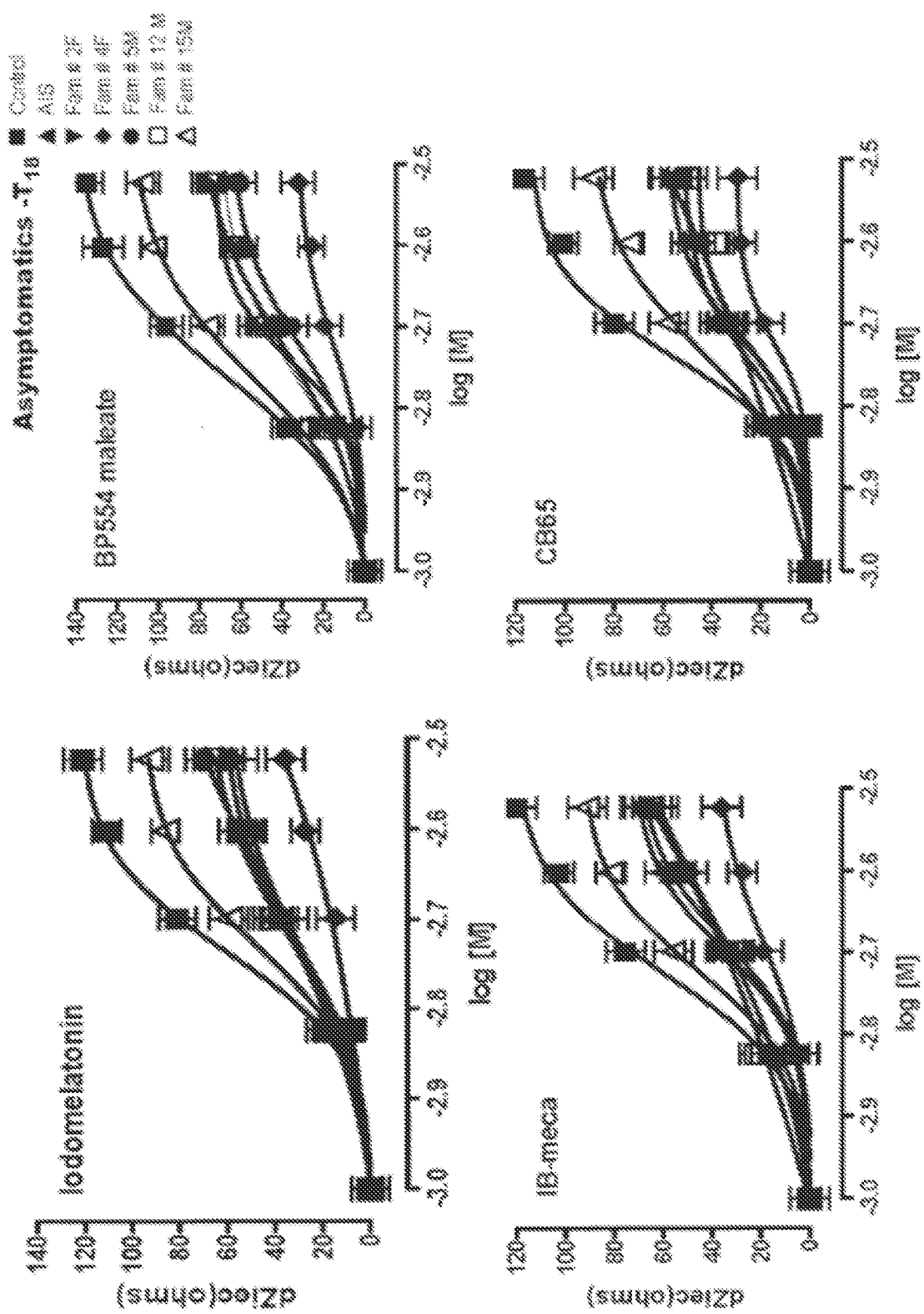
Figure 13C:
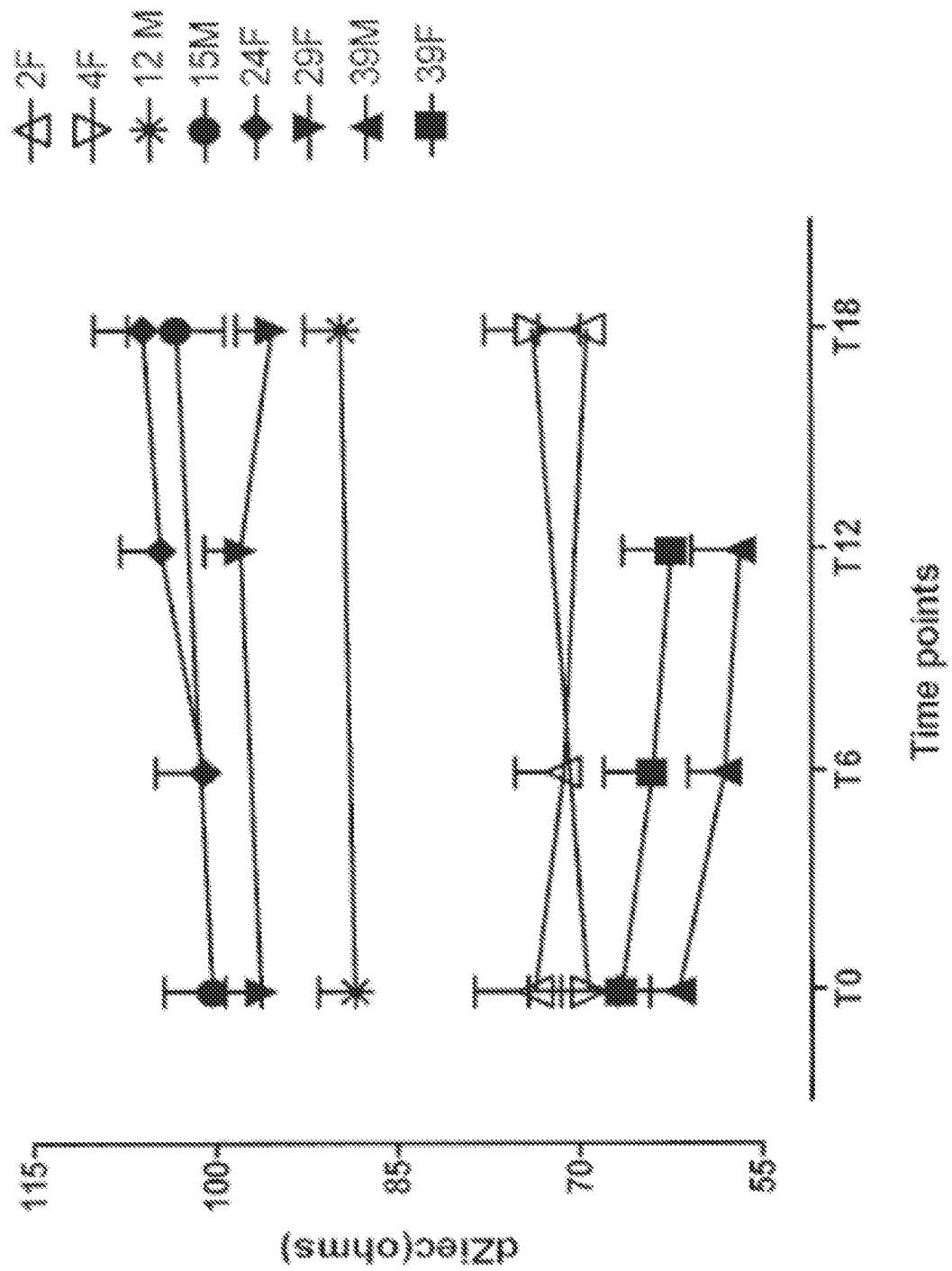
FIG. 13C provides on a single graph the response to the melatonin receptor on PBMCs (containing principally lymphocytes) obtained from asymptomatic at risk patients.

Measurement of Gi-Coupled Receptor Responses in Asymptomatic at Risk Subjects FIGS. 13A and 13B show that the defect in $G_i$-coupled receptors response may be detected over a period of 18 months in PBMCs (including principally lymphocytes) of asymptomatic at risk subjects (n=31) (subjects having a parent affected by AIS). Also, the amplitude of the defect is maintained over this period (i.e. subjects showed a very similar response curve at the first time point ($t_0$) and 18 months later ($t_{18}$)), suggesting that the defect does not evolve over time.

Example 11

Measurement of Gi-Coupled Receptor Responses in Osteoblasts

Figure 14A:
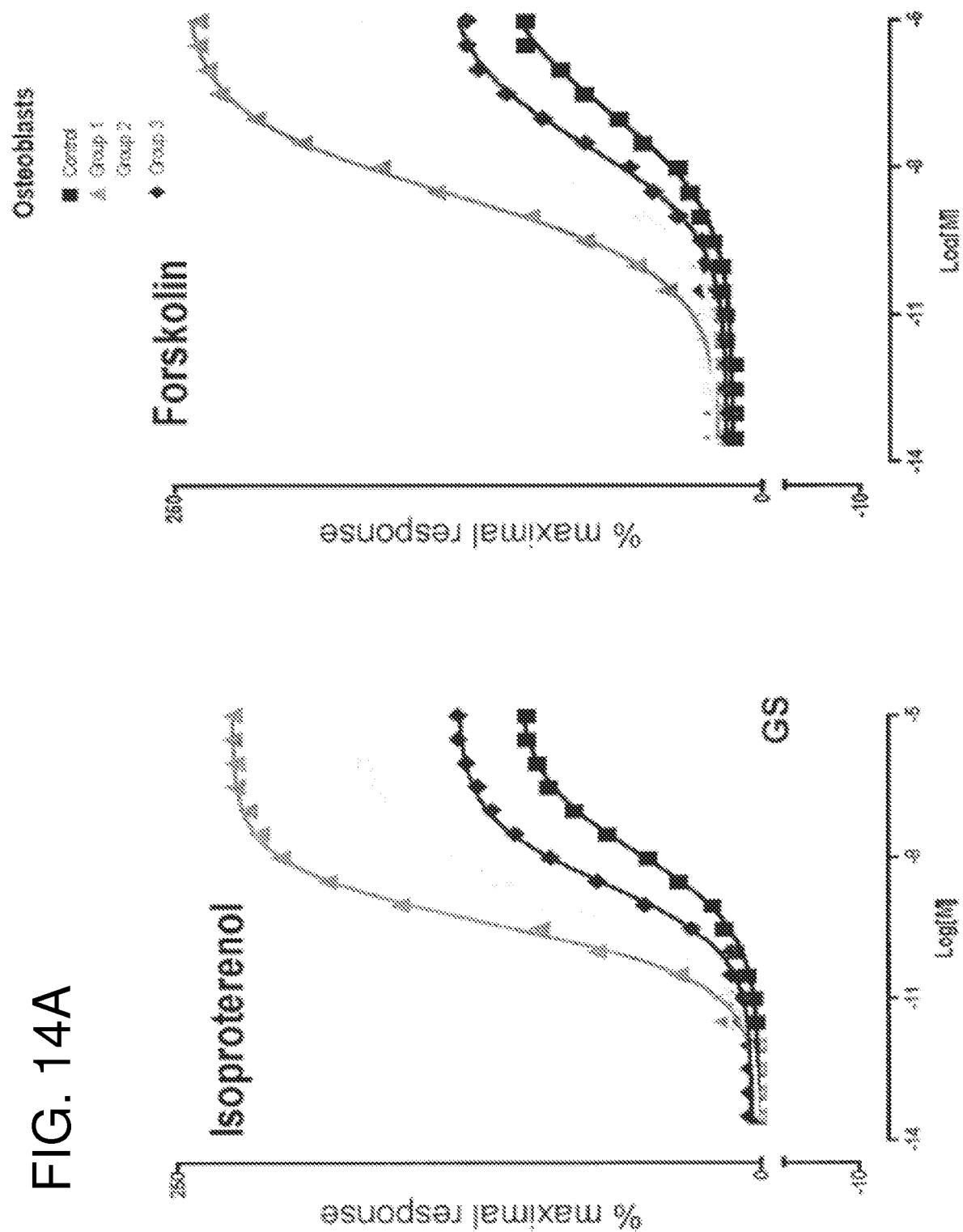
FIGS. 14A and 14B show GPRC signaling in osteoblasts of a control subject and of AIS subjects (Groups 1, 2 and 3) using different ligands Gs, Gi and Gq to determine whether the signaling is specific to Gi-coupled receptor.
Figure 14B:
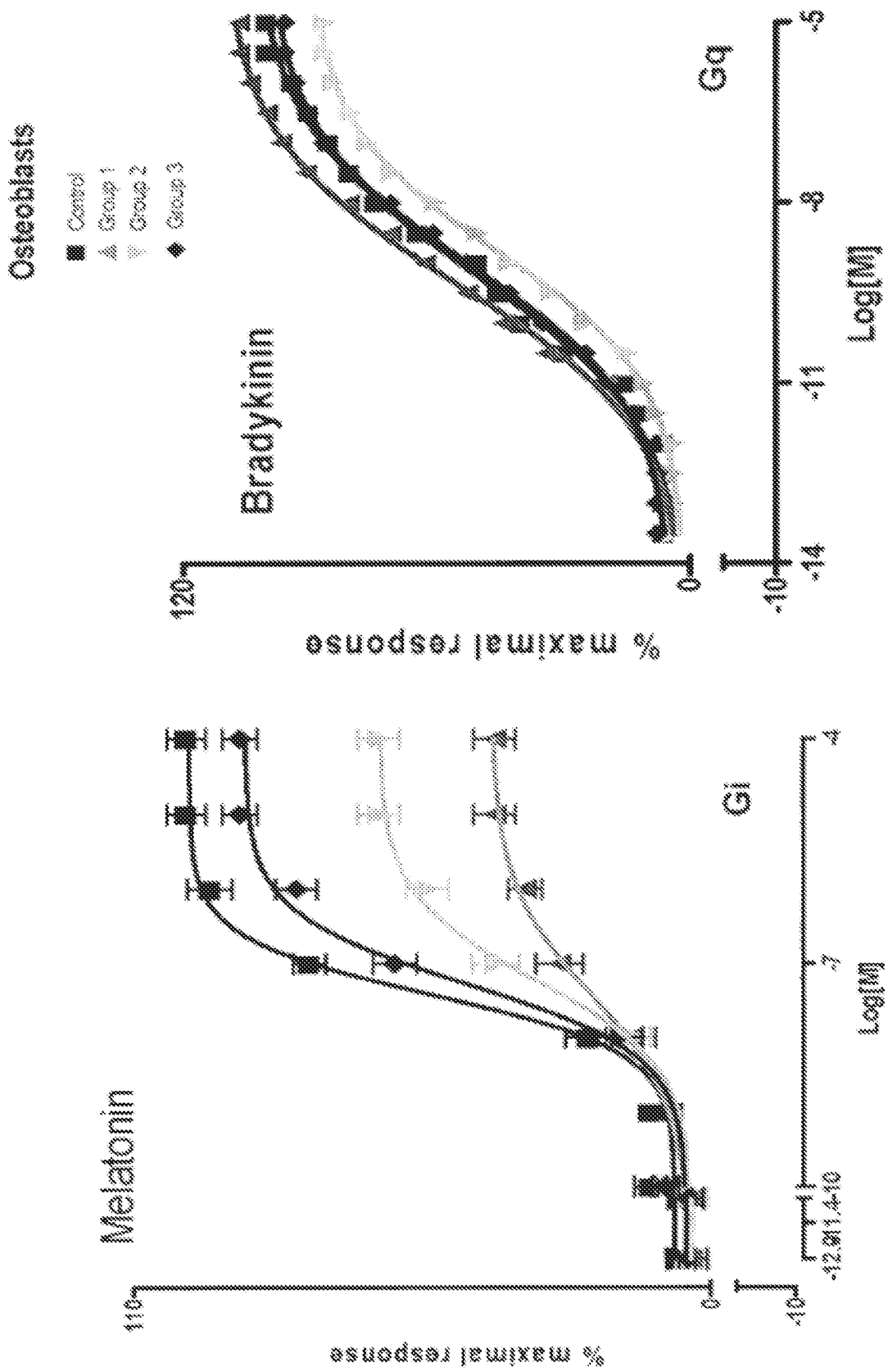

Osteoblasts were seeded into the CELLKEY™ label-free cellular analysis system standard 96-well microplate at a density of $5 \times 10^4$/150 uL per well and incubated in standard conditions (37° C./5% $CO_2$). Following overnight incubation, the plate was placed onto the CELLKEY™ label-free cellular analysis system and growth medium was replaced by assay buffer (Hanks, Balanced Salt Solution containing 20 mM HEPES and 0.1% BSA) before starting the experiment. Cells were then allowed to equilibrate at room temperature for 30 min. At the end of this period, the plate was placed onto the system and pre-addition measurements were made for 5 min to obtain a baseline reading. Then, forskolin, isoproterenol, melatonin or bradykinin was added simultaneously to all 96 wells with an integrated fluidics system. The compound addition resulted in change in impedance that started occurring immediately after fluid addition and mixing. Impedance measurements were collected for 15 min at 28° C. FIGS. 14A-14B show that GPCR signaling in AIS is specific to $G_i$ coupled receptor. The difference in response observed for $G_s$-coupled GPCR in the presence of isoproterenol as well in the production of cAMP in the presence of forskolin between each groups is explained by the absence of functional $G_i$. There is approximately 10 times more $G_i$ than Gs in the cells. Therefore, if some $G_i$ is non-functional, it cannot inhibit the production of cAMP in the presence of forskolin and thus, the $G_s$-coupled response also appears affected.

Although the present invention has been described hereinabove by way of specific embodiments thereof, it can be modified, without departing from the spirit and nature of the subject invention as defined in the appended claims.

The invention claimed is:

1. An electrified composition for determining the risk of developing adolescent idiopathic scoliosis (AIS) comprising:
   i) a primary cell expressing a native receptor coupled to an inhibitory guanine nucleotide-binding ($G_i$) protein (GiPCR) obtained from a biological fluid sample from a human pediatric subject, wherein said subject is suffering from AIS or has a parent who suffers from AIS, wherein said primary cell is a peripheral blood mononuclear cell (PBMC), an osteoblast or a myoblast, and wherein said GiPCR is a serotonin 1A receptor (5-HT1A);
   ii) a ligand to said GiPCR, wherein said ligand is 1-[3-(3,4-Methylenedioxyphenoxy)propyl]-4-phenyl-piperazine maleate (BP554 maleate); and
   iii) an isotonic buffer comprising Hanks' balanced salt solution (HBSS) suitable for measuring cellular impedance by cellular dielectric spectroscopy (CDS);
wherein said composition has been electrified by applying voltage at 24 frequencies from 1 KHz to 10 MHz across electrodes in contact with said composition.

2. The composition of claim 1, wherein said subject has a parent who suffers from adolescent idiopathic scoliosis.

3. The composition of claim 1, wherein said subject has been diagnosed with adolescent idiopathic scoliosis.

4. The composition of claim 1, wherein said primary cell is a peripheral blood mononuclear cell (PBMC).

5. The composition of claim 1, wherein said primary cell is an osteoblast or a myoblast.

6. The composition of claim 1, wherein said primary cell has previously been frozen.

7. The composition of claim 1, wherein said primary cell is a fresh cell, which has not been frozen.

8. An electrified composition for determining the risk of developing adolescent idiopathic scoliosis (AIS) comprising:
   i) a primary cell expressing a native receptor coupled to an inhibitory guanine nucleotide-binding ($G_i$) protein (GiPCR) obtained from a biological fluid sample from a human pediatric subject, wherein said subject is suffering from AIS or has a parent who suffers from AIS, wherein said primary cell is a peripheral blood mononuclear cell (PBMC), an osteoblast or a myoblast, and wherein said GiPCR is a CB2 cannabinoid receptor (CB2);
   ii) a ligand to said GiPCR, wherein said ligand is N-Cyclohexyl-7-chloro-1-[2-(4-morpholinyl)ethyl]quinolin-4(1H)-one-3-carboxamide (CB65); and
   iii) an isotonic buffer comprising Hanks' balanced salt solution (HBSS) suitable for measuring cellular impedance by cellular dielectric spectroscopy (CDS);
wherein said composition has been electrified by applying voltage at 24 frequencies from 1 KHz to 10 MHz across electrodes in contact with said composition.

9. The composition of claim 8, wherein said subject has a parent who suffers from adolescent idiopathic scoliosis.

10. The composition of claim 8, wherein said subject has been diagnosed with adolescent idiopathic scoliosis.

11. The composition of claim 8, wherein said primary cell is a peripheral blood mononuclear cell (PBMC).

12. The composition of claim 8, wherein said primary cell is an osteoblast or a myoblast.

13. The composition of claim 8, wherein said primary cell has previously been frozen.

14. The composition of claim 8, wherein said primary cell is a fresh cell, which has not been frozen.

15. An electrified composition for determining the risk of developing adolescent idiopathic scoliosis (AIS) comprising:
   i) a primary cell expressing a native receptor coupled to an inhibitory guanine nucleotide-binding ($G_i$) protein (GiPCR) obtained from a biological fluid sample from a human pediatric subject, wherein said subject is suffering from AIS or has a parent who suffers from AIS, wherein said primary cell is a peripheral blood mononuclear cell (PBMC), an osteoblast or a myoblast, and wherein said GiPCR is an alpha-2 adrenergic receptor (α2-AD);

ii) a ligand to said GiPCR, wherein said ligand is 5-bromo-N-(4,5-dihydro-1H-imidazol-2-yl)-6-quinoxalinamine (UK14304); and iii) an isotonic buffer comprising Hanks' balanced salt solution (HBSS) suitable for measuring cellular impedance by cellular dielectric spectroscopy (CDS);

wherein said composition has been electrified by applying voltage at 24 frequencies from 1 KHz to 10 MHz across electrodes in contact with said composition.

16. The composition of claim 15, wherein said subject has a parent who suffers from adolescent idiopathic scoliosis.

17. The composition of claim 15, wherein said subject has been diagnosed with adolescent idiopathic scoliosis.

18. The composition of claim 15, wherein said primary cell is a peripheral blood mononuclear cell (PBMC).

19. The composition of claim 15, wherein said primary cell is an osteoblast or a myoblast.

20. The composition of claim 15, wherein said primary cell has previously been frozen.

21. The composition of claim 15, wherein said primary cell is a fresh cell, which has not been frozen.

22. An electrified composition for determining the risk of developing adolescent idiopathic scoliosis (AIS) comprising:

i) a primary cell expressing a native receptor coupled to an inhibitory guanine nucleotide-binding (G$_i$) protein (GiPCR) obtained from a biological fluid sample from a human pediatric subject, wherein said subject is suffering from AIS or has a parent who suffers from AIS, wherein said primary cell is a peripheral blood mononuclear cell (PBMC), an osteoblast or a myoblast, and wherein said GiPCR is an A3 adenosine receptor (A3);

ii) a ligand to said GiPCR, wherein said ligand is 1-Deoxy-1-[6-[[(3-iodophenyl)methyl]amino]-9H-purin-9-yl]-N-methyl-β-D-ribofuranuronamide (IB-MECA); and iii) an isotonic buffer comprising Hanks' balanced salt solution (HBSS) suitable for measuring cellular impedance by cellular dielectric spectroscopy (CDS);

wherein said composition has been electrified by applying voltage at 24 frequencies from 1 KHz to 10 MHz across electrodes in contact with said composition.

23. The composition of claim 22, wherein said subject has a parent who suffers from adolescent idiopathic scoliosis.

24. The composition of claim 22, wherein said subject has been diagnosed with adolescent idiopathic scoliosis.

25. The composition of claim 22, wherein said primary cell is a peripheral blood mononuclear cell (PBMC).

26. The composition of claim 22, wherein said primary cell is an osteoblast or a myoblast.

27. The composition of claim 22, wherein said primary cell has previously been frozen.

28. The composition of claim 22, wherein said primary cell is a fresh cell, which has not been frozen.

* * * * *